United States Patent
Madlener et al.

(10) Patent No.: US 10,183,976 B2
(45) Date of Patent: Jan. 22, 2019

(54) METHOD FOR PRODUCING FACTOR H FROM A PLASMA PRECIPITATION FRACTION

(71) Applicants: Baxalta Incorporated, Bannockburn, IL (US); Baxalta GmbH, Zug (CH)

(72) Inventors: Ruth Madlener, Vienna (AT); Wolfgang Teschner, Vienna (AT); Hans-Peter Schwarz, Vienna (AT); Sonja Svatos, Berg (AT); Azra Pljevljakovic, Vienna (AT); Lena Nitsch, Vienna (AT)

(73) Assignees: Baxalta Incorporated, Bannockburn, IL (US); Baxalta GmbH, Zug (CH)

( * ) Notice: Subject to any disclaimer, the term of this patent is extended or adjusted under 35 U.S.C. 154(b) by 0 days.

(21) Appl. No.: 14/213,924

(22) Filed: Mar. 14, 2014

(65) Prior Publication Data
US 2014/0275484 A1 Sep. 18, 2014

Related U.S. Application Data

(60) Provisional application No. 61/793,563, filed on Mar. 15, 2013.

(51) Int. Cl.
*C07K 14/47* (2006.01)
*C07K 1/30* (2006.01)
(Continued)

(52) U.S. Cl.
CPC .......... *C07K 14/47* (2013.01); *A61K 38/1725* (2013.01); *A61K 35/16* (2013.01)

(58) Field of Classification Search
None
See application file for complete search history.

(56) References Cited

U.S. PATENT DOCUMENTS

7,351,524 B2   4/2008   Hageman et al.
7,745,389 B2   6/2010   Hageman
(Continued)

FOREIGN PATENT DOCUMENTS

EP   0 222 611 A2   5/1987
WO   WO 00/52479 A2   9/2000
(Continued)

OTHER PUBLICATIONS

Brandstätter, H. et al., "Purification and biochemical characterization of functional complement factor H from human plasma fractions," *Vox Sanguinis*, 2012; 103:201-212.
(Continued)

*Primary Examiner* — Marsha Tsay
(74) *Attorney, Agent, or Firm* — Morgan, Lewis & Bockius LLP

(57) ABSTRACT

The present disclosure provides, among other aspects, improved methods for the manufacture of Factor H compositions from plasma precipitation fractions. In some aspects, the methods include an improved process step for extracting Factor H from a plasma precipitate fraction with reduced co-extraction of amidolytic activities. In other aspects, the methods include a heat treatment step for reducing impurities, such as amidolytic enzymes, from a Factor H composition. In yet other aspects, the methods include improved anion exchange, heparin affinity, and/or mixed mode chromatographic enrichment of Factor H. In still other aspects, the improved methods include a combination of the individual improved process steps disclosed herein.

19 Claims, 13 Drawing Sheets

(51) Int. Cl.
| | |
|---|---|
| C07K 1/34 | (2006.01) |
| C07K 1/36 | (2006.01) |
| C07K 1/14 | (2006.01) |
| C07K 1/16 | (2006.01) |
| C07K 1/18 | (2006.01) |
| C07K 1/22 | (2006.01) |
| A61K 38/17 | (2006.01) |
| A61K 35/16 | (2015.01) |

(56) References Cited

U.S. PATENT DOCUMENTS

| | | |
|---|---|---|
| 8,304,524 B2 | 11/2012 | Bairstow et al. |
| 2009/0118163 A1 | 5/2009 | Gronski et al. |
| 2011/0021432 A1* | 1/2011 | Bairstow ............ A61K 38/1709 514/15.3 |

FOREIGN PATENT DOCUMENTS

| | | | |
|---|---|---|---|
| WO | WO 2006/062716 A2 | 6/2006 | |
| WO | WO 2007/066017 A2 | 6/2007 | |
| WO | WO 2007/149567 A2 | 12/2007 | |
| WO | WO 2008113589 A1 * | 9/2008 | ........... A61K 9/0019 |
| WO | WO 2011/011753 A1 | 1/2011 | |
| WO | WO 2011/150284 A2 | 12/2011 | |

OTHER PUBLICATIONS

Cohn, E.J. et al., "Preparation and Properties of Serum and Plasma Proteins, IV. A System for the Separation into Fractions of the Proteins and Lipoprotein Components of Biological Tissues and Fluids," *J Am Chem Soc*, Mar. 1946; 68:459-475.

Epstein, J.S. et al, "Current Safety of Clotting Factor Concentrates," *Arch Pathol Lab Med*, Mar. 1990; 114:335-340.

Hamamoto, Y. et al., "A Novel Method of Removal of Human Immunodeficiency Virus: Filtration with Porous Polymeric Membranes," *Vox Sang*, 1989; 56:230-236.

Horowitz, B. et al., "Viral safety of solvent/detergent-treated blood products," *Blood Coagulation and Fibrinolysis*, 1994; 5(3):S21-S28.

International Search Report for International Patent Application No. PCT/US2014/029313 dated Oct. 9, 2014, 5 pages.

Kempf, C. et al., "Virus inactivation during production of intravenous immunoglobulin," *Transfusion*, 1991; 31:423-427.

Kistler, P. et al., "Large Scale Production of Human Plasma Fractions," *Vox Sang*, 1962: 7:414-424.

Kreil, T.R. et al., "West Nile virus and the safety of plasma derivatives: verification of high safety margins, and the validity of predictions based on model virus data," *Transfusion*, Aug. 2003; 43:1023-1028.

Louie, R.E. et al., "Inactivation of Hepatitis C Virus in Low pH Intravenous Immunoglobulin," *Biologicals*, 1994; 22:13-19.

Oncley, J.L. et al., "The Separation of the Antibodies, Isoagglutinins, Prothrombin, Plasminogen and $\beta_1$-Lipoproteins into Subfractions if Human Plasma," *J Am Chem Soc*, Feb. 1949; 71:541-550.

Pelletier, J.P.R. et al., "Pathogen inactivation techniques," *Best Practice & Research Clinical Haematology*, 2006; 19(1):205-242.

Piszkiewicz, D. et al., "Heat Inactivation of Human Immunodeficieny Virus in Lyophilized Factor VIII and Factor IX Concentrates," *Thrombosis Research*, 1987; 47:235-241.

Piszkiewicz, D. et al., "Virus Inactivation by Heat Treatment of Lyophilized Coagulation Factor Concentrates," *Curr Stud Hematol Blood Transfus.*, 1989; 56:44-54.

Yuasa, T. et al., "The particle size of hepatitis C virus estimated by filtration through microporous regenerated cellulose fibre," *Journal of General Virology*, 1991; 72:2021-2024.

* cited by examiner

| Lane 1 | Size Marker | % band at 140 kDa |
|---|---|---|
| Lane 2 | FH CompTech Standard | 5 |
| Lane 3 | FH012 FC | 57 |
| Lane 4 | FH184 FC | 18.5 |

Cleavage measured via ImageJ

| | Factor H preparation | Old purification pathway #FH012 at 2 % Protein | Improved purification pathway #FH184 at 1.4 % Protein |
|---|---|---|---|
| Specificity | Chromogenic Substrate | Hydrolysis rate [nmol/ml * min] | |
| Broad spectrum | PL-1 | 32.47 | < 5 |
| Broad spectrum | S-2288 | 106.17 | < 5 |
| FXIa, glandular kallikreins | S-2266 | 76.03 | < 5 |
| FXa, Trypsin | S-2222 | < 5 | < 5 |
| Plasmin | S-2251 | < 5 | < 5 |
| Kallikrein, FXIa, FXIIa | S-2302 | 248 | < 5 |

Figure 14

| Sample | Endotoxin | | Reduction |
|---|---|---|---|
| | IU/ml | IU total | % |
| Downstream and Formulation #FH184 | | | |
| DEAE Loading | 0.342 | 2282 | - |
| Heparin Eluate | 0.500 | 650 | 71.5 |
| Final Container | 0.484 (tested value by QC: <0.5) | 96 | 95.8 |

Figure 15

METHOD FOR PRODUCING FACTOR H FROM A PLASMA PRECIPITATION FRACTION

CROSS-REFERENCES TO RELATED APPLICATIONS

This application claims priority to U.S. Provisional Patent Application Ser. No. 61/793,563 filed Mar. 15, 2013, the disclosure of which is hereby incorporated herein by reference in its entirety for all purposes.

BACKGROUND OF THE INVENTION

Plasma-derived therapeutic proteins, unlike other biologics that are produced via recombinant expression of DNA vectors in host cell lines, are fractionated from human blood and plasma donations. The supply of these plasma-derived products cannot be increased by simply increasing the volume of production. Rather, the level of commercially available blood products is limited by the available supply of blood and plasma donations. This dynamic results in a shortage in the availability of raw human plasma for the manufacture of plasma-derived blood factors that have lesser established commercial markets, including Factor H (FH).

Factor H is a large (155 kDa), soluble glycoprotein that functions in the regulation of the complement Alternative Pathway to ensuring that the complement system acts on pathogens and not host tissue. Factor H circulates in human plasma at a concentration of 500-800 micrograms per milliliter, binding to specific glycosaminoglycans (GAGs) present on human, but not most pathogenic, cell surfaces. Once located to self-cells and tissues, Factor H down-regulates complement activation through Factor I cofactor activity of C3b cleavage and decay accelerating activity against the alternative pathway C3 convertase, C3bBb.

Factor H is implicated as a potential therapeutic agent for several human disease states, including age-related macular degeneration (AMD), hemolytic uremic syndrome (aHUS) and membranoproliferative glomerulonephritis (MPGN). However, because of the extremely high worldwide demand for plasma-derived pooled immunoglobulin G (IgG), source plasma is not readily available for the direct isolation of Factor H. Rather, methods for Factor H isolation that can be introduced into existing IgG manufacturing schemes are needed. Several methods have been suggested to achieve just this, however, many of these proposed solutions require modification of the existing manufacturing scheme for established products. Such changes will require new regulatory approvals for the established products and may even result in alterations of the characteristics of the established products.

WO 2007/066017 describes a method for the production of Factor H preparations from cryo-poor plasma. Cryo-poor plasma, however, is a common source material for the manufacture of many commercially important IgG therapeutics, such as GAMMAGARD® LIQUID (Baxter Healthcare Corporation). WO 2007/06617 provides no guidance as to how the disclosed method, which involves passing cryo-poor plasma through at least two chromatographic steps, including anion exchange chromatography and heparin affinity chromatography, would impact, or even allow for, the manufacture IgG from the pre-processed cryo-poor plasma. In addition to requiring a complete revalidation and possible redesign of key IgG manufacturing processes, regulatory re-approval of the manufacturing procedures from key regulatory agencies would be required.

Likewise, WO 2008/113589 describes methods for the production of Factor H preparations from known plasma fractionation intermediates, namely Cohn-Oncley Fraction I supernatant, Cohn-Oncley Fraction II+III precipitate, and Kistler/Nitschmann Precipitate B fractions. Because these fractions are intermediates used in many commercially important IgG therapeutics, such as GAMMAGARD® LIQUID, implementation of these methods would likewise greatly impact existing IgG manufacturing capabilities.

U.S. Pat. No. 8,304,524 discloses methods for the isolation of Factor H from commonly produced by-products of IgG manufacturing processes, including Cohn Fraction I precipitate and Fraction II+III precipitate insoluble materials which are normally discarded. The '524 patent reports that about 90% of the Factor H content of plasma is fractionated into Cohn Fraction II+III precipitate during IgG manufacturing, and proposes that Factor H manufacturing efforts be focused on the extraction of Factor H from this by-product. However, Fraction II+III precipitate, and specifically the insoluble material derived therefrom and used in the '534 patent for the isolation of Factor H, contains high levels of proteolytic/amidolytic activity. It is shown herein that Factor H purified from Fraction II+III precipitate according to the methods of the '524 patent is proteolytically clipped to a large extent.

Brandstätter et al. (Vox Sanguinis (2012) 103, 201-212) report the purification of Factor H from an undisclosed plasma fraction. As in the '524 patent, Brandstätter et al. observe a large fraction of proteolytically clipped Factor H in their starting plasma fraction (see, lane 1 of the western blot shown in FIG. 3(b)).

Concerns over the amidolytic activity content of immunoglobulin compositions fueled by occurrences of thromboembolic events in patients being administered plasma-derived immunoglobulins and the recent withdrawal of two plasma-derived immunoglobulin compositions from market have highlighted a need for methods of effectively reducing serine proteases (e.g., activated protein C, kallikreins, FXIa, and FXIIa) during the manufacturing of plasma-derived therapeutics. Moreover, several studies have suggested that administration of high levels of amidolytic activity may result in unwanted thromboembolic events (Wolberg A S et al., Coagulation factor XI is a contaminant in intravenous immunoglobulin preparations. Am J Hematol 2000; 65:30-34; and Alving B M et al., Contact-activated factors: contaminants of immunoglobulin preparations with coagulant and vasoactive properties. J Lab Clin Med 1980; 96:334-346).

Thus, a need remains for methods of manufacturing plasma-derived Factor H compositions with reduced proteolytic profiles from the existing supply of plasma donations. Advantageously, the present disclosure fulfills these and other needs by providing improved methods that reduce the proteolytic content (e.g., amidolytic activity) of Factor H compositions prepared from precipitation byproducts normally discarded during the manufacture of commercial IgG therapeutic products.

BRIEF SUMMARY OF INVENTION

Among other aspects, the present disclosure provides methods for preparing enriched compositions of plasma-derived Factor H from fractions formed during established IgG manufacturing processes. Specifically, methods are provided for the isolation of Factor H from Cohn Fraction I or equivalent precipitates (e.g., a Kistler-Nitschmann Fraction I) and Cohn Fraction II+III or equivalent precipitates (e.g., a Kistler-Nitschmann precipitate A) commonly discarded during the manufacture of commercial IgG therapeutics such as GAMMAGARD® LIQUID. Use of previously discarded plasma fractions eliminates the need to allocate a portion of the limited worldwide plasma resources, provided through donations, to dedicated Factor H manufacturing processes. Advantageously, several purification steps were identified that significantly reduce the amidolytic activity and proteolytic clipping of Factor H purified from Fraction II+III silicon dioxide filter cakes. Although identified in the context of enrichment from Fraction II+III silicon dioxide filter cake, these methods can also be applied to purification processes starting from other plasma precipitates (e.g., Fraction I precipitates) or recombinant expression sources.

In some aspects, the disclosure provides a first method for preparing an enriched Factor H composition from plasma, the method including (A) precipitating Factor H from a Cohn plasma pool or Fraction I supernatant with alcohol, thereby forming a Factor H precipitate. The method further includes (B) suspending the Factor H precipitate in a suspension buffer, thereby forming a Factor H suspension. The method further includes (C) contacting the Factor H suspension with finely divided silicon dioxide ($SiO_2$). The method further includes (D) separating the Factor H suspension into a soluble fraction and an insoluble fraction. The method further includes (E) extracting Factor H from the insoluble fraction separated in step (D) with an extraction buffer comprising a conductivity of 15 to 24 mS/cm and a pH of 4.6 to 5.4, thereby forming a Factor H extract.

In some aspects, the disclosure provides a second method for preparing an enriched Factor H composition from plasma, the method including (A) precipitating Factor H from a Cohn plasma pool or Fraction I supernatant with alcohol, thereby forming a Factor H precipitate. The method further includes (B) suspending the Factor H precipitate in a suspension buffer, thereby forming a Factor H suspension. The method further includes (C) contacting the Factor H suspension with finely divided silicon dioxide ($SiO_2$). The method further includes (D) separating the Factor H suspension into a soluble fraction and an insoluble fraction. The further includes (E) extracting Factor H from the insoluble fraction separated in step (D) with an extraction buffer comprising a conductivity of 14 to 30 mS/cm and a pH of 5.3 to 5.8, thereby forming a Factor H extract.

Some embodiments of the first and second methods also include (F) admixing a sugar and/or sugar alcohol into the composition comprising Factor H to a final concentration of 2.5% to 10%.

Some embodiments of the first and second methods also include (G) incubating the composition comprising Factor H and the sugar and/or sugar alcohol at a temperature of 60° C. to 75° C. and a pH of 4.5 to 7.0 for 1 to 3 hours.

Some embodiments of the first and second methods also include (H) binding Factor H from the Factor H extract to an anion exchange resin using solution conditions comprising a conductivity of 2 mS/cm to 5 mS/cm and a pH of 6.4±0.3.

Some embodiments of the first and second methods also include (I) eluting Factor H from the anion exchange resin using solution conditions comprising either a conductivity of 20 mS/cm to 30 mS/cm and a pH of 6.0 to 7.5, or a conductivity of 10 mS/cm to 20 mS/cm and a pH of 7.5 to 8.5.

Some embodiments of the first and second methods also include (J) binding Factor H from the Factor H extract to heparin affinity resin using solution conditions comprising a conductivity of 7 mS/cm to 11 mS/cm and a pH of 7.2±0.3.

Some embodiments of the first and second methods also include (K) eluting Factor H from the heparin affinity resin using solution conditions comprising a conductivity of 25 mS/cm to 35 mS/cm and a pH of 8.0±0.3.

Some embodiments of the first and second methods also include (L) binding Factor H from the Factor H extract to a mixed mode chromatography resin comprising an aliphatic or aromatic ligand using solution conditions comprising a conductivity of 15 mS/cm to 40 mS/cm and a pH of 7.3±0.6.

Some embodiments of the first and second methods also include (M) washing the bound mixed mode chromatography resin with a wash buffer having a conductivity of 10 mS/cm to 50 mS/cm and a pH of 6.2 to 7.3.

Some embodiments of the first and second methods also include (N) eluting Factor H from the mixed mode chromatography resin using solution conditions comprising a conductivity of 4 mS/cm to 11 mS/cm and a pH of 4.3 to 5.0.

In some aspects, the disclosure provides a third method for reducing amidolytic activity in a Factor H composition, the method including providing a composition comprising Factor H. The method further includes (F) admixing a sugar and/or sugar alcohol into the composition comprising Factor H to a final concentration of 2.5% to 10%. The method further including (G) incubating the composition comprising Factor H and the sugar and/or sugar alcohol at a temperature of 60° C. to 75° C. and a pH of 4.5 to 7.0 for 1 to 3 hours.

Some embodiments of the third method also include (A) precipitating Factor H from a Cohn plasma pool or Fraction I supernatant with alcohol, thereby forming a Factor H precipitate.

Some embodiments of the third method also include (B) suspending the Factor H precipitate in a suspension buffer, thereby forming a Factor H suspension.

Some embodiments of the third method also include (C) contacting the Factor H suspension with finely divided silicon dioxide ($SiO_2$).

Some embodiments of the third method also include (D) separating the Factor H suspension into a soluble fraction and an insoluble fraction.

Some embodiments of the third method also include (E) extracting Factor H from the insoluble fraction separated in step (D) with an extraction buffer comprising a conductivity of 15 to 24 mS/cm and a pH of 4.6 to 5.4, thereby forming a Factor H extract.

Some embodiments of the third method also include (H) binding Factor H from the Factor H extract to an anion exchange resin using solution conditions comprising a conductivity of 2 mS/cm to 5 mS/cm and a pH of 6.4±0.3.

Some embodiments of the third method also include (I) eluting Factor H from the anion exchange resin using solution conditions comprising either a conductivity of 20 mS/cm to 30 mS/cm and a pH of 6.0 to 7.5, or a conductivity of 10 mS/cm to 20 mS/cm and a pH of 7.5 to 8.5.

Some embodiments of the third method also include (J) binding Factor H from the Factor H extract to heparin affinity resin using solution conditions comprising a conductivity of 7 mS/cm to 11 mS/cm and a pH of 7.2±0.3.

Some embodiments of the third method also include (K) eluting Factor H from the heparin affinity resin using solution conditions comprising a conductivity of 25 mS/cm to 35 mS/cm and a pH of 8.0±0.3.

Some embodiments of the third method also include (L) binding Factor H from the Factor H extract to a mixed mode chromatography resin comprising an aliphatic or aromatic ligand using solution conditions comprising a conductivity of 15 mS/cm to 40 mS/cm and a pH of 7.3±0.6.

Some embodiments of the third method also include (M) washing the bound mixed mode chromatography resin with a wash buffer having a conductivity of 10 mS/cm to 50 mS/cm and a pH of 6.2 to 7.3.

Some embodiments of the third method also include (N) eluting Factor H from the mixed mode chromatography resin using solution conditions comprising a conductivity of 4 mS/cm to 11 mS/cm and a pH of 4.3 to 5.0.

In some aspects, the disclosure provides a fourth method for preparing an enriched Factor H composition from plasma, the method including (A) precipitating Factor H from a Cohn plasma pool or Fraction I supernatant with alcohol, thereby forming a Factor H precipitate. The method further including (E) extracting Factor H from the Factor H precipitate, thereby forming a Factor H extract. The method further including (H) binding Factor H from the Factor H extract to an anion exchange resin using solution conditions comprising a conductivity of 2 mS/cm to 5 mS/cm and a pH of 6.4±0.3. The method further including (I) eluting Factor H from the anion exchange resin using solution conditions comprising either a conductivity of 20 mS/cm to 30 mS/cm and a pH of 6.0 to 7.5, or a conductivity of 10 mS/cm to 20 mS/cm and a pH of 7.5 to 8.5.

Some embodiments of the fourth method also include (B) suspending the Factor H precipitate in a suspension buffer, thereby forming a Factor H suspension.

Some embodiments of the fourth method also include (C) contacting the Factor H suspension with finely divided silicon dioxide ($SiO_2$).

Some embodiments of the fourth method also include (D) separating the Factor H suspension into a soluble fraction and an insoluble fraction.

Some embodiments of the fourth method also include (E) extracting Factor H from the insoluble fraction separated in step (D) with an extraction buffer comprising a conductivity of 15 to 24 mS/cm and a pH of 4.6 to 5.4, thereby forming a Factor H extract.

Some embodiments of the fourth method also include (F) admixing a sugar and/or sugar alcohol into the composition comprising Factor H to a final concentration of 2.5% to 10%.

Some embodiments of the fourth method also include (G) incubating the composition comprising Factor H and the sugar and/or sugar alcohol at a temperature of 60° C. to 75° C. and a pH of 4.5 to 7.0 for 1 to 3 hours.

Some embodiments of the fourth method also include (J) binding Factor H from the Factor H extract to heparin affinity resin using solution conditions comprising a conductivity of 7 mS/cm to 11 mS/cm and a pH of 7.2±0.3.

Some embodiments of the fourth method also include (K) eluting Factor H from the heparin affinity resin using solution conditions comprising a conductivity of 25 mS/cm to 35 mS/cm and a pH of 8.0±0.3.

Some embodiments of the fourth method also include (L) binding Factor H from the Factor H extract to a mixed mode chromatography resin comprising an aliphatic or aromatic ligand using solution conditions comprising a conductivity of 15 mS/cm to 40 mS/cm and a pH of 7.3±0.6.

Some embodiments of the fourth method also include (M) washing the bound mixed mode chromatography resin with a wash buffer having a conductivity of 10 mS/cm to 50 mS/cm and a pH of 6.2 to 7.3.

Some embodiments of the fourth method also include (N) eluting Factor H from the mixed mode chromatography resin using solution conditions comprising a conductivity of 4 mS/cm to 11 mS/cm and a pH of 4.3 to 5.0.

In some aspects, the disclosure provides a fifth method for preparing an enriched Factor H composition from plasma, the method including (A) precipitating Factor H from a Cohn plasma pool or Fraction I supernatant with alcohol, thereby forming a Factor H precipitate. The method further including (E) extracting Factor H from the Factor H precipitate, thereby forming a Factor H extract. The method further including (J) binding Factor H from the Factor H extract to heparin affinity resin using solution conditions comprising a conductivity of 7 mS/cm to 11 mS/cm and a pH of 7.2±0.3. The method further including (K) eluting Factor H from the heparin affinity resin using solution conditions comprising a conductivity of 25 mS/cm to 35 mS/cm and a pH of 8.0±0.3.

Some embodiments of the fifth method also include (B) suspending the Factor H precipitate in a suspension buffer, thereby forming a Factor H suspension.

Some embodiments of the fifth method also include (C) contacting the Factor H suspension with finely divided silicon dioxide ($SiO_2$).

Some embodiments of the fifth method also include (D) separating the Factor H suspension into a soluble fraction and an insoluble fraction.

Some embodiments of the fifth method also include (E) extracting Factor H from the insoluble fraction separated in step (D) with an extraction buffer comprising a conductivity of 15 to 24 mS/cm and a pH of 4.6 to 5.4, thereby forming a Factor H extract.

Some embodiments of the fifth method also include (F) admixing a sugar and/or sugar alcohol into the composition comprising Factor H to a final concentration of 2.5% to 10%.

Some embodiments of the fifth method also include (G) incubating the composition comprising Factor H and the sugar and/or sugar alcohol at a temperature of 60° C. to 75° C. and a pH of 4.5 to 7.0 for 1 to 3 hours.

Some embodiments of the fifth method also include (H) binding Factor H from the Factor H extract to an anion exchange resin using solution conditions comprising a conductivity of 2 mS/cm to 5 mS/cm and a pH of 6.4±0.3.

Some embodiments of the fifth method also include (I) eluting Factor H from the anion exchange resin using solution conditions comprising either a conductivity of 20 mS/cm to 30 mS/cm and a pH of 6.0 to 7.5, or a conductivity of 10 mS/cm to 20 mS/cm and a pH of 7.5 to 8.5.

Some embodiments of the fifth method also include (L) binding Factor H from the Factor H extract to a mixed mode chromatography resin comprising an aliphatic or aromatic ligand using solution conditions comprising a conductivity of 15 mS/cm to 40 mS/cm and a pH of 7.3±0.6.

Some embodiments of the fifth method also include (M) washing the bound mixed mode chromatography resin with a wash buffer having a conductivity of 10 mS/cm to 50 mS/cm and a pH of 6.2 to 7.3.

Some embodiments of the fifth method also include (N) eluting Factor H from the mixed mode chromatography resin using solution conditions comprising a conductivity of 4 mS/cm to 11 mS/cm and a pH of 4.3 to 5.0.

In some aspects, the disclosure provides a sixth method for preparing an enriched Factor H composition from plasma, the method including (A) precipitating Factor H from a Cohn plasma pool or Fraction I supernatant with alcohol, thereby forming a Factor H precipitate. The method further including (E) extracting Factor H from the Factor H precipitate, thereby forming a Factor H extract. The method further including (L) binding Factor H from the Factor H extract to a mixed mode chromatography resin comprising an aliphatic or aromatic ligand using solution conditions comprising a conductivity of 15 mS/cm to 40 mS/cm and a pH of 7.3±0.6. The method further including (N) eluting Factor H from the mixed mode chromatography resin using solution conditions comprising a conductivity of 4 mS/cm to 11 mS/cm and a pH of 4.3 to 5.0.

Some embodiments of the sixth method also include (B) suspending the Factor H precipitate in a suspension buffer, thereby forming a Factor H suspension.

Some embodiments of the sixth method also include (C) contacting the Factor H suspension with finely divided silicon dioxide ($SiO_2$).

Some embodiments of the sixth method also include (D) separating the Factor H suspension into a soluble fraction and an insoluble fraction.

Some embodiments of the sixth method also include (E) extracting Factor H from the insoluble fraction separated in step (D) with an extraction buffer comprising a conductivity of 15 to 24 mS/cm and a pH of 4.6 to 5.4, thereby forming a Factor H extract.

Some embodiments of the sixth method also include (F) admixing a sugar and/or sugar alcohol into the composition comprising Factor H to a final concentration of 2.5% to 10%.

Some embodiments of the sixth method also include (G) incubating the composition comprising Factor H and the sugar and/or sugar alcohol at a temperature of 60° C. to 75° C. and a pH of 4.5 to 7.0 for 1 to 3 hours.

Some embodiments of the sixth method also include (H) binding Factor H from the Factor H extract to an anion exchange resin using solution conditions comprising a conductivity of 2 mS/cm to 5 mS/cm and a pH of 6.4±0.3.

Some embodiments of the sixth method also include (I) eluting Factor H from the anion exchange resin using solution conditions comprising either a conductivity of 20 mS/cm to 30 mS/cm and a pH of 6.0 to 7.5, or a conductivity of 10 mS/cm to 20 mS/cm and a pH of 7.5 to 8.5.

Some embodiments of the sixth method also include (J) binding Factor H from the Factor H extract to heparin affinity resin using solution conditions comprising a conductivity of 7 mS/cm to 11 mS/cm and a pH of 7.2±0.3.

Some embodiments of the sixth method also include (K) eluting Factor H from the heparin affinity resin using solution conditions comprising a conductivity of 25 mS/cm to 35 mS/cm and a pH of 8.0±0.3.

Some embodiments of the sixth method also include (M) washing the bound mixed mode chromatography resin with a wash buffer having a conductivity of 10 mS/cm to 50 mS/cm and a pH of 6.2 to 7.3.

In some embodiments of the methods provided above, Factor H is precipitated from a Cohn plasma pool in step (A).

In some embodiments of the methods provided above, Factor H is precipitated from a Fraction I supernatant in step (A).

In some embodiments of the methods provided above, precipitating (A) includes incubating the Cohn plasma pool or Fraction I supernatant after addition of alcohol to a final concentration of 17% to 27% at a pH of 5.5 to 7.0.

In some embodiments of the methods provided above, the Cohn plasma pool or Fraction I supernatant is incubated after addition of alcohol to a final concentration of 20% to 25% at a pH of 6.5 to 7.0.

In some embodiments of the methods provided above, the alcohol is ethanol.

In some embodiments of the methods provided above, the ethanol is denatured ethanol.

In some embodiments of the methods provided above, the Factor H precipitate is suspended in step (B) with a suspension buffer having a pH of 4.0 to 6.0 and a conductivity of 0.5 mS/cm to 2.0 mS/cm.

In some embodiments of the methods provided above, the Factor H suspension is contacted in step (C) with 5 g $SiO2$/kg suspended Factor H precipitate to 200 g $SiO_2$/kg suspended Factor H precipitate.

In some embodiments of the methods provided above, the insoluble fraction of the $SiO_2$ treated Factor H suspension is separated in step (D) by centrifugation.

In some embodiments of the methods provided above, the insoluble fraction of the $SiO_2$ treated Factor H suspension is separated in step (D) by filtration In some embodiments of the methods provided above, the filtration in step (D) is performed in a filter press and Factor H is extracted in step (E) by circulating an extraction buffer through the filter press containing the separated insoluble fraction.

In some embodiments of the methods provided above, Factor H is extracted in step (E) by suspending the insoluble fraction in extraction buffer.

In some embodiments of the methods provided above, the insoluble fraction is suspended in 3 to 10 volumes (v/w) extraction buffer.

In some embodiments of the methods provided above, the extraction buffer has a conductivity of 19±2 mS/cm.

In some embodiments of the methods provided above, the extraction buffer has a pH of 5.0±0.2.

In some embodiments of the methods provided above, the extraction buffer consists essentially of 50±10 mM sodium citrate (pH 5.0±0.2) and 75±15 mM sodium chloride In some embodiments of the methods provided above, the sugar, sugar alcohol, or combination thereof in (F) is sucrose, glucose, sorbitol, or a combination thereof.

In some embodiments of the methods provided above, the sugar, sugar alcohol, or combination thereof in (F) is sucrose.

In some embodiments of the methods provided above, the sugar, sugar alcohol, or combination thereof in (F) is glucose.

In some embodiments of the methods provided above, the sugar, sugar alcohol, or combination thereof in (F) is sorbitol.

In some embodiments of the methods provided above, the final concentration of the sugar, sugar alcohol, or combination thereof is 5±1%.

In some embodiments of the methods provided above, the composition in step (F) is incubated at a temperature of 68±3° C.

In some embodiments of the methods provided above, the composition in step (F) is incubated for about 2 hours.

In some embodiments of the methods provided above, the mixed mode resin includes an aliphatic ligand.

In some embodiments of the methods provided above, the mixed mode resin includes an aromatic ligand.

In some embodiments of the methods provided above, Factor H is bound to the mixed mode chromatography resin in step (L) using solution conditions having a conductivity of 24±9 mS/cm.

In some embodiments of the methods provided above, Factor H is bound to the mixed mode chromatography resin in step (L) using solution conditions having a conductivity of 24±6 mS/cm.

In some embodiments of the methods provided above, Factor H is bound to the mixed mode chromatography resin in step (L) using solution conditions having a conductivity of 26±7 mS/cm.

In some embodiments of the methods provided above, Factor H is bound to the mixed mode chromatography resin in step (L) using solution conditions having a conductivity of 26±4 mS/cm.

In some embodiments of the methods provided above, Factor H is bound to the mixed mode chromatography resin in step (L) using solution conditions having a pH of 7.4±3 mS/cm.

In some embodiments of the methods provided above, Factor H is bound to the mixed mode chromatography resin in step (L) using solution conditions having a pH of 7.2±3 mS/cm.

In some embodiments of the methods provided above, the wash buffer in (M) has a conductivity of 15±3 mS/cm.

In some embodiments of the methods provided above, the wash buffer in (M) has a conductivity of 15±1 mS/cm.

In some embodiments of the methods provided above, the wash buffer in (M) has a conductivity of 30 mS/cm to 45 mS/cm.

In some embodiments of the methods provided above, the wash buffer in (M) has a conductivity of 35 mS/cm to 40 mS/cm.

In some embodiments of the methods provided above, the wash buffer in (M) has a pH of 6.2 to 6.7.

In some embodiments of the methods provided above, the wash buffer in (M) has a pH of 6.4 to 6.5.

In some embodiments of the methods provided above, the wash buffer in (M) has a pH of 6.7 to 7.3.

In some embodiments of the methods provided above, the wash buffer in (M) has a pH of 6.9 to 7.1.

In some embodiments of the methods provided above, Factor H is eluted from the mixed mode chromatography resin in step (N) using solution conditions having a conductivity of 7 mS/cm to 10 mS/cm.

In some embodiments of the methods provided above, Factor H is eluted from the mixed mode chromatography resin in step (N) using solution conditions having a conductivity of 8 mS/cm to 9 mS/cm.

In some embodiments of the methods provided above, Factor H is eluted from the mixed mode chromatography resin in step (N) using solution conditions having a conductivity of 5 mS/cm to 8 mS/cm.

In some embodiments of the methods provided above, Factor H is eluted from the mixed mode chromatography resin in step (N) using solution conditions having a conductivity of 6 mS/cm to 7 mS/cm.

In some embodiments of the methods provided above, Factor H is eluted from the mixed mode chromatography resin in step (N) using solution conditions having a pH of 4.4±0.1.

In some embodiments of the methods provided above, Factor H is eluted from the mixed mode chromatography resin in step (N) using solution conditions having a pH of 4.3 to 4.8.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 10A illustrates extraction of Factor H (mg Factor H/L plasma; as measured by anti-Factor H ELISA after filtration) as a function of conductivity (y-axis) and pH (x-axis). FIG. 10B illustrates extraction of CS-2166 amidolytic activity (nmol*min total) as a function of conductivity (y-axis) and pH (x-axis). CS-2166 is a substrate for activated protein C and FXIa proteolysis. FIG. 10C illustrates extraction of CS-3102 amidolytic activity (nmol*min total) as a function of conductivity (y-axis) and pH (x-axis). CS-3102 is a substrate for Kallikren and FXIa proteolysis.

FIG. 14 shows the results of amidolytic activity assays performed for Factor H compositions prepared from Fraction II+III silicon dioxide filter cake according to the prior method described in Example 1 (FH012) and the improved method described in Example 16 (FH184).

FIG. 15 shows the results of lipopolysaccharide (LAL) analysis of various steps in the improved Factor H purification method described in Example 16.

DETAILED DESCRIPTION OF INVENTION

I. Introduction

The present disclosure is based in part on the discovery that Factor H can be extracted from Fraction II+III silicon dioxide filter cake under conditions that limit the co-extraction of amidolytic proteases responsible for proteolytic clipping of Factor H. By reducing the amount of proteolytic activity extracted from the starting material, Factor H remains to a higher degree intact (e.g., in the unclipped form) Thus providing Factor H composition with higher intactness and lower amidolytic activity.

For example, as shown in Example 7, it was found that the extraction profile of Factor H depends quite differently upon pH and conductivity than does the extraction profile of amidolytic activities, including activated C protein, kallikrein, Factor XIa, and Factor XIIa. While the extraction profile of Factor H depends fairly equally on both pH and conductivity, resulting in the horizontal pattern of maximum extraction in FIG. 10A, the extraction of amidolytic activity depends much more heavily upon pH than it does on conductivity. These finding are applied to provide improved conditions for extracting Factor H, e.g., specific combinations of pH and conductivity where Factor H is readily extracted, but amidolytic activities are not.

The present disclosure is also based in part on the discovery that Factor H formulated under specific conditions is capable of withstanding high temperature heat treatments. Advantageously, these heat treatments are effective for inactivating greater than 95% of the amidolytic activity in the Factor H composition. Thus, when paired with the improved Fraction II+III extraction methods described herein, Factor H compositions with low proteolytic clipping (e.g., less than 20% clipping) can be prepared from Fraction II+III silicon dioxide filter cakes. Furthermore, the discovery that Factor H compositions can be stabilized to withstand high temperatures for extended periods of time in solution, allows methods for treating other Factor H compositions, e.g., Factor H compositions prepared from Fraction I precipitates or recombinant Factor H to remove or inactivate impurities unique to the respective starting material. For example, host cell proteins and/or enzymatic activities in recombinant Factor H compositions can be reduced by heat treatment.

Figure 12:
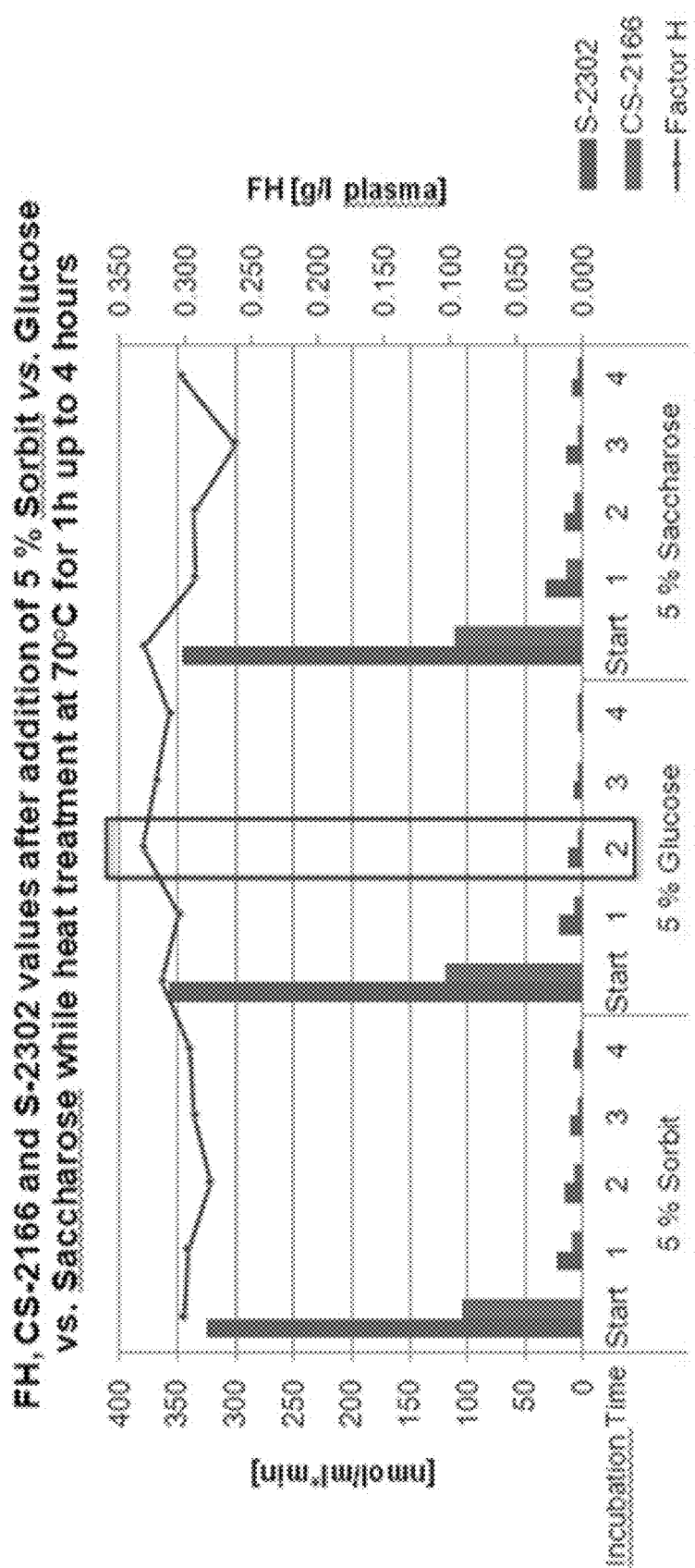
FIG. 12 illustrates Factor H concentrations (µg/mL), CS-2166 amidolytic activity (activated protein C and Factor XIa; nmol/mL*min), and S2303 (Kallikrein, Factor XIIa, and Factor XIa; nmol/mL*min) of Factor H samples prepared according to Example 16 after heat treatment performed at 70° C. for 1, 2, 3, or 4 hours in the presence of 5% sorbitol ("Sorbit"), glucose, or sucrose ("Saccharose").

For example, as demonstrated in Example 11, Factor H is substantially stabilized upon the addition of 2.5% to 7.5% of a sugar and/or sugar alcohol stabilizer (e.g., glucose, sorbitol, and/or sucrose). Advantageously, while these additives stabilize Factor H, amidolytic activity is significantly reduced upon treatment at high temperature (e.g., 60-75° C.). As can be seen in FIG. 12, amidolytic activities with specificities for S-2302 (e.g., activated protein C and FXIa) and CS-2166 (e.g., Kallikrein and Factor FXIIa) are reduced by greater than 95% after two hours of incubation at 70° C. in all Factor H formulations.

The present disclosure is also based in part on the discovery of chromatographic conditions that provide improved enrichment of Factor H. In some embodiments, these chromatographic conditions include anion exchange chromatography, heparin affinity chromatography, and/or mixed mode chromatography, e.g., using an aliphatic or aromatic ligand. For example, it is shown in Example 18 that the combination of these three chromatographic steps significantly reduces the content of lipopolysaccharides in Factor H compositions extracted from Fraction II+III silicon dioxide filter cake.

Taken together, the improved process steps identified here allow for the manufacture of Factor H compositions with improved proteolytic profiles, reduced amidolytic activity, greater purity, and higher biochemical activity than existing methods for the enrichment of Factor H from Fraction II+III silicon dioxide filter cake. For example, characterization in Example 18 of a Factor H composition purified in larger-scale from 10 kg of a Fraction II+III silicon dioxide filter cake shows undetectable levels of amidolytic activity, thrombin generation activity (TGA) levels near those of normal human plasma, and PKKA activities within the specifications set forth in the European Pharmacopoeia for plasma-derived albumin compositions. Moreover, as demonstrated in Example 19, this Factor H composition has biochemical activities, including decay acceleration (DAF) activity and Factor I co-factor activities that are comparable or better than activities seen in commercially available Factor H standards.

II. Definitions

As used herein, "Factor H" refers to a protein component of the alternative pathway of complement encoded by the complement factor H gene (for example, CFH; NM000186; GeneID:3075; UniProt ID P08603; Ripoche et al., Biochem. J. 249:593-602(1988)). Factor H is translated as a 1,213 amino acid precursor polypeptide which is processed by removal of an 18 amino acid signal peptide, resulting in the mature Factor H protein (amino acids 19-1231). As used herein, Factor H encompasses any natural variants, alternative sequences, isoforms or mutant proteins that can be found in a plasma sample, for example a human plasma sample. Examples of Factor H mutations found in the human population include, without limitation, Y402H; V62I; R78G; R127L; Δ224; Q400K; C431S; T493R; C536R; I551T; R567G; C630W; C673S; C673Y; E850K; S890I; H893R; C915S; E936D; Q950H; Y951H; T956M; C959Y; W978C; N997T; V1007I; V1007L; A1010T; T1017I; Y1021F; C1043R; N1050Y; I1059T; Q1076R; R1078S; D1119G; V1134G; Y1142D; Q1143E; W1157R; C1163W; W1183L; W1183R; T1184R; L1189R; S1191L; G1194D; V1197A; E1198A; F1199S; R1210C; R1215G; R1215Q; YPTCAKR1225:1231FQS; and P1226S. Many of the these mutations have been found to be associated with a variety of diseases and disorders, including, atypical haemolytic uremic syndrome (aHUS), age-related macular degeneration (AMD), membranoproliferative glomulonephritis type II (MPGNII), CFH deficiency, and basal laminar drusen. Factor H also includes proteins containing post-translational modifications. For example, Factor H is believed to be modified by N-acetylglucosamine (GlcNAc) at residues 529, 718, 802, 822, 882, 911, 1029, and 1095.

The methods of the present invention include the use of compositions comprising Factor H. Unless otherwise specified, the term "Factor H" or "FH" as used herein refers to both plasma-derived and recombinant Factor H. Variants of plasma-derived Factor H and methods for producing plasma-derived Factor H are known in the art and are described for example in WO 2007/149567, WO 2007/066017, WO 2008/113589, WO 2011/011753, and U.S. Pat. No. 7,745,389, each of which is hereby incorporated by reference in its entirety for all purposes and in particular for all teachings related to the production of Factor H, particularly plasma-derived Factor H. A wide variety of Factor H polymorphisms are known in the art and described for example in WO 2000/52479, WO 2006/062716, U.S. Pat. No. 7,351,524, and U.S. Pat. No. 7,745,389 (each which is herein incorporated by reference in its entirety for all purposes and in particular for all teachings related to Factor H and variants of Factor H), which also describe recombinant forms of these Factor H polypeptides and methods for producing the same.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

As used herein, the term "enriched composition" refers to a protein composition isolated from a plasma sample or cell culture supernatant, in which the purity of the protein is higher than the purity of the protein in the starting sample (e.g., pooled plasma or cell culture supernatant). In one embodiment, a protein in an enriched composition is at least 25% more pure than in the starting plasma sample. In other embodiments, an enriched composition is at least 50%, 75%, 100%, 2-fold, 3-fold, 4-fold, 5-fold, 6-fold, 7-fold, 8-fold, 9-fold, 10-fold, or more pure than the starting plasma sample. For example, an enriched Factor H composition in which 70% of the total protein is Factor H is 7-fold enriched as compared to a starting sample in which 10% of the total protein is Factor H.

As used herein, the term "cryo-poor plasma" refers to a supernatant formed by cryo-precipitation of blood plasma (e.g., plasma from a single source or a pool of plasma from multiple sources). Cryo-precipitation is typically performed by thawing frozen plasma a temperature near freezing, e.g., at a temperature below about 10° C., preferably at a temperature no higher than about 6° C. As used herein "plasma," unless otherwise specified, refers to both recovered plasma (i.e., plasma that has been separated from whole blood ex vivo) or source plasma (i.e., plasma collected via plasmapheresis). Although cryo-precipitation is commonly performed by thawing previously frozen plasma (e.g., pooled plasma) which has already been assayed for safety and quality considerations, in some embodiments, fresh plasma may also be used. After complete thawing of the frozen plasma at low temperature, the solid cryo-precipitates are separated from the liquid supernatant (i.e., the "cryo-poor plasma") in the cold (e.g., at a temperature below about 10° C., preferably no more than 6° C.) by centrifugation, filtration, or other suitable means.

As used herein, a "Cohn pool" or "Cohn plasma pool" refers to the starting material used for the fractionation of a plasma sample or pool of plasma samples. Cohn pools include, without limitation, whole plasma, cryo-poor plasma, and pools of whole plasma, cryo-poor plasma, or a combination thereof. In some embodiments, a Cohn pool is subjected to a pre-processing step. In certain embodiments, a Cohn pool is a cryo-poor plasma sample from which one or more blood factor have been removed in a pre-processing step, for example, adsorption onto a solid phase (e.g., aluminum hydroxide or finely divided silicon dioxide) or chromatographic step (e.g., ion exchange or heparin affinity chromatography). Various blood factors, including but not limited to, Factor Eight Inhibitor Bypass Activity (FEIBA), Factor IX-complex, Factor VII-concentrate, or Antithrombin III-complex, may be isolated from the cryo-poor plasma sample prior to use as a Cohn pool for isolation of Factor H.

As used herein, a "Fraction I precipitate" refers to a precipitate formed by cold incubation of blood plasma or a derivative thereof (e.g., cryo-poor plasma) after the addition of alcohol (e.g., denatured ethanol) to a final concentration of from about 6% to about 10% (v/v) at a pH of from about 7.0 to about 7.5, and encompasses common intermediates formed during Cohn-Oncley (Cohn et al., J. Am. Chem. Soc. 68:459-75 (1946); Oncley et al., J. Am. Chem. Soc. 71:541-50 (1949), the disclosures of which are hereby expressly incorporated by reference in their entireties for all purposes) and Kistler-Nitschmann (Kistler and Nitschmann, Vox Sang. 7:414-424 (1962), the disclosure of which is hereby expressly incorporated by reference in its entirety for all purposes) alcohol fractionations, and derivative fractionation schemes thereof.

As used herein, a "Fraction II+III precipitate" refers to a precipitate formed by cold incubation of blood plasma or a derivative thereof (e.g., cryo-poor plasma or Fraction I supernatant) after the addition of alcohol (e.g., denatured ethanol) to a final concentration of from about 17% to about 27% (v/v) at a pH of from about 5.5 to about 7.0, and encompasses common intermediates formed during Cohn-Oncley (e.g., Fraction II+III; Cohn et al., J. Am. Chem. Soc. 68:459-75 (1946); Oncley et al., J. Am. Chem. Soc. 71:541-50 (1949), the disclosures of which are hereby expressly incorporated by reference in their entireties for all purposes) and Kistler-Nitschmann (e.g., Precipitate A; Kistler and Nitschmann, Vox Sang. 7:414-424 (1962), the disclosure of which is hereby expressly incorporated by reference in its entirety for all purposes) alcohol fractionations, and derivative fractionation schemes thereof.

In some embodiments, a "Cohn Fraction II+III precipitate" refers to a precipitate formed by cold incubation of blood plasma or a derivative thereof (e.g., cryo-poor plasma of Fraction I supernatant) after the addition of alcohol (e.g., denatured ethanol) to a final concentration of from about 17% to about 27% (v/v), preferably from about 20% to 25% (v/v) at a pH of from about 6.5 to about 7.0, and encompasses common intermediates formed during Cohn-Oncley (e.g., Fraction II+III; Cohn et al., J. Am. Chem. Soc. 68:459-75 (1946); Oncley et al., J. Am. Chem. Soc. 71:541-50 (1949), the disclosures of which are hereby expressly incorporated by reference in their entireties for all purposes) alcohol fractionation, and derivative fractionation schemes thereof.

In some embodiments, a "Kistler-Nitschmann II+III precipitate" refers to a precipitate formed by cold incubation of blood plasma or a derivative thereof (e.g., cryo-poor plasma or Supernatant B) after the addition of alcohol (e.g., denatured ethanol) to a final concentration of from about 17% to about 22% (v/v) at a pH of from about 5.5 to about 6.0, and encompasses common intermediates formed during Kistler-Nitschmann (e.g., Precipitate A; Kistler and Nitschmann, Vox Sang. 7:414-424 (1962), the disclosure of which is hereby expressly incorporated by reference in its entirety for all purposes) alcohol fractionation, and derivative fractionation schemes thereof.

As used herein, a "Fraction II+III silicon dioxide filter cake" refers to a product formed by treating a suspension of a Fraction II+III precipitate with silicon dioxide and separating the resulting insoluble fraction (e.g., containing the silicon dioxide) from the resulting supernatant (e.g., generally containing IgG). Separation of the respective soluble and insoluble fractions is achieved by filtration, centrifugation, or any other means known in the art for separating insoluble material from a supernatant. In some embodiments, separation is achieved by passing the treated Fraction II+III precipitate suspension through a filter press containing one or more filter elements.

As used herein, the term "alcohol" refers to a $C_1$-$C_5$ monohydric alcohol capable of precipitating proteins from plasma. In some embodiments, the alcohol is ethanol or methanol. In a preferred embodiment, the alcohol is ethanol. In some embodiments, the ethanol is denatured (e.g., "denatured ethanol" or "denatured alcohol") by addition of methanol or methyl-ethyl-ketone (e.g., ethanol SDA 3A containing approximately 95% ethanol and 5% methanol (w/w)). In some embodiments, the alcohol concentrations used for precipitation reactions disclosed herein refer to a final concentration of a denatured ethanol. The skilled artisan will understand how to adapt these percentages to optimize a precipitation reaction when using a different alcohol, such as methanol.

As used herein, the term "ultrafiltration (UF)" encompasses a variety of membrane filtration methods which are typically performed in a tangential flow filtration mode. Suspended solids and solutes of high molecular weight are retained, while water and low molecular weight solutes pass through the membrane. This separation process is often used for purifying and concentrating macromolecular (103-106 Da) solutions, especially protein solutions. A number of ultrafiltration membranes are available depending on the size of the molecules they retain. Ultrafiltration is typically characterized by a membrane pore size between 1 and 1000 kDa and operating pressures between 0.01 and 10 bar.

As used herein, the term "diafiltration" is performed with the same or a similar membrane as ultrafiltration and is typically performed in a tangential flow filtration mode. During diafiltration, buffer is introduced into the recycle tank while filtrate is removed from the unit operation. In processes where the product is in the retentate (for example, Factor H), diafiltration is particularly useful for separating protein from small molecules like sugars and salts. In certain cases, diafiltration can be used to exchange the solution, buffer, or individual components of a buffering system.

As used herein, the term "about" denotes an approximate range of plus or minus 10% from a specified value. For instance, the language "about 20%" encompasses a range of 18-22%.

As used herein, the term "mixing" describes an act of causing equal distribution of two or more distinct compounds or substances in a solution or suspension by any form of agitation. Complete equal distribution of all ingredients in a solution or suspension is not required as a result of "mixing" as the term is used in this application.

As used herein, the term "solvent" encompasses any liquid substance capable of dissolving or dispersing one or more other substances. A solvent may be inorganic in nature, such as water, or it may be an organic liquid, such as ethanol, acetone, methyl acetate, ethyl acetate, hexane, petrol ether, etc. As used in the term "solvent detergent treatment," solvent denotes an organic solvent (e.g., tri-N-butyl phosphate), which is part of the solvent detergent mixture used to inactivate lipid-enveloped viruses in solution.

As used herein, the term "detergent" is used in this application interchangeably with the term "surfactant" or "surface acting agent." Surfactants are typically organic compounds that are amphiphilic, i.e., containing both hydrophobic groups ("tails") and hydrophilic groups ("heads"), which render surfactants soluble in both organic solvents and water. A surfactant can be classified by the presence of formally charged groups in its head. A non-ionic surfactant has no charge groups in its head, whereas an ionic surfactant carries a net charge in its head. A zwitterionic surfactant contains a head with two oppositely charged groups. Some examples of common surfactants include: Anionic (based on sulfate, sulfonate or carboxylate anions): perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate (also known as sodium lauryl ether sulfate, or SLES), alkyl benzene sulfonate; cationic (based on quaternary ammonium cations): cetyl trimethylammonium bromide (CTAB) a.k.a. hexadecyl trimethyl ammonium bromide, and other alkyltrimethylammonium salts, cetylpyridinium chloride (CPC), polyethoxylated tallow amine (POEA), benzalkonium chloride (BAC), benzethonium chloride (BZT); Long chain fatty acids and their salts: including caprylate, caprylic acid, heptanoat, hexanoic acid, heptanoic acid, nanoic acid, decanoic acid, and the like; Zwitterionic (amphoteric): dodecyl betaine; cocamidopropyl betaine; coco ampho glycinate; nonionic: alkyl poly(ethylene oxide), alkylphenol poly(ethylene oxide), copolymers of poly(ethylene oxide) and polypropylene oxide) (commercially known as Poloxamers or Poloxamines), alkyl polyglucosides, including octyl glucoside, decyl maltoside, fatty alcohols (e.g., cetyl alcohol and oleyl alcohol), cocamide MEA, cocamide DEA, polysorbates (Tween 20, Tween 80, etc.), Triton detergents, and dodecyl dimethylamine oxide.

As used herein, a "disease or disorder associated with Factor H dysfunction" refers to any disease, disorder, or condition in a subject that is caused by, characterized by, or results in a reduced level of Factor H activity in the subject. For purposes of the present invention, Factor H activity may refer to the ability of Factor H to bind a protein, protein complex, or ligand, for example, C3b, C3bBb, complement factor B (CFB), C-reactive protein, endothelial cells, glycosaminoglycans (GAGs), or alternatively, may refer to its Factor I cofactor activity or its ability to accelerate the irreversible dissociation of C3bBb. In one embodiment, a disease or disorder associated with Factor H dysfunction results in a C3 deficiency and susceptibility to bacterial infections. In some instances, diseases or disorders associated with Factor H dysfunction include conditions that are caused by or linked to mutations and polymorphism in the CFH gene encoding Factor H (for review, see, Barlow et al., Adv Exp Med Biol. 2008; 632:117-42, the disclosure of which is hereby expressly incorporated herein by reference in its entirety for all purposes). Diseases that have been linked to mutations or polymorphisms in the CFH gene include, without limitation, Factor H deficiency, atypical haemolytic uremic syndrome (aHUS), age-related macular degeneration (AMD), membranoproliferative glomulonephritis type II (MPGNII; de Cordoba and de Jorge, Clinical and Experimental Immunology 151, 1-13 (2008)), myocardial infarction (Kardys et al., Journal of the American College of Cardiology 47, 1568-1575 (2006); Mooijaart et al., Experimental Gerontology 42, 1116-1122 (2007); Nicaud et al., Journal of Molecular Medicine 85, 771-775 (2007); Pai et al., European Heart Journal 28, 1297-1303 (2007); Stark et al., Clinical Science (Lond) 113, 213-218 (2007)), coronary heart disease/coronary artery disease (CAD/CHD; (Meng et al., BMC Medical Genetics 8, 62 (2007); Pulido et al., Mayo Clinic Proceedings 82, 301-307 (2007); Topol et al., Human Molecular Genetics 15 Spec No 2, R117-R123 (2006)), and Alzheimer's disease (Hamilton et al., Neuromolecular Medicine 9, 331-334 (2007); Zetterberg et al., American Journal of Ophthalmology 143, 1059-1060 (2007)). The disclosures of the forgoing references describing the associations between mutations and polymorphisms in the CFH gene and diseases associated with Factor H dysfunction are herein incorporated by reference in their entireties for all purposes.

As used herein, a "disease or disorder associated with abnormal alternative pathway complement activity" refers to a disease, disorder, or condition that results from uncontrolled or aberrant activation of the alternative pathway of complement. Generally, uncontrolled or aberrant activation of the alternative pathway of complement can result in bystander damage of host cells and tissues, as well as a depletion of C3 and corresponding susceptibility to pathogenic infections (e.g., fungal, bacterial, viral, and protistal). Examples of diseases and disorders associated with abnormal alternative pathway complement activity include, without limitation, various autoimmune diseases (such as rheumatoid arthritis, IgA nephropathy, asthma, systemic lupus erythematosus, multiple sclerosis, Anti-Phospholipid syndrome, ANCA-associated vasculitis, pemphigus, uveitis, myathemia gravis, Hashimoto's thyroiditis), renal diseases (such as IgA nephropathy, hemolytic uremic syndrome, membranoproliferative glomerulonephritis) other disease such as asthma, Alzheimer disease, adult macular degeneration, proximal nocturnal hemoglobinuria, abdominal aortic aneurism, ischemia, and sepsis.

As used herein, the term "therapeutically effective amount or dose" or "sufficient/effective amount or dose," refers to a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins; the disclosures of which are hereby expressly incorporated herein by reference in their entireties for all purposes).

As used herein, the term "pharmaceutically acceptable" means that a substance which is useful in preparing a pharmaceutical composition is generally safe, non-toxic, and neither biologically nor otherwise undesirable when administered for human pharmaceutical and/or veterinary use.

III. Enrichment of Factor H

In some embodiments, an improved method for manufacturing an enriched Factor H composition from plasma is provided, the method including precipitating Factor H from a Cohn plasma pool or Fraction I supernatant with alcohol, to form a Factor H precipitate. The method also includes suspending the Factor H precipitate in a suspension buffer, contacting the resulting Factor H suspension with finely divided silicon dioxide ($SiO_2$), and separating the Factor H suspension into soluble and insoluble fractions. The method further includes extracting Factor H from the insoluble fraction with an extraction buffer having a conductivity of 15 to 24 mS/cm and a pH of 4.6 to 5.4 and enriching the Factor H extract with at least one chromatographic enrichment step.

In some embodiments, an improved method for manufacturing an enriched Factor H composition from plasma is provided, the method including precipitating Factor H from a Cohn plasma pool or Fraction I supernatant with alcohol, to form a Factor H precipitate. The method also includes suspending the Factor H precipitate in a suspension buffer, contacting the resulting Factor H suspension with finely divided silicon dioxide (SiO2), and separating the Factor H suspension into soluble and insoluble fractions. The method further includes extracting Factor H from the insoluble fraction with an extraction buffer having a conductivity of 14 to 30 mS/cm and a pH of 5.4 to 5.7 and enriching the Factor H extract with at least one chromatographic enrichment step.

In some embodiments, a method for reducing amidolytic activity in a Factor H composition is provided, the method including providing a Factor H composition (e.g., a Factor H composition extracted from a plasma precipitate such as a Fraction I or Fraction II+III precipitate or a recombinant Factor H composition such as a cell culture supernatant or cell lysate containing Factor H). The method also includes addition of a sugar and/or sugar alcohol (e.g., glucose, sorbitol, sucrose, or a combination thereof) into the composition at a final concentration of 2.5% to 10% and then incubating the stabilized composition at an elevated temperature of (e.g., 60° C. to 75° C.) for an extended period of time (e.g., 1 to 3 hours).

In some embodiments, an improved method is provided for enriching Factor H from a Factor H containing composition (e.g., a Factor H composition extracted from a plasma precipitate such as a Fraction I or Fraction II+III precipitate or a recombinant Factor H composition such as a cell culture supernatant or cell lysate containing Factor H), the method including binding Factor H to an anion exchange resin under low conductivity (e.g., 2 mS/cm to 5 mS/cm) and a mildly acidic pH (e.g., 6.4±0.3). The method also includes eluting Factor H from the anion exchange resin using either a combination of high conductivity (e.g., 20 mS/cm to 30 mS/cm) and a mildly acidic to neutral pH (e.g., 6.0 to 7.5) or a combination of moderate conductivity (e.g., 10 mS/cm to 20 mS/cm) and a neutral to mildly basic pH (e.g., 7.5 to 8.5).

In some embodiments, an improved method is provided for enriching Factor H from a Factor H containing composition (e.g., a Factor H composition extracted from a plasma precipitate such as a Fraction I or Fraction II+III precipitate or a recombinant Factor H composition such as a cell culture supernatant or cell lysate containing Factor H), the method including binding Factor H to heparin affinity resin at moderate conductivity (e.g., 7 mS/cm to 11 mS/cm) and neutral pH (e.g., 7.2±0.3). The method also includes eluting Factor H from the heparin affinity resin using high conductivity (e.g., 25 mS/cm to 35 mS/cm) and a mildly basic pH (e.g., 8.0±0.3).

In some embodiments, an improved method is provided for enriching Factor H from a Factor H containing composition (e.g., a Factor H composition extracted from a plasma precipitate such as a Fraction I or Fraction II+III precipitate or a recombinant Factor H composition such as a cell culture supernatant or cell lysate containing Factor H), the method including binding Factor H to a mixed mode resin (e.g., having an aliphatic or aromatic ligand) at neutral to slightly basic pH (e.g., 6.5 to 8.5). The method also includes eluting Factor H from the mixed mode resin at acidic pH (e.g., 4.5±0.3). In some embodiments, the mixed mode resin includes a hexylamine ligand.

In some embodiments, method further includes subjecting the Factor H composition to one or more dedicated virus removal and/or inactivation steps (e.g., solvent and detergent (S/D) treatment, nanofiltration, heat treatment, or incubation at low pH).

In certain embodiments, the methods provided herein include combinations of the improved process steps for preparing a Factor H composition. For example, in some embodiments, the methods include an improved Fraction II+III silicon dioxide filter cake enrichment step, a heat treatment step, and one or more of the improved anion exchange, heparin affinity, and mixed mode resin chromatographic steps.

Also contemplated are methods for the purification of recombinant Factor H compositions that include one or more of the heat treatment, anion exchange chromatographic, heparin affinity chromatographic, and mixed mode resin chromatographic steps.

Further details regarding the fractionation, extraction, enrichment, and viral removal and/or activation steps described here are provided below. It is contemplated that all combinations of specific conditions (e.g., pH, temperature, precipitant concentration, and/or ionic strength/conductivity) for performing each of these individual steps can be used to perform the methods described herein for purifying a Factor H composition. For brevity, each of these specific conditions are not repeated here.

IV. Extraction of Factor H from Plasma Precipitates

A. Preparation of Cryo-Poor Plasma

The starting material used for the preparation of commercial plasma-derived blood products, such as pooled IgG (e.g., IVIG or IgG for subcutaneous administration) generally consists of pooled lots of recovered plasma (i.e., plasma that has been separated from whole blood ex vivo) and/or or source plasma (i.e., plasma collected via plasmapheresis). The purification process typically starts by thawing previously frozen pooled plasma, which has already been assayed for safety and quality considerations, at a temperature no higher than 6° C. After complete thawing of the frozen plasma at low temperature, centrifugation is performed in the cold (e.g., ≤6° C.) to separate solid cryo-precipitates from the liquid supernatant. Alternatively, this separation step can be performed by filtration, rather than centrifugation. The liquid supernatant (also referred to as "cryo-poor plasma") is then, optionally, pre-processed by removing various factors, for example factor eight inhibitor bypass activity (FEIBA), Factor IX-complex, Factor VII, anti-thrombin III, Prothrombin complexes, by solid phase adsorption, chromatography, etc. The final product of these steps, which is used as the starting material for the fractionation process resulting in the isolation of IgG, alpha-1-antitrypsin (A1PI), and/or albumin, is commonly referred to a the "Cohn pool."

B. Fraction I Precipitation

To form a Fraction I precipitate (e.g., a Cohn or Kistler-Nitschmann Fraction I), the Cohn pool (e.g., cryo-poor plasma solution) is cooled to below about 6° C. (typically to about 0±1° C.) and the pH of the solution is adjusted to between about 7.0 and about 7.5. In some embodiments, the pH of the Cohn pool is adjusted to between about 7.1 and about 7.3. In a specific embodiment, the pH of the cryo-poor plasma is adjusted to a pH of at or about 7.2. Pre-cooled alcohol (typically ethanol, e.g., denatured ethanol) is then added to a target concentration of from about 6% to about 10% (v/v), typically while stirring the solution. In some embodiments, ethanol (e.g., denatured ethanol) is added to a target concentration of from about 7% to about 9% (v/v). In a specific embodiment, ethanol (e.g., denatured ethanol) is added to a target concentration of at or about 8% (v/v). At the same time the temperature is further lowered to below 0° C., typically between about −4° C. and about 0° C. In a specific embodiment, the temperature is lowered to at or about −2° C., to precipitate components of the cryo-poor plasma, including Factor H. Typically, the precipitation reaction includes an incubation time of at least about 1 hour, although shorter or longer incubation times may also be employed. After completion of the precipitation reaction, the supernatant (e.g., "Supernatant I") is then separated from the precipitate (e.g., "Fraction I" precipitate) by centrifugation, filtration, or other suitable means.

As compared to conventional methods for Fraction I precipitation, (e.g., as described in Cohn et al., supra; Oncley et al., supra), some embodiments provided herein result in improved yields of plasma factors (e.g., Factor H). In one embodiment, the precipitating alcohol is added in a fashion that finely disperses or that rapidly disperses the alcohol at the point of addition. For example, in one embodiment, precipitating alcohol is added to the plasma or derivative thereof (e.g., cryo-poor plasma) by spraying. In a second embodiment, precipitating alcohol is added to the plasma or derivative thereof (e.g., cryo-poor plasma) from below or directly adjacent to a stirring apparatus (e.g., an impeller). Addition of alcohol by any of these mechanisms avoids local over-concentration of alcohol which occurs, for example, at the point of fluent addition and results in the irreversible denaturation of proteins and/or precipitation of proteins that would otherwise be recovered in the supernatant.

In another embodiment, one or more pH modifying agent is added in a fashion that finely disperses or that rapidly disperses the pH modifying agent at the point of addition. For example, in one embodiment, the pH modifying agent is added by spraying. In a second embodiment, the pH modifying agent is added from below or directly adjacent to a stirring apparatus (e.g., an impeller). In a third embodiment, the pH modifying agent is added by sprinkling a solid form of the agent over a delocalized area.

In some embodiments, the pH of the solution is adjusted after addition of the precipitating alcohol. In some embodiments, the pH of the solution is adjusted during the addition of the precipitating alcohol. In some embodiments, the pH of the solution is adjusted in any combination of prior to, during, and after addition of the precipitating alcohol. In some embodiments, the pH of the solution is maintained at the desired pH throughout the precipitation incubation by monitoring and adjusting the pH of the solution as needed. In a preferred embodiment, the alcohol is ethanol (e.g., denatured ethanol).

Although the process for preparing a Fraction I precipitate is described above as a linear process, the skilled artisan will understand that the order of individual steps may be switched, combined, and/or reordered. For example, in some implementations, the pH of the Cohn pool may be adjusted prior to, during, and/or after cooling the solution down to a target temperature.

C. Extraction of Factor H from Fraction I Precipitate

In some embodiments, Factor H is prepared from Fraction I precipitate by suspending the precipitate in a Fraction I extraction buffer. In some embodiments, the suspension step includes addition of the extraction buffer to the Fraction I precipitate followed by stirring (e.g., by hand, with stir bar, or with an impeller). In some embodiments, extracting Factor H includes mechanically breaking down the Fraction I precipitate, before or after addition of the extraction buffer. Examples of techniques that can be used to break down the Fraction I precipitate include, without limitation, cutting the precipitate into small pieces (e.g., with one or more blades), mashing the precipitate, blending the precipitate, grinding the precipitate, and using pressure or sonication to homogenize the precipitate. Methods for implementing these strategies are known in the art.

In some embodiments, the Fraction I precipitate is suspended at a ratio of 1 part precipitate to from about 4 parts to about 40 parts extraction buffer. Other suitable ranges for the suspension ratio include, without limitation, from about 1:8 to about 1:30, from about 1:10 to about 1:20, from about 1:12 to about 1:18, from about 1:13 to about 1:17, and from about 1:14 to about 1:16. Some embodiments, suspension ratio is about 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, or higher. In a specific embodiment, the suspension ratio is about 1 part precipitate to about 15 parts suspension buffer. In another specific embodiment, the suspension ratio is about 1 part precipitate to about 20 parts suspension buffer.

In some embodiments, the Fraction I extraction buffer has a pH from about 4.0 to about 10.0. In some embodiments, the Fraction I extraction buffer has a pH from about 5.0 to about 7.0. In some embodiments, the Fraction I extraction buffer has a pH from about 7.0 to about 9.0. In some embodiments, the Fraction I extraction buffer has a pH from about 5.0 to about 9.0. In some embodiments, the Fraction I extraction buffer has a pH of 4.5±0.5, 4.6±0.5, 4.7 4.8±0.5, 4.9±0.5, 5.0±0.5, 5.1±0.5, 5.2±0.5, 5.3±0.5, 5.4±0.5, 5.5±0.5, 5.6±0.5, 5.7±0.5, 5.8±0.5, 5.9±0.5, 6.0±0.5, 6.1±0.5, 6.2±0.5, 6.3±0.5, 6.4±0.5, 6.5±0.5, 6.6±0.5, 6.7±0.5, 6.8±0.5, 6.9±0.5, 7.0±0.5, 7.1±0.5, 7.2±0.5, 7.3±0.5, 7.4±0.5, 7.5±0.5, 7.6±0.5, 7.7±0.5, 7.8±0.5, 7.9±0.5, 8.0±0.5, 8.1±0.5, 8.2±0.5, 8.3±0.5, 8.4±0.5, 8.5±0.5, 8.6±0.5, 8.7±0.5, 8.8±0.5, 8.9±0.5, 9.0±0.5, 9.1±0.5, 9.2±0.5, 9.3±0.5, 9.4±0.5, or 9.5±0.5.

Generally, these pH requirements can be met using a buffering agent, including without limitation, acetate, citrate, monobasic phosphate, dibasic phosphate, mixtures thereof, and the like. Suitable buffer concentrations typically range from about 2.5 mM to about 100 mM, or from about 5 mM to about 50 mM, or about 2.5 mM, 5 mM, 10 mM, 15 mM, 20 mM, 25 mM, 50 mM, 75 mM, 100 mM, 125 mM, 150 mM, 175 mM, or 200 mM buffering agent.

In some embodiments, the extraction buffer has a conductivity equal to that of a solution of from about 50 to about 500 mM sodium chloride. In some embodiments, the extraction buffer has a conductivity equal to that of a solution of from about 100 to about 300 mM sodium chloride. In a specific embodiment, the extraction buffer has a conductivity equal to that of a solution of from about 150 to about 200 mM sodium chloride.

In some embodiments, the extraction buffer includes from 10 to 100 mM buffering agent (e.g., Tris), from 150 to 250 mM of an alkaline metal chloride salt (e.g., sodium chloride), optionally, from 1 to 10 mM of a metal chelating agent (e.g., EDTA and/or EGTA), and a pH from 7.5 to 8.5. In a specific embodiment, the extraction buffer includes 20 to 40 mM Tris, 175 to 225 mM sodium chloride, 5±1 mM EDTA, and a pH of 8.0±0.2.

Generally, the extraction is performed at a temperature of from about 0° C. and about 25° C. In certain embodiments, the extraction is performed at about 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., or 25° C. In a particular embodiment, the extraction is performed at around room temperature (about 20° C.). In another particular embodiment, the extraction is performed at from about 2° C. to about 10° C. In some embodiments, the extraction process is performed under continuous agitation (e.g., stirring, cutting, mashing, blending, grinding, or otherwise homogenizing) until all soluble components of the Fraction I precipitate are brought into solution. In certain embodiments, the extraction will proceed for at or about between 30 and 300 minutes, or for at or between 120 and 240 min, or for at or about between 150 and 210 minutes. In certain embodiments, the extraction process will proceed for about 30, 45, 60, 90, 120, 150, 180, 210, 240, 270, 300, or more minutes, optionally, with continuous agitation.

D. Fraction II+III Precipitation

To form a Fraction II+III precipitate (e.g., a Cohn Fraction II+III precipitate or Kistler-Nitschmann Precipitate A), a Cohn pool or a derivative thereof (e.g., a Fraction I supernatant) is cooled to below about 0° C. and the pH of the solution is adjusted to between about 5.5 and about 7.5. In some embodiments, the pH of the Cohn pool or derivative thereof is adjusted to between about 6.5 and about 7.0. In some embodiments, the pH of the Cohn pool or derivative thereof is adjusted to between about 5.5 and about 6.0. Pre-cooled alcohol (typically ethanol, e.g., denatured ethanol) is then added to a target concentration of from about 17% to about 27% (v/v), typically while stirring the solution. In some embodiments, ethanol (e.g., denatured ethanol) is added to a target concentration of from about 20% to about 25% (v/v). At the same time the temperature is further lowered, typically between about −9° C. and about −3° C. In a specific embodiment, the temperature is lowered to at or about −7° C., to precipitate components of the cryo-poor plasma or derivative thereof, including Factor H. Typically, the precipitation reaction includes an incubation time of at least about 1 hour, although shorter or longer incubation times may also be employed. After completion of the precipitation reaction, the supernatant (e.g., "Supernatant II+III") is then separated from the precipitate (e.g., "Fraction II+III" precipitate) by centrifugation, filtration, or other suitable means.

As compared to conventional methods for Fraction II+III precipitation, (e.g., as described in Cohn et al., supra; Oncley et al., supra), some embodiments provided herein result in improved yields of plasma factors (e.g., Factor H). In one embodiment, the precipitating alcohol is added in a fashion that finely disperses or that rapidly disperses the alcohol at the point of addition. For example, in one embodiment, precipitating alcohol is added to the plasma or derivative thereof (e.g., cryo-poor plasma) by spraying. In a second embodiment, precipitating alcohol is added to the Cohn pool or derivative thereof (e.g., Fraction I supernatant) from below or directly adjacent to a stirring apparatus (e.g., an impeller). Addition of alcohol by any of these mechanisms avoids local over-concentration of alcohol which occurs, for example, at the point of fluent addition and results in the irreversible denaturation of proteins and/or precipitation of proteins that would otherwise be recovered in the supernatant.

In another embodiment, one or more pH modifying agent is added in a fashion that finely disperses or that rapidly disperses the pH modifying agent at the point of addition. For example, in one embodiment, the pH modifying agent is added by spraying. In a second embodiment, the pH modifying agent is added from below or directly adjacent to a stirring apparatus (e.g., an impeller). In a third embodiment, the pH modifying agent is added by sprinkling a solid form of the agent over a delocalized area.

In some embodiments, the pH of the solution is adjusted after addition of the precipitating alcohol. In some embodiments, the pH of the solution is adjusted during the addition of the precipitating alcohol. In some embodiments, the pH of the solution is adjusted in any combination of prior to, during, and after addition of the precipitating alcohol. In some embodiments, the pH of the solution is maintained at the desired pH throughout the precipitation incubation by monitoring and adjusting the pH of the solution as needed. In a preferred embodiment, the alcohol is ethanol (e.g., denatured ethanol).

Although the process for preparing a Fraction II+III precipitate is described above as a linear process, the skilled artisan will understand that the order of individual steps may be switched, combined, and/or reordered. For example, in some implementations, the pH of the Cohn pool may be adjusted prior to, during, and/or after cooling the solution down to a target temperature.

In some embodiments, the Fraction II+III precipitation is performed at a temperature between about −5° C. and about −9° C. In some embodiments, the Fraction II+III precipitation is performed at a temperature between about −7° C. and about −9° C. In one embodiment, the precipitation step is performed at a temperature of at or about −7° C. In another embodiment, the precipitation step is performed at a temperature of at or about −8° C. In another embodiment, the precipitation step is performed at a temperature of at or about −9° C. In certain embodiments, the alcohol concentration of the precipitation step is between about 23% and about 27%. In a preferred embodiment, the alcohol concentration is between about 24% and about 26%. In another preferred embodiment, the alcohol concentration is at or about 25%. In other embodiments, the alcohol concentration may be at or about 23%, 24%, 25%, 26%, or 27%. In a particular embodiment, the second precipitation step is performed at a temperature of at or about −7° C. with an alcohol concentration of at or about 25%. In one embodiment, the alcohol is ethanol.

In a specific embodiment, the Fraction II+III precipitation is performed at a temperature of at or about −7° C. with at or about 25% ethanol at a pH of about 6.9. In some embodiments, the pH of the solution is maintained at or about 6.9 for the entirety of the precipitation incubation or hold time.

E. IgG Extraction and Silicon Dioxide Treatment of Fraction II+III Precipitate

In order to solubilize, and thus separate, the IgG content of the Factor H Fraction II+III precipitate, a cold extraction buffer is used to suspend the Fractionation II+III precipitate at a typical ratio of 1 part precipitate to 15 parts of extraction buffer. Other suitable re-suspension ratios may be used, for example from about 1:8 to about 1:30, or from about 1:10 to about 1:20, or from about 1:12 to about 1:18, or from about 1:13 to about 1:17, or from about 1:14 to about 1:16. In certain embodiments, the re-suspension ratio may be about 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, or higher.

Suitable solutions for the extraction of the Fraction II+III precipitate will generally have a pH between about 4.0 and about 5.5. In certain embodiments, the solution will have a pH between about 4.5 and about 5.0, in other embodiments, the extraction solution will have a pH of about 4.0, 4.1, 4.2, 4.3, 4.4, 4.5, 4.6, 4.7, 4.8, 4.9, 5.0, 5.1, 5.2, 5.3, 5.4, or 5.5. In a preferred embodiment, the pH of the extraction buffer will be at or about 4.5. In another preferred embodiment, the pH of the extraction buffer will be at or about 4.7. In another preferred embodiment, the pH of the extraction buffer will be at or about 4.9. Generally, these pH requirements can be met using a buffering agent selected from, for example, acetate, citrate, monobasic phosphate, dibasic phosphate, mixtures thereof, and the like. Suitable buffer concentrations typically range from about 5 to about 100 mM, or from about 10 to about 50 mM, or about 5, 10, 15, 20, 25, 30, 35, 40, 45, 50, 55, 60, 65, 70, 75, 80, 85, 90, 95, or 100 mM buffering agent.

The extraction buffer will preferably have a conductivity of from about 0.5 mS·cm$^{-1}$ to about 2.0 mS·cm$^{-1}$. For example, in certain embodiments, the conductivity of the extraction buffer will be about 0.5 mS·cm$^{-1}$, or about 0.6, 0.7, 0.8, 0.9, 1.0, 1.1, 1.2, 1.3, 1.4, 1.5, 1.6, 1.7, 1.8, 1.9, or about 2.0 mS·cm$^{-1}$. One of ordinary skill in the art will know how to generate extraction buffers having an appropriate conductivity.

In some embodiments, the extraction is performed at between about 0° C. and about 10° C., or between about 2° C. and about 8° C. In certain embodiments, the extraction may be performed at about 0° C., 1° C., 2° C., 3° C., 4° C., 5° C., 6° C., 7° C., 8° C., 9° C., or 10° C. In a particular embodiment, the extraction is performed at between about 2° C. and about 10° C. Typically, the extraction process will proceed for between about 60 and about 300 minutes, or for between about 120 and 240 min, or for between about 150 and 210 minutes, while the suspension is continuously stirred. In certain embodiments, the extraction process will proceed for about 60, 70, 80, 90, 100, 110, 120, 130, 140, 150, 160, 170, 180, 190, 200, 210, 220, 230, 240, 250, 260, 270, 280, 290, or about 300 minutes. In a preferred embodiment, the extraction process will proceed for at least 160 minutes with continuous stirring.

In some embodiments, the extraction buffer contains 5 mM monobasic sodium phosphate, 5 mM acetate, and 0.04% to 0.06% glacial acetic acid (v/v). In some embodiments, the Fraction II+III precipitate is extracted with a paste to buffer ration of at or about 1:15 at a pH of at or about 4.5±0.2. In some embodiments, the Fraction II+III precipitate in a dissolution buffer containing 510 mL glacial acetic acid per 1000 L. In some embodiments, the Fraction II+III precipitate in a dissolution buffer containing about 600 mL glacial acetic acid per 1000 L. In one particular embodiment, an exemplary extraction buffer may contain at or about 5 mM monobasic sodium phosphate and at or about 5 mM acetate at a pH of at or about 4.5±0.2 and conductivity of at or about 0.7 to 0.9 mS/cm.

The extracted Fraction II+III precipitate is then treated by addition of finely divided silica dioxide particles (e.g., fumed silica, Aerosil®) followed by a 40 to 80 minute incubation period during which the suspension is constantly mixed. In certain embodiments, the incubation period will be between about 50 minutes and about 70 minutes, or about 30, 35, 40, 45, 50, 55, 60, 65, 70, 75, 80, or more minutes. Generally, the treatment will be performed at between about 0° C. and about 10° C., or between about 2° C. and about 8° C. In certain embodiments, the treatment may be performed at about 0° C., 1° C., 2° C., 3° C., 4° C., 5° C., 6° C., 7° C., 8° C., 9° C., or 10° C. In a particular embodiment, the treatment is performed at between about 2° C. and about 10° C.

In some embodiments, fumed silica is added at a concentration of between about 20 g/kg II+III paste and about 100 g/kg II+III paste (i.e., for a Fraction II+III precipitate that is extracted at a ratio of 1:15, fumed silica should be added at a concentration from about 20 g/16 kg II+III suspension to about 100 g/16 kg II+III suspension, or at a final concentration of about 0.125% (w/w) to about 0.625% (w/w)). In certain embodiments, the fumed silica may be added at a concentration of about 20 g/kg II+III paste, or about 25, 30, 35, 40, 45, 50, 55, 60, 65, 70, 75, 80, 85, 90, 95, or 100 g/kg II+III paste. In one specific embodiment, fumed silica (e.g., Aerosil 380 or equivalent) is added to the Fraction II+III suspension to a final concentration of about 40 g/16 kg II+III. Mixing takes place at about 2° C. to 8° C. for at least 50 to 70 minutes.

In some embodiments, the fumed silica treatment includes addition of from about 0.01 kg/kg II+III paste to about 0.07 kg/kg II+III paste, or from about 0.02 kg/kg II+III paste to about 0.06 kg/kg II+III paste, or from about 0.03 kg/kg II+III paste to about 0.05 kg/kg II+III paste, or about 0.02, 0.03, 0.04, 0.05, 0.06, or 0.07 kg/kg II+III paste, and the mixture will be incubated for between about 50 minutes and about 70 minutes, or about 30, 35, 40, 45, 50, 55, 60, 65, 70, 75, 80, or more minutes at a temperature between about 2° C. and about 8° C.

In order to separate the insoluble fraction of the Fraction II+III precipitate (i.e., the Fraction II+III silicon dioxide filter cake), the suspension is filtered, typically using depth filtration. Depth filters that may be employed in the methods provided herein include, metallic, glass, ceramic, organic (such as diatomaceous earth) depth filters, and the like. Example of suitable filters include, without limitation, Cuno 50SA, Cuno 90SA, and Cuno VR06 filters (Cuno). Alternatively, the separation step can be performed by centrifugation rather than filtration.

In certain embodiments, filter aid, for example Celpure C300 (Celpure) or Hyflo-Super-Cel (World Minerals), will be added after the silica dioxide treatment, to facilitate depth filtration. Filter aid can be added at a final concentration of from about 0.01 kg/kg II+III paste to about 0.07 kg/kg II+III paste, or from about 0.02 kg/kg II+III paste to about 0.06 kg/kg II+III paste, or from about 0.03 kg/kg II+III paste to about 0.05 kg/kg II+III paste. In certain embodiments, the filter aid will be added at a final concentration of about 0.01 kg/kg II+III paste, or about 0.02, 0.03, 0.04, 0.05, 0.06, or 0.07 kg/kg II+III paste.

In some embodiments, where the soluble fraction is separated from the insoluble fraction by filtration, the filter is washed with between about 3 and about 5 volumes of the filter dead volume after completing the filtration. In certain embodiments, the filter will be washed with between about 3.5 volumes and about 4.5 volumes, or at least about 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 volumes of the filter dead volume. In a particular embodiment, the filter press will be washed with at least about 3.6 dead volumes of suspension buffer.

F. Extraction of Factor H from Fraction II+III Silicon Dioxide Filter Cake

In some embodiments, Factor H is extracted from Fraction II+III silicon dioxide filter cake by suspending the precipitate in a Fraction II+III silicon dioxide filter cake extraction buffer. In some embodiments, the suspension step includes addition of the extraction buffer to the Fraction II+III silicon dioxide filter cake followed by stirring (e.g., by hand, with stir bar, or with an impeller). In some embodiments, extracting Factor H includes mechanically breaking down the Fraction II+III silicon dioxide filter cake, before or after addition of the extraction buffer. Examples of techniques that can be used to break down the Fraction II+III silicon dioxide filter cake include, without limitation, cutting the precipitate into small pieces (e.g., with one or more blades), mashing the precipitate, blending the precipitate, grinding the precipitate, and using pressure or sonication to homogenize the precipitate. Methods for implementing these strategies are known in the art.

In some embodiments, the Fraction II+III silicon dioxide filter cake is suspended at a ratio of 1 part precipitate to from about 3 parts to about 40 parts extraction buffer. Other suitable ranges for the suspension ratio include, without limitation, from about 1:8 to about 1:30, from about 1:10 to about 1:20, from about 1:12 to about 1:18, from about 1:13 to about 1:17, and from about 1:14 to about 1:16. Some embodiments, suspension ratio is about 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, or higher. In a specific embodiment, the suspension ratio is about 1 part precipitate to about 3 to 10 parts suspension buffer. In another specific embodiment, the suspension ratio is about 1 part precipitate to about 4 to 8 parts suspension buffer. In another specific embodiment, the suspension ratio is about 1 part precipitate to about 6 parts suspension buffer.

In some embodiments, the Fraction II+III silicon dioxide filter cake extraction buffer has a pH and conductivity optimal for Factor H extraction, but which leads to only limited extraction of proteolytic (e.g., amidolytic) activity. In some embodiments, these conditions include a pH from about 4.0 to about 6.0 and a conductivity of from 10 mS/cm to 30 mS/cm. In some embodiments, the Fraction II+III silicon dioxide filter cake extraction buffer has a pH from about 4.2 to about 5.8 and a conductivity of from 12 mS/cm to 27 mS/cm. In a specific embodiment, the Fraction II+III silicon dioxide filter cake extraction buffer has a pH from about 4.6 to about 5.4 and a conductivity of from 15 mS/cm to 24 mS/cm. In some embodiments, the Fraction II+III silicon dioxide filter cake extraction buffer has a pH and conductivity combination selected from variations 1 to 64 listed in Table 1.

TABLE 1

Exemplary combinations of pH and conductivity for Fraction II + III silicon dioxide filter cake extraction.

|  | 4.0-6.0 | 4.2-5.8 | 4.6-5.4 | 4.8 ± 0.2 | 4.9 ± 0.2 | 5.0 ± 0.2 | 5.1 ± 0.2 | 5.2 ± 0.2 |
|---|---|---|---|---|---|---|---|---|
| 10-30 mS/cm | Var. 1 | Var. 9 | Var. 17 | Var. 25 | Var. 33 | Var. 41 | Var. 49 | Var. 57 |
| 12-27 mS/cm | Var. 2 | Var. 10 | Var. 18 | Var. 26 | Var. 34 | Var. 42 | Var. 50 | Var. 58 |
| 15-24 mS/cm | Var. 3 | Var. 11 | Var. 19 | Var. 27 | Var. 35 | Var. 43 | Var. 51 | Var. 59 |
| 17 ± 2 mS/cm | Var. 4 | Var. 12 | Var. 20 | Var. 28 | Var. 36 | Var. 44 | Var. 52 | Var. 60 |
| 18 ± 2 mS/cm | Var. 5 | Var. 13 | Var. 21 | Var. 29 | Var. 37 | Var. 45 | Var. 53 | Var. 61 |
| 19 ± 2 mS/cm | Var. 6 | Var. 14 | Var. 22 | Var. 30 | Var. 38 | Var. 46 | Var. 54 | Var. 62 |
| 20 ± 2 mS/cm | Var. 7 | Var. 15 | Var. 23 | Var. 31 | Var. 39 | Var. 47 | Var. 55 | Var. 63 |
| 21 ± 2 mS/cm | Var. 8 | Var. 16 | Var. 24 | Var. 32 | Var. 40 | Var. 48 | Var. 56 | Var. 64 |

In some embodiments, these conditions include a pH from about 5.0 to about 6.0 and a conductivity of from 10 mS/cm to 40 mS/cm. In some embodiments, the Fraction II+III silicon dioxide filter cake extraction buffer has a pH from about 5.2 to about 5.8 and a conductivity of from 12 mS/cm to 35 mS/cm. In a specific embodiment, the Fraction II+III silicon dioxide filter cake extraction buffer has a pH from about 5.4 to about 5.7 and a conductivity of from 14 mS/cm to 30 mS/cm. In some embodiments, the Fraction II+III silicon dioxide filter cake extraction buffer has a pH and conductivity combination selected from variations 65 to 192 listed in Table 2.

TABLE 2

Exemplary combinations of pH and conductivity for Fraction II + III silicon dioxide filter cake extraction.

|  | 5.0-6.0 | 5.2-5.8 | 5.4-5.7 | 5.3 ± 0.2 | 5.4 ± 0.2 | 5.5 ± 0.2 | 5.6 ± 0.2 | 5.7 ± 0.2 |
|---|---|---|---|---|---|---|---|---|
| 10-40 mS/cm | Var. 65 | Var. 81 | Var. 97 | Var. 113 | Var. 129 | Var. 145 | Var. 161 | Var. 177 |
| 12-35 mS/cm | Var. 66 | Var. 82 | Var. 98 | Var. 114 | Var. 130 | Var. 146 | Var. 162 | Var. 178 |
| 14-30 mS/cm | Var. 67 | Var. 83 | Var. 99 | Var. 115 | Var. 131 | Var. 147 | Var. 163 | Var. 179 |
| 16 ± 2 mS/cm | Var. 68 | Var. 84 | Var. 100 | Var. 116 | Var. 132 | Var. 148 | Var. 164 | Var. 180 |
| 17 ± 2 mS/cm | Var. 69 | Var. 85 | Var. 101 | Var. 117 | Var. 133 | Var. 149 | Var. 165 | Var. 181 |
| 18 ± 2 mS/cm | Var. 70 | Var. 86 | Var. 102 | Var. 118 | Var. 134 | Var. 150 | Var. 166 | Var. 182 |
| 19 ± 2 mS/cm | Var. 71 | Var. 87 | Var. 103 | Var. 119 | Var. 135 | Var. 151 | Var. 167 | Var. 183 |
| 20 ± 2 mS/cm | Var. 72 | Var. 88 | Var. 104 | Var. 120 | Var. 136 | Var. 152 | Var. 168 | Var. 184 |
| 21 ± 2 mS/cm | Var. 73 | Var. 89 | Var. 105 | Var. 121 | Var. 137 | Var. 153 | Var. 169 | Var. 185 |
| 22 ± 2 mS/cm | Var. 74 | Var. 90 | Var. 106 | Var. 122 | Var. 138 | Var. 154 | Var. 170 | Var. 186 |
| 23 ± 2 mS/cm | Var. 75 | Var. 91 | Var. 107 | Var. 123 | Var. 139 | Var. 155 | Var. 171 | Var. 187 |
| 24 ± 2 mS/cm | Var. 76 | Var. 92 | Var. 108 | Var. 124 | Var. 140 | Var. 156 | Var. 172 | Var. 188 |
| 25 ± 2 mS/cm | Var. 77 | Var. 93 | Var. 109 | Var. 125 | Var. 141 | Var. 157 | Var. 173 | Var. 189 |
| 26 ± 2 mS/cm | Var. 78 | Var. 94 | Var. 110 | Var. 126 | Var. 142 | Var. 158 | Var. 174 | Var. 190 |
| 27 ± 2 mS/cm | Var. 79 | Var. 95 | Var. 111 | Var. 127 | Var. 143 | Var. 159 | Var. 175 | Var. 191 |
| 28 ± 2 mS/cm | Var. 80 | Var. 96 | Var. 112 | Var. 128 | Var. 144 | Var. 160 | Var. 176 | Var. 192 |

Generally, these pH requirements can be met using a buffering agent, including without limitation, acetate, citrate, monobasic phosphate, dibasic phosphate, mixtures thereof, and the like. Suitable buffer concentrations typically range from about 2.5 mM to about 100 mM, or from about 5 mM to about 50 mM, or about 2.5 mM, 5 mM, 10 mM, 15 mM, 20 mM, 25 mM, 50 mM, 75 mM, 100 mM, 125 mM, 150 mM, 175 mM, or 200 mM buffering agent.

In some embodiments, the extraction buffer includes a citrate buffer (e.g., a sodium citrate buffer) at a concentration between about 10 mM and about 100 mM. In some embodiments, the extraction buffer includes between about 25 mM and about 75 mM sodium citrate. In yet other embodiments, the extraction buffer includes between about 40 mM and about 60 mM sodium citrate. In a specific embodiment, the extraction buffer includes about 50 mM sodium citrate.

Generally, the extraction is performed at a temperature of from about 0° C. and about 25° C. In certain embodiments, the extraction is performed at about 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., or 25° C. In a particular embodiment, the extraction is performed at around room temperature (about 20° C.). In another particular embodiment, the extraction is performed at from about 2° C. to about 10° C. In some embodiments, the extraction process is performed under continuous agitation (e.g., stirring, cutting, mashing, blending, grinding, or otherwise homogenizing) until all soluble components of the Fraction I precipitate are brought into solution. In certain embodiments, the extraction will proceed for at or about between 30 and 300 minutes, or for at or between 120 and 240 min, or for at or about between 150 and 210 minutes. In certain embodiments, the extraction process will proceed for about 30, 45, 60, 90, 120, 150, 180, 210, 240, 270, 300, or more minutes, optionally, with continuous agitation.

V. Expression of Recombinant Factor H

Recombinant Factor H proteins can be produced by expression in any suitable prokaryotic or eukaryotic host system. Examples of eukaryotic cells include, without limitation, mammalian cells, such as CHO, COS, HEK 293, BHK, SK-Hep, and HepG2; insect cells, for example SF9 cells, SF21 cells, S2 cells, and High Five cells; and yeast cells, for example *Saccharomyces* or *Schizosaccharomyces* cells. In one embodiment, the Factor H proteins can be expressed in bacterial cells, yeast cells, insect cells, avian cells, mammalian cells, and the like. For example, in a human cell line, a hamster cell line, or a murine cell line. In one particular embodiment, the cell line is a CHO, BHK, or HEK cell line. In one embodiment, the cell line is a CHO cell line.

In one embodiment, the cells may be any mammalian cell that can be cultured, preferably in a manufacturing process (i.e., at least 1 liter), to produce a desired Factor H protein. Examples include the monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells/-DHFR, such as the DUKX-B11 subclone (CHO, Uriaub and Chasin, Proc. Natl. Acad. Sci. USA, 77:4216 (1980)); mouse Sertoli cells (TM4, Mather, Biol. Reprod, 23:243-251 (1980)); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N. Y. Acad. Sci., 383:44-68 (1982)); MRC 5 cells; FS4 cells; and the human hepatoma line (Hep G2). Preferably, the cell line is a rodent cell line, especially a hamster cell line such as CHO or BHK.

A wide variety of vectors can be used for the expression of a Factor H protein and can be selected from eukaryotic and prokaryotic expression vectors. In certain embodiments, a plasmid vector is contemplated for use in expressing a Factor H protein. In general, plasmid vectors containing replicon and control sequences which are derived from species compatible with the host cell are used in connection with these hosts. The vector can carry a replication site, as well as marking sequences which are capable of providing phenotypic selection in transformed cells. The plasmid will comprise a nucleotide sequence encoding a Factor H protein operably linked to one or more control sequences, for example, a promoter.

A preferred method of preparing stable CHO cell clones expressing a recombinant Factor H protein is as follows. A DHFR deficient CHO cell line DUKX-B11 is transfected with a DHFR expression vector to allow for expression of the relevant recombinant protein, essentially as described in U.S. Pat. No. 5,250,421 (Kaufman et al., Genetics Institute, Inc.). Selection is carried out by growth in Hypoxanthine/Thymidine (HT) free media and amplification of the relevant region coding for expression of the recombinant Factor H protein and DHFR gene is achieved by propagation of the cells in increasing concentrations of methotrexate. Where appropriate, CHO cell lines may be adapted for growth in serum and/or protein free medium, essentially as described in U.S. Pat. No. 6,100,061 (Reiter et al, Immuno Aktiengesellschaft).

In another preferred embodiment, stable HEK293 cells are prepared by transfecting with a construct containing a hygromycin selectable marker and selecting transformants by antibiotic resistance.

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Accordingly, in certain embodiments, a viral vector is used to introduce a nucleotide sequence encoding a Factor H protein into a host cell for expression. The viral vector will comprise a nucleotide sequence encoding a Factor H protein operably linked to one or more control sequences, for example, a promoter. Alternatively, the viral vector may not contain a control sequence and will instead rely on a control sequence within the host cell to drive expression of the Factor H protein. Non-limiting examples of virus vectors that may be used to deliver a nucleic acid include Adenoviral vectors, AAV vectors, and Retroviral vectors.

In one embodiment, an Adenovirus expression vector include those constructs containing adenovirus sequences sufficient to support packaging of the construct and to ultimately express a Factor H construct that has been cloned therein. Adenoviral vectors allow for the introduction of foreign sequences up to 7 kb (Grunhaus et al., Seminar in Virology, 200(2):535-546, 1992)).

In another embodiment, an adeno-associated virus (AAV) can be used to introduce a nucleotide sequence encoding a Factor H protein into a host cell for expression. AAV systems have been described previously and are generally well known in the art (Kelleher and Vos, Biotechniques, 17(6):1110-7, 1994; Cotten et al., Proc Natl Acad Sci USA, 89(13):6094-6098, 1992; Curiel, Nat Immun, 13(2-3):141-64, 1994; Muzyczka, Curr Top Microbiol Immunol, 158: 97-129, 1992). Details concerning the generation and use of rAAV vectors are described, for example, in U.S. Pat. Nos. 5,139,941 and 4,797,368, each incorporated herein by reference in their entireties for all purposes.

In one embodiment, a retroviral expression vector can be used to introduce a nucleotide sequence encoding a Factor H protein into a host cell for expression. These systems have been described previously and are generally well known in the art (Mann et al., Cell, 33:153-159, 1983; Nicolas and Rubinstein, In: Vectors: A survey of molecular cloning vectors and their uses, Rodriguez and Denhardt, eds., Stoneham: Butterworth, pp. 494-513, 1988; Temin, In: Gene Transfer, Kucherlapati (ed.), New York: Plenum Press, pp. 149-188, 1986). In a specific embodiment, the retroviral vector is a lentiviral vector (see, for example, Naldini et al., Science, 272(5259):263-267, 1996; Zufferey et al., Nat Biotechnol, 15(9):871-875, 1997; Blomer et al., J Virol., 71(9):6641-6649, 1997; U.S. Pat. Nos. 6,013,516 and 5,994, 136).

Non-limiting examples of vectors for prokaryotic expression include plasmids such as pRSET, pET, pBAD, etc., wherein the promoters used in prokaryotic expression vectors include lac, trc, trp, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

In certain embodiments, the methods of the present invention can comprise the use of a cell culture system operated under a batch or continuous mode of operation. For example, when batch cell cultures are utilized, they may be operated under single batch, fed-batch, or repeated-batch mode. Likewise, continuous cell cultures may be operated under, for example, perfusion, turbidostat or chemostat mode. Batch and continuous cell cultivation may be performed under either suspension or adherence conditions. When operated under suspension conditions, the cells will be freely suspended and mixed within the culture medium. Alternatively, under adherence conditions, the cells will be bound to a solid phase, for example, a microcarrier, a porous microcarrier, disk carrier, ceramic cartridge, hollow fiber, flat sheet, gel matrix, and the like.

A batch culture is typically a large scale cell culture in which a cell inoculum is cultured to a maximum density in a tank or fermenter, and harvested and processed as a single batch. A fed-batch culture it typically a batch culture which is supplied with either fresh nutrients (e.g., growth-limiting substrates) or additives (e.g., precursors to products). The feed solution is usually highly concentrated to avoid dilution of the bioreactor. In a repeated-batch culture, the cells are placed in a culture medium and grown to a desired cell density. To avoid the onset of a decline phase and cell death, the culture is then diluted with complete growth medium before the cells reach their maximum concentration. The amount and frequency of dilution varies widely and depends on the growth characteristics of the cell line and convenience of the culture process. The process can be repeated as many times as required and, unless cells and medium are discarded at subculture, the volume of culture will increase stepwise as each dilution is made. The increasing volume may be handled by having a reactor of sufficient size to allow dilutions within the vessel or by dividing the diluted culture into several vessels. The rationale of this type of culture is to maintain the cells in an exponentially growing state. Serial subculture is characterized in that the volume of culture is always increasing stepwise, there can be multiple harvests, the cells continue to grow and the process can continue for as long as desired. In certain embodiments, a Factor H protein may be recovered after harvesting the supernatant of a batch culture.

A continuous culture can be a suspension culture that is continuously supplied with nutrients by the inflow of fresh medium, wherein the culture volume is usually kept constant by the concomitant removal of spent medium. In chemostat and turbidostat methods, the extracted medium contains cells. Thus, the cells remaining in the cell culture vessel must grow to maintain a steady state. In the chemostat method, the growth rate is typically controlled by controlling the dilution rate, i.e., the rate at which fresh medium is added. The growth rate of the cells in the culture may be controlled, for example, at a sub-maximal growth rate, by alteration of the dilution rate. In contrast, in the turbidostat method, the dilution rate is set to permit the maximum growth rate that the cells can achieve at the given operating conditions, such as pH and temperature.

In a perfusion culture, the extracted medium is depleted of cells, which are retained in the culture vessel, for example, by filtration or by centrifugal methods that lead to the reintroduction of the cells into the culture. However, typically membranes used for filtration do not retain 100% of cells, and so a proportion are removed when the medium is extracted. It may not be crucial to operate perfusion cultures at very high growth rates, as the majority of the cells are retained in the culture vessel.

Stirred-tank reactor system can be used for batch and continuous cell cultures operated under suspension or adherent modes. Generally, the stirred-tank reactor system can be operated as any conventional stirred-tank reactor with any type of agitator such as a Rushton, hydrofoil, pitched blade, or marine.

VI. Reduction of Amidolytic Activity and Further Enrichment of Factor H

A. Heat Treatment

In some embodiments, a method for reducing amidolytic activity in a Factor H composition is provided, the method including providing a Factor H composition (e.g., a Factor H composition extracted from a plasma precipitate such as a Fraction I or Fraction II+III precipitate or a recombinant Factor H composition such as a cell culture supernatant or cell lysate containing Factor H). The method also includes add a sugar and/or sugar alcohol (e.g., glucose, sorbitol, sucrose, or a combination thereof) into the composition at a final concentration of 2.5% to 10% and then incubating the stabilized composition at an elevated temperature of (e.g., 60° C. to 75° C.) for an extended period of time (e.g., 1 to 3 hours).

In some embodiments, a heat treatment is used to reduce the amidolytic activity or other impurity in a Factor H composition (e.g., a Factor H composition purified from plasma or a recombinant Factor H composition). Advantageously, it was found that sugars and/or sugar alcohols could be used to stabilize Factor H at high temperatures sufficient to deactivate (e.g., denature) amidolytic contaminants in the composition. In some embodiments, Factor H is first stabilized in the composition by the addition of a sugar and/or sugar alcohol. In some embodiments, the final concentration of the sugar and/or sugar alcohol used for stabilization is from about 1% to about 15%. However, it was found that no further stabilization was achieved when the concentration of the stabilizer was increased above 5%. Thus in some embodiments, the final concentration of the sugar and/or sugar alcohol is from about 1% to about 7.5%. This notwithstanding, in some embodiments, it is still feasible to include more than 7.5% sugar and/or sugar alcohol for stabilization. In some embodiments, the concentration of the stabilizer is from about 2.5 to about 7.5%. In yet other embodiments, the concentration of the stabilizer is 2±1%, 3±1%, 4±1%, 5±1%, 6±1%, 7±1%, 8±1%, 9±1%, 10±1%, or higher. In a specific embodiment, the concentration of the stabilizer is about 5%.

In some embodiments, the stabilizer is a monosaccharide sugar. In a particular embodiment, the monosaccharide sugar is selected from the group consisting of a diose sugar, a triose sugar, a tetrose sugar, a pentose sugar, a hexose sugar, a heptose sugar, and an octose sugar. In a particular embodiment, the sugar is a pentose sugar, a hexose sugar, or a combination thereof. In a specific embodiment, the sugar is a hexose sugar.

In some embodiments, the stabilizer is a disaccharide sugar. In a particular embodiment, the disaccharide sugar is selected from disaccharide sugars formed from pentose and/or hexose monosaccharides. In another particular embodiment, the sugar is selected from disaccharide sugars formed from hexose monosaccharides. In one embodiment, the sugar is sucrose, glucose, or a combination thereof. In one specific embodiment, the sugar is sucrose. In another specific embodiment, the sugar is glucose.

In some embodiments, the stabilizer is a sugar alcohol. In a particular embodiment, the sugar alcohol is selected from glycol, glycerol, erythritol, threitol, ribitol, fucitol, iditol, volmitol, isomalt, maltitol, lactitol, mannitol, sorbitol, inositol, galactitol, dulcitol, xylitol, and arabitol. In a specific embodiment, the sugar alcohol is sorbitol.

In some embodiments, the stabilizer is a mixture of sugar and/or sugar alcohol. In one embodiment, the mixture contains at least two of a monosaccharide, a disaccharide, and a sugar alcohol. In another embodiment, the mixture contains at least two of a pentose sugar, a hexose sugar, a disaccharide formed from pentose and/or hexose monosaccharides, and a sugar alcohol. In another embodiment, the mixture contains at least two of sucrose, glucose, and sorbitol.

In some embodiments, the heat treatment includes incubation of a Factor H composition (e.g., a plasma-derived or recombinant Factor H composition) at an elevated temperature (e.g., 60° C. to 75° C.) for at least an hour. In some embodiments, the heat treatment includes incubation at an elevated temperature for at least two hours. As demonstrated in Example 11, incubation of a plasma-derived Factor H composition (e.g., a Factor H composition extracted from a Fraction I precipitate or Fraction II+III silicon dioxide filter cake) at 70° C. for two hours resulted in greater than 95% reduction in amidolytic activity in the composition. Further incubation at 70° C. (e.g., incubation for three or four hours) did not result in any further significant reduction of amidolytic activity. However, the sugar and/or sugar alcohol additive (e.g., glucose, sucrose, or sorbitol) provided significant stabilization of Factor H for up to four hours (FIG. 12). Thus, it is contemplated that, in certain instances where a longer heat treatment might be warranted (e.g., where a particularly stable impurity originating from plasma or a recombinant expression system is a target of the treatment), that a Factor H composition may be incubated at high temperature for at least three hours, at least four hours, or longer (e.g., 5, 6, 7, 8, 9, 10, or more hours). Thus, depending upon the concentration and identity of an impurity present in a Factor H composition, the skilled artisan will readily be able to modify the methods for heat inactivation of an impurity in a Factor H composition provided herein to fit their individual need.

In some embodiments, the heat treatment is performed at a temperature from about 60° C. to about 75° C. In some embodiments, the heat treatment is performed at from about 65° C. to about 75° C. In some embodiments, the heat treatment is performed at 60° C., 61° C., 62° C., 63° C., 64° C., 65° C., 66° C., 67° C., 68° C., 69° C., 70° C., 71° C., 72° C., 73° C., 74° C., or 75° C. In some embodiments, where the Factor H solution is a plasma-derived solution and the heat treatment is being performed to deactivate amidolytic contaminates in the solution, higher temperatures are used (e.g., 65° C. to 75° C.). However, it is contemplated that for certain impurities having less thermal stability than amidolytic proteases found in human blood (e.g., an impurity from a host cell in a recombinant Factor H expression system), a lower temperature can be used for the heat treatment, e.g., from 40° C. to 60° C. depending on the individual stability of the targeted impurity.

In one embodiment, a sugar and/or sugar alcohol is added to the composition (e.g., a clarified extract of a Fraction II+III filter cake) to a final concentration of from 2.5% to 7.5% and the heat treatment is performed at a temperature of from 60° C. to 75° C. for 1 to 4 hours. In one embodiment, a sugar and/or sugar alcohol is added to the composition (e.g., a clarified extract of a Fraction II+III filter cake) to a final concentration of from 2.5% to 7.5% and the heat treatment is performed at 65° C. to 70° C. for 1 to 4 hours. In one embodiment, a sugar and/or sugar alcohol is added to the composition (e.g., a clarified extract of a Fraction II+III filter cake) to a final concentration of 5±1% and the heat treatment is performed at a temperature of from 65° C. to 70° C. for 1 to 4 hours. In one embodiment, a sugar and/or sugar alcohol is added to the composition (e.g., a clarified extract of a Fraction II+III filter cake) to a final concentration of 5±1% and the heat treatment is performed at a temperature of from 65° C. to 70° C. for 2±0.5 hours. In a specific embodiment, dextrose (i.e., glucose) is added to the composition (e.g., a clarified extract of a Fraction II+III filter cake) to a final concentration of 5±1% and the heat treatment is performed at a temperature of from 65° C. to 70° C. for 2±0.5 hours.

In some embodiments, the composition is filtered after the heat treatment to remove insoluble material. In one embodiment, the filtration is a sterile filtration performed with a 0.2 μM and/or 0.45 μM filter.

B. Buffer Exchange

In some embodiments, the buffer of the composition is modified or exchanged after the heat treatment. Non-limiting examples of methods useful for adjusting the buffer conditions of the solution include diafiltration, ultrafiltration and diafiltration (UF/DF), dialysis, dilution, dilution and concentration, and gel filtration/de-salting chromatography. In one embodiment, the solution conditions are modified and the protein concentration is concentrated using ultrafiltration and diafiltration.

In some embodiments, ultra/diafiltration is performed using a cassette (e.g., with an open channel screen) and an ultra/diafiltration membrane having a nominal molecular weight cut off (NMWCO) of no more than about 150 kDa or no more than about 140, 130, 120, 100, 90, 80, 70, 60, 50, 40, or 30 kDa. In one embodiment, the ultrafiltration membrane has a NMWCO of about 30 kDa. In one embodiment, the ultra/diafiltration membrane is used with an A-screen geometry. In another embodiment, the ultra/diafiltration membrane is used with a V-screen geometry.

In some embodiments, the heat-treated sample is diafiltered into a buffer suitable for viral inactivation by S/D treatment. Methods for the detergent treatment of plasma-derived fractions are well known in the art (for review see, Pelletier J P et al., Best Pract Res Clin Haematol. 2006; 19(1):205-42, the disclosure of which is expressly incorporated by reference herein in its entirety for all purposes). A skilled artisan will be able to determine a suitable buffer based upon the requirements of their particular purification scheme.

In one embodiment, the heat-treated Factor H composition is diafiltered against a solution containing from 20 mM to 40 mM phosphate buffer at a pH from 6.0 to 7.0. In one embodiment, the diafiltration buffer contains 32±5 mM phosphate buffer at a pH of 6.4±0.2. In one embodiment, the diafiltration buffer contains from 20 mM to 40 mM phosphate buffer and from 1 mM to 10 mM acetate at a pH from 6.0 to 7.0. In one embodiment, the diafiltration buffer contains 32±5 mM phosphate buffer and 5±2 mM acetate at a pH of 6.4±0.2. In one embodiment, the diafiltration buffer contains 32 mM phosphate buffer and 5 mM acetate at a pH of 6.4±0.1.

C. Chromatographic Enrichment

In some embodiments, the method for preparing an enriched Factor H composition includes at least one, preferably two or more, more preferably three or more chromatographic steps to further enrich the purity of the composition. Generally, any suitable chromatographic method may be employed to further enrich the Factor H composition (e.g., a recombinant Factor H composition, a Factor H composition extracted from Fraction I precipitate, or a Factor H composition extracted from Fraction II+III precipitate).

In some embodiments, the chromatographic step includes one or more of anion exchange chromatography (AEC), cation exchange chromatography (CEC), heparin affinity chromatography, mixed-mode chromatography, hydrophobic exchange chromatography (HIC), hydroxyapatite chromatography (HAP), immuno-affinity chromatography, size exclusion chromatography (SEC), or other suitable chromatographic step. Chromatographic steps may be performed in either batch or column mode.

In one embodiment, the method includes one or more of anion exchange, heparin affinity, and mixed mode chromatography steps. For example, in one embodiment, the method includes steps of: binding Factor H to an anion exchange resin; eluting Factor H from the anion exchange resin with an elution buffer, thereby forming an anion exchange eluate containing Factor H; binding Factor H to a heparin affinity resin; eluting Factor H from the heparin affinity resin with an elution buffer, thereby forming a heparin affinity eluate; binding Factor H to a mixed mode resin; and eluting Factor H from the mixed mode resin with an elution buffer, thereby forming a mixed mode eluate.

In some embodiments, the method includes all of anion exchange, heparin affinity, and mixed mode chromatography steps. The order of the chromatography steps may be varied, and may include intermediate steps, including without limitation, S/D treatment, nanofiltration, sterile filtration, heat treatment, buffer exchange, ultrafiltration, and/or diafiltration.

Generally, the conductivity/ionic strength and pH of the Factor H solution is adjusted to appropriate values prior to binding Factor H onto a chromatographic resin. The conductivity/ionic strength should be selected appropriately to promote the interaction between Factor H and the resin. The requirements for the conductivity/ionic strength of the solution will vary dependent upon factors such as the identity of the resin used (e.g., strong vs. weak anion exchange resin) and the starting purity of the solution. Various methods may be employed for reducing the conductivity/ionic strength of a Factor H composition, including without limitation, dilution of the composition with a solution having a low conductivity/ionic strength, precipitating Factor H from the starting composition and re-suspending in a buffer having lower conductivity/ionic strength, ultrafiltration/diafiltration, desalting and/or buffer exchange chromatography, and dialysis. In some embodiments, the chromatographic methods may include wash steps to remove loosely bound impurities from the chromatographic resin prior to elution of Factor H. In certain embodiments, Factor H may be eluted from a chromatography resin by gradient elution (e.g., with a salt gradient) or by step elution (e.g., with buffers having increasing conductivity/ionic strength).

1. Anion Exchange Chromatography

In some embodiments, an improved method is provided for enriching Factor H from a Factor H containing composition (e.g., a Factor H composition extracted from a plasma precipitate such as a Fraction I or Fraction II+III precipitate or a recombinant Factor H composition such as a cell culture supernatant or cell lysate containing Factor H), the method including binding Factor H to an anion exchange resin under low conductivity (e.g., 2 mS/cm to 5 mS/cm) and a mildly acidic pH (e.g., 6.4±0.3). The method also includes eluting Factor H from the anion exchange resin using either a combination of high conductivity (e.g., 20 mS/cm to 30 mS/cm) and a mildly acidic to neutral pH (e.g., 6.0 to 7.5) or a combination of moderate conductivity (e.g., 10 mS/cm to 20 mS/cm) and a neutral to mildly basic pH (e.g., 7.5 to 8.5).

Any suitable anion exchange resin may be used in the methods provided herein. Non-limiting examples of anion exchange resins suitable for use include diethylaminoethyl (DEAE), quaternary aminoethyl (QAE), and quaternary ammonium (Q) resins. In a preferred embodiment, the anion exchange resin used is DEAE Sepharose™ (diethylaminoethyl-Sepharose).

In some embodiments, Factor H is bound to a DEAE Sepharose™ resin in the presence of a low conductivity/ionic strength loading buffer. Typically, the column will be equilibrated with the same loading buffer or a compatible buffer with a conductivity/ionic strength similar to the loading buffer. In certain embodiments, the loading and/or equilibration buffer will have a conductivity of less than at or about 8 mS/cm. In some embodiments, the loading and/or equilibration buffer will have a conductivity of less than at or about 6 mS/cm. In some embodiments, the loading and/or equilibration buffer will have a conductivity of at or about 1 mS/cm to at or about 6 mS/cm. In yet other embodiments, the loading and/or equilibration buffer will have a conductivity of about 2±1 mS/cm, 3±1 mS/cm, 4±1 mS/cm, 5±1 mS/cm, 6±1 mS/cm, 7±1 mS/cm, or 8±1 mS/cm.

Optionally, after binding Factor H, the anion exchange resin may be washed with one or more buffers having a conductivity/ionic strength intermediate of the loading buffer and the elution buffer. In certain embodiments, a wash buffer may have a conductivity at or about between 2 mS/cm and 10 mS/cm. In some embodiments, the wash buffer may have a conductivity at or about between 5 mS/cm and 10 mS/cm. In some embodiments, the wash buffer will have a salt concentration, or conductivity/ionic strength corresponding to, at or about between 30 and 100 mM NaCl. In some embodiments, the wash buffer will have a salt concentration, or conductivity/ionic strength corresponding to that of a solution of, between about 40 mM and about 70 mM NaCl. In some embodiments, the wash buffer will have a salt concentration, or conductivity/ionic strength corresponding to that of a solution of about 30 mM NaCl, 35 mM NaCl, 40 mM NaCl, 45 mM NaCl, 50 mM NaCl, 55 mM NaCl, 60 mM NaCl, 65 mM NaCl, 70 mM NaCl, 75 mM NaCl, 80 mM NaCl, 85 mM NaCl, 90 mM NaCl, 95 mM NaCl, or 100 mM NaCl.

In some embodiments, the wash buffer includes 10-30 mM monobasic sodium phosphate (pH 6.4±0.3), sodium acetate or other suitable buffer, and 10-60 mM sodium chloride or other suitable salt. In some embodiments, the anion exchange resin is washed with a large amount of buffer to remove residual S/D reagents, for example with between 10 and 50 column volumes (e.g., 30±5 CV).

In certain embodiments, Factor H is eluted from the anion exchange resin (e.g., DEAE Sepharose™) with an elution buffer having suitable conductivity/ionic strength to disrupt the interaction between the resin and Factor H. In some embodiments, the elution buffer will not have a suitable conductivity/ionic strength to disrupt the interaction between the resin and a contaminant that binds the resin with higher affinity than does Factor H. In certain embodiments, the elution buffer will have a conductivity of at least about 12.5 mS/cm. In some embodiments, the elution buffer will have a conductivity of about 15 mS/cm. In some embodiments, the elution buffer will have a conductivity of about 17.5 mS/cm. In some embodiments, the elution buffer will have a salt concentration, or conductivity/ionic strength corresponding to a solution of, at least about 100 mM NaCl, preferably at least about 150 mM. In some embodiments, the elution buffer will have a salt concentration, or conductivity/ionic strength corresponding to a solution of, at least about 90 mM NaCl, 100 mM NaCl or at least about 95 mM NaCl, 100 mM NaCl, 105 mM NaCl, 110 mM NaCl, 115 mM NaCl, 120 mM NaCl, 125 mM NaCl, 130 mM NaCl, 140 mM NaCl, 150 mM NaCl, 160 mM NaCl, 170 mM NaCl, 180 mM NaCl, 190 mM NaCl, 200 mM NaCl, or more.

In one embodiment, the elution buffer has combination of moderate conductivity (e.g., 10 mS/cm to 20 mS/cm) and a neutral to mildly basic pH (e.g., 7.5 to 8.5). In one embodiment, the elution buffer has a conductivity of about 15±3 mS/cm and a pH of 8.0±0.3.

2. Heparin Affinity Chromatography

In some embodiments, an improved method is provided for enriching Factor H from a Factor H containing composition (e.g., a Factor H composition extracted from a plasma precipitate such as a Fraction I or Fraction II+III precipitate or a recombinant Factor H composition such as a cell culture supernatant or cell lysate containing Factor H), the method including binding Factor H to heparin affinity resin at moderate conductivity (e.g., 7 mS/cm to 11 mS/cm) and neutral pH (e.g., 7.2±0.3). The method also includes eluting Factor H from the heparin affinity resin using high conductivity (e.g., 25 mS/cm to 35 mS/cm) and a mildly basic pH (e.g., 8.0±0.3).

Any suitable heparin affinity resin may be used in the methods provided herein, for example, resins conjugated to a heparin ligand, derivative or mimetic of a heparin ligand, or heparin-like ligand (e.g., a sulfated glycosaminoglycan). In a preferred embodiment, the heparin affinity resin used is Heparin Sepharose™.

In some embodiments, Factor H is further enriched by heparin affinity chromatography, e.g., using a Heparin Sepharose™ resin. In one embodiment, the conductivity/ionic strength of the Factor H eluate is reduced by a suitable method, e.g., dilution, buffer exchange, dialysis, etc., and Factor H is bound to a heparin affinity resin. In certain embodiments, the conductivity of the anion exchange eluate is reduced to less than at or about 12 mS/cm. In some embodiments, the conductivity is reduced to less than at or about 10 mS/cm. In some embodiments, the conductivity is reduced to less than at or about 8 mS/cm. In some embodiments, the conductivity may be reduced to less than at or about 4 mS/cm, or less than at or about 5 mS/cm, 6 mS/cm, 7 mS/cm, 8 mS/cm, 9 mS/cm, 10 mS/cm, 11 mS/cm, or 12 mS/cm. In some embodiments, the salt concentration, or corresponding conductivity/ionic strength, of the anion exchange eluate is reduced to less than about 100 mM NaCl. In some embodiments, the salt concentration, or corresponding conductivity/ionic strength, is reduced to less than about 75 mM NaCl. In some embodiments, the salt concentration, or corresponding conductivity/ionic strength, is reduced to less than about 50 mM NaCl. In some embodiments, the salt concentration, or corresponding conductivity/ionic strength, is reduced less than about 20 mM NaCl, or less than about 25 mM NaCl, 30 mM NaCl, 40 mM NaCl, 50 mM NaCl, 60 mM NaCl, 70 mM NaCl, 80 mM NaCl, 90 mM NaCl, or 100 mM NaCl.

Optionally, after binding Factor H, the heparin affinity resin may be washed with one or more buffers having a conductivity/ionic strength intermediate of the loading buffer and the elution buffer. In certain embodiments, a wash buffer may have a conductivity at or about between 3 mS/cm and 12.5 mS/cm. In some embodiments, the wash buffer may have a conductivity at or about between 5 mS/cm and 10 mS/cm. In some embodiments, the wash buffer will have a salt concentration, or corresponding conductivity/ionic strength, of between about 30 mM and about 100 mM NaCl. In some embodiments, the wash buffer will have a salt concentration, or corresponding conductivity/ionic strength, of between about 30 mM and about 80 mM NaCl. In some embodiments, the wash buffer will have a salt concentration, or corresponding conductivity/ionic strength, of about 30 mM mM NaCl, 35 mM mM NaCl, 40 mM mM NaCl, 45 mM mM NaCl, 50 mM mM NaCl, 55 mM mM NaCl, 60 mM mM NaCl, 65 mM mM NaCl, 70 mM mM NaCl, 75 mM mM NaCl, 80 mM mM NaCl, 85 mM mM NaCl, 90 mM mM NaCl, 95 mM mM NaCl, or 100 mM NaCl.

In some embodiments, Factor H is eluted from the heparin affinity resin (e.g., DEAE Sepharose™) with an elution buffer having suitable conductivity/ionic strength to disrupt the interaction between the resin and Factor H. In some embodiments, the elution buffer will not have a suitable conductivity to disrupt the interaction between the resin and a contaminant that binds the resin with higher affinity than does Factor H. In certain embodiments, the elution buffer will have a conductivity of at least about 12 mS/cm. In certain embodiments, the elution buffer will have a salt concentration, or corresponding conductivity/ionic strength, of at least about 100 mM NaCl. In another embodiment, the elution buffer will have a salt concentration, or corresponding conductivity/ionic strength, of at least about 150 mM NaCl. In yet another embodiment, the elution buffer will have a salt concentration, or corresponding conductivity/ionic strength, of at least about 200 mM NaCl. In certain embodiments, the elution buffer will have a salt concentration, or corresponding conductivity/ionic strength, of at least about 90 mM NaCl or at least about 95 mM NaCl, 100 mM NaCl, 105 mM NaCl, 110 mM NaCl, 115 mM NaCl, 120 mM NaCl, 125 mM NaCl, 130 mM NaCl, 140 mM NaCl, 150 mM NaCl, 160 mM NaCl, 170 mM NaCl, 180 mM NaCl, 190 mM NaCl, 200 mM NaCl, 210 mM NaCl, 220 mM NaCl, 230 mM NaCl, 240 mM NaCl, 250 mM NaCl, 275 mM NaCl, 300 mM NaCl, 325 mM NaCl, 350 mM NaCl, or more.

3. Mixed Mode Chromatography

In some embodiments, an improved method is provided for enriching Factor H from a Factor H containing composition (e.g., a Factor H composition extracted from a plasma precipitate such as a Fraction I or Fraction II+III precipitate or a recombinant Factor H composition such as a cell culture supernatant or cell lysate containing Factor H), the method including binding Factor H to a mixed mode resin (e.g., having an aliphatic or aromatic ligand) at neutral to slightly basic pH (e.g., 6.5 to 8.5). The method also includes eluting Factor H from the mixed mode resin at acidic pH (e.g., 4.5±0.3). In some embodiments, the mixed mode resin includes a hexylamine ligand.

In some embodiments, the mixed mode resin includes an aliphatic ligand. Any suitable mixed mode resin that includes an aliphatic ligand may be used in the methods provided herein. For example, in some embodiments, the mixed mode resin includes an aliphatic amine (e.g., hexylamine) such as HEA HyperCel™ resin (Pall Corporation). In some embodiments, the mixed mode resin includes an aromatic ligand. Any suitable mixed mode resin that includes an aromatic ligand may be used in the methods provided herein. For example, in some embodiments, the mixed mode resin includes an aromatic amine (e.g., phenylpropylamine) such as PPA HyperCel™ resin (Pall Corporation).

In some embodiments, the method includes binding Factor H (e.g., Factor H extracted from plasma or recombinant Factor H) to the mixed mode resin at a pH at or about its isoelecetric point (e.g., 6.0). For example, in some embodiments, the binding pH is from about 6.0 to about 9.0. In some embodiments, the binding pH is from about 7.0 to about 9.0. In some embodiments, the binding pH is from about 7.5 to about 8.5. In other embodiments, the binding pH is about 7.0±0.5, 7.1±0.5, 7.2±0.5, 7.3±0.5, 7.4±0.5, 7.5±0.5, 7.6±0.5, 7.7±0.5, 7.8±0.5, 7.9±0.5, 8.0±0.5, 8.1±0.5, 8.2±0.5, 8.3±0.5, 8.4±0.5, or 8.5±0.5. In some embodiments, the binding pH is about 7.0±0.2, 7.1±0.2, 7.2±0.2, 7.3±0.2, 7.4±0.2, 7.5±0.2, 7.6±0.2, 7.7±0.2, 7.8±0.2, 7.9±0.2, 8.0±0.2, 8.1±0.2, 8.2±0.2, 8.3±0.2, 8.4±0.2, or 8.5±0.2. In a specific embodiment, binding of Factor H is performed at a pH of about 8.0.

In some embodiments, the method also includes washing the bound mixed mode resin after binding of Factor H and before elution. In some embodiments, the wash step is performed at a pH at or slightly around the isoelectric point of Factor H (e.g., 6.0). For example, in some embodiments, the wash is performed at a pH of from about 6.0 to about 7.5. In some embodiments, the wash is performed at a pH of from about 6.0 to about 7.0. In some embodiments, the wash is performed at pH 6.0±0.2, 6.1±0.2, 6.2±0.2, 6.3±0.2, 6.4±0.2, 6.5±0.2, 6.6±0.2, 6.7±0.2, 6.8±0.2, 6.9±0.2, 7.0±0.2, 7.1±0.2, 7.2±0.2, 7.3±0.2, 7.4±0.2, or 7.5±0.2. In a specific embodiment, the wash is performed at a pH of about 6.5.

In some embodiments, Factor H is eluted off of the mixed mode resin at a pH below the isoelectric point of Factor H (e.g., 6.0). For example, in some embodiments, the elution is performed at a pH of from about 4.0 and about 5.5. In some embodiments, the elution is performed at a pH of from about 4.3 to about 5.0. In some embodiments, the elution is performed at pH 4.0±0.2, 4.1±0.2, 4.2±0.2, 4.3±0.2, 4.4±0.2, 4.5±0.2, 4.6±0.2, 4.7±0.2, 4.8±0.2, 4.9±0.2, 5.0±0.2, 5.1±0.2, 5.2±0.2, 5.3±0.2, 5.4±0.2, or 5.5±0.2. In a specific embodiment, the wash is performed at a pH of about 4.4.

In some embodiments, where the Factor H composition is prepared from a Faction I precipitate, the Factor H composition is formulated, prior to binding to the mixed mode material, to pre-binding solution conditions including a conductivity from about 17 mS/cm to about 35 mS/cm and a pH from about 6.8 to about 8.0. In some embodiments, the pre-binding solution conditions include a conductivity from about 22 mS/cm to about 30 mS/cm. In some embodiments, the pre-binding solution conditions include a conductivity of about 25±3 mS/cm, 26±3 mS/cm, or 27±3 mS/cm. In some embodiments, the pre-binding solution conditions include a pH of about 7.4±0.5. In some embodiments, the pre-binding solution conditions include a pH of about 7.4±0.4. In some embodiments, the pre-binding solution conditions include a pH of about 7.4±0.3. In some embodiments, the pre-binding solution conditions include a pH of about 7.4±0.2. In some embodiments, the pre-binding solution conditions include a pH of about 7.4±0.1. In some embodiments, the pre-binding solution conditions include a conductivity from about 22 mS/cm to about 30 mS/cm and a pH of about 7.4±0.3.

In some embodiments, where the Factor H composition is prepared from a Faction I precipitate, the mixed mode material (e.g., mixed mode resin) is pre-equilibrated (e.g., prior to being contacted with Factor H) under pre-equilibration solution conditions including a conductivity from about 30 mS/cm to about 50 mS/cm and a pH from about 6.5 to about 7.5. In some embodiments, the pre-equilibration solution conditions include a conductivity from about 35 mS/cm to about 40 mS/cm. In some embodiments, the pre-equilibration solution conditions include a conductivity of about 35±5 mS/cm, 36±5 mS/cm, 37±5 mS/cm, 38±5 mS/cm, 39±5 mS/cm, 40±5 mS/cm, 41±5 mS/cm, 42±5 mS/cm, 43±5 mS/cm, 44±5 mS/cm, or 45±5 mS/cm. In some embodiments, the pre-equilibration solution conditions include a pH of about 7.0±0.5. In some embodiments, the pre-equilibration solution conditions include a pH of about 7.0±0.4. In some embodiments, the pre-equilibration solution conditions include a pH of about 7.0±0.3. In some embodiments, the pre-equilibration solution conditions include a pH of about 7.0±0.2. In some embodiments, the pre-equilibration solution conditions include a pH of about 7.0±0.1. In some embodiments, the pre-equilibration solution conditions include a conductivity from about 35 mS/cm to about 40 mS/cm and a pH of about 7.0±0.5. In some embodiments, the pre-equilibration solution includes a phosphate buffer and sodium chloride sufficient to provide the pre-equilibration solution conditions above. In a specific embodiment, the pre-equilibration solution includes about 100 mM phosphate buffer and about 300 mM sodium chloride.

In some embodiments, where the Factor H composition is prepared from a Faction I precipitate, the bound mixed mode material is washed (e.g., after being contacted with Factor H) under wash solution conditions including a conductivity from about 30 mS/cm to about 50 mS/cm and a pH from about 6.5 to about 7.5. In some embodiments, the wash solution conditions include a conductivity from about 35 mS/cm to about 40 mS/cm. In some embodiments, the wash solution conditions include a conductivity of about 35±5 mS/cm, 36±5 mS/cm, 37±5 mS/cm, 38±5 mS/cm, 39±5 mS/cm, 40±5 mS/cm, 41±5 mS/cm, 42±5 mS/cm, 43±5 mS/cm, 44±5 mS/cm, or 45±5 mS/cm. In some embodiments, the wash solution conditions include a pH of about 7.0±0.5. In some embodiments, the wash solution conditions include a pH of about 7.0±0.4. In some embodiments, the wash solution conditions include a pH of about 7.0±0.3. In some embodiments, the wash solution conditions include a pH of about 7.0±0.2. In some embodiments, the wash solution conditions include a pH of about 7.0±0.1. In some embodiments, the wash solution conditions include a conductivity from about 35 mS/cm to about 40 mS/cm and a pH of about 7.0±0.1. In some embodiments, the wash solution includes a phosphate buffer and sodium chloride sufficient to provide the wash solution conditions above. In a specific embodiment, the wash solution includes about 100 mM phosphate buffer and about 300 mM sodium chloride.

In some embodiments, where the Factor H composition is prepared from a Faction I precipitate, Factor H is eluted from the mixed mode material under elution solution conditions including a conductivity from about 5 mS/cm to about 12 mS/cm and a pH from about 4.2 to about 5.0. In some embodiments, the elution solution conditions include a conductivity from about 8 mS/cm to about 9 mS/cm. In some embodiments, the elution solution conditions include a conductivity of about 7±2 mS/cm, 8±2 mS/cm, 9±2 mS/cm, 10±2 mS/cm, 6±1 mS/cm, 7±1 mS/cm, 8±1 mS/cm, 9±1 mS/cm, 10±1 mS/cm, or 11±1 mS/cm. In some embodiments, the elution solution conditions include a pH of about 4.6±0.3. In some embodiments, the elution solution conditions include a pH of about 4.6±0.2. In some embodiments, the elution solution conditions include a pH of about 4.6±0.1. In some embodiments, the elution solution conditions include a conductivity from about 8 mS/cm to about 9 mS/cm and a pH from about 4.3 to about 4.8. In some embodiments, the elution solution includes an acetate buffer sufficient to provide the elution solution conditions above.

In some embodiments, where the Factor H composition is prepared from a Faction II+III silicon dioxide filter cake, the Factor H composition is formulated, prior to binding to the mixed mode material, to pre-binding solution conditions including a conductivity from about 13 mS/cm to about 35 mS/cm and a pH from about 6.6 to about 7.8. In some embodiments, the pre-binding solution conditions include a conductivity from about 18 mS/cm to about 30 mS/cm. In some embodiments, the pre-binding solution conditions include a conductivity of about 21±3 mS/cm, 22±3 mS/cm, 23±3 mS/cm, 24±3 mS/cm, 25±3 mS/cm, 26±3 mS/cm, or 27±3 mS/cm. In some embodiments, the pre-binding solution conditions include a pH of about 7.2±0.5. In some embodiments, the pre-binding solution conditions include a pH of about 7.2±0.4. In some embodiments, the pre-binding solution conditions include a pH of about 7.2±0.3. In some embodiments, the pre-binding solution conditions include a pH of about 7.2±0.2. In some embodiments, the pre-binding solution conditions include a pH of about 7.2±0.1. In some embodiments, the pre-binding solution conditions include a conductivity from about 18 mS/cm to about 30 mS/cm and a pH of about 7.2±0.3.

In some embodiments, where the Factor H composition is prepared from a Faction II+III silicon dioxide filter cake, the mixed mode material (e.g., mixed mode resin) is pre-equilibrated (e.g., prior to being contacted with Factor H) under pre-equilibration solution conditions including a conductivity from about 15 mS/cm to about 30 mS/cm and a pH from about 6.5 to about 7.5. In some embodiments, the pre-equilibration solution conditions include a conductivity from about 20 mS/cm to about 23 mS/cm. In some embodiments, the pre-equilibration solution conditions include a conductivity of about 20±5 mS/cm, 21±5 mS/cm, 22±5 mS/cm, 23±5 mS/cm, 24±5 mS/cm, or 25±5 mS/cm. In some embodiments, the pre-equilibration solution conditions include a pH of about 7.0±0.5. In some embodiments, the pre-equilibration solution conditions include a pH of about 7.0±0.4. In some embodiments, the pre-equilibration solution conditions include a pH of about 7.0±0.3. In some embodiments, the pre-equilibration solution conditions include a pH of about 7.0±0.2. In some embodiments, the pre-equilibration solution conditions include a pH of about 7.0±0.1. In some embodiments, the pre-equilibration solution conditions include a conductivity from about 35 mS/cm to about 40 mS/cm and a pH of about 7.0±0.5. In some embodiments, the pre-equilibration solution conditions include a conductivity from about 35 mS/cm to about 40 mS/cm and a pH of about 7.0±0.5. In some embodiments, the pre-equilibration solution includes a phosphate buffer and sodium chloride sufficient to provide the pre-equilibration solution conditions above. In a specific embodiment, the pre-equilibration solution includes about 100 mM phosphate buffer and about 100 mM sodium chloride.

In some embodiments, where the Factor H composition is prepared from a Faction II+III silicon dioxide filter cake, the bound mixed mode material is washed (e.g., after being contacted with Factor H) under wash solution conditions including a conductivity from about 10 mS/cm to about 20 mS/cm and a pH from about 6.0 to about 6.9. In some embodiments, the wash solution conditions include a conductivity from about 13 mS/cm to about 17 mS/cm. In some embodiments, the wash solution conditions include a conductivity of about 14±1 mS/cm, 15±1 mS/cm, or 16±1 mS/cm. In some embodiments, the wash solution conditions include a pH of about 6.4±0.2. In some embodiments, the wash solution conditions include a pH of about 6.4±0.1. In some embodiments, the wash solution conditions include a pH from about 6.4 to about 6.5. In some embodiments, the wash solution conditions include a conductivity of about 15 mS/cm and a pH from about 6.4 to about 6.5. In some embodiments, the wash solution includes an acetate buffer sufficient to provide the wash solution conditions above. In a specific embodiment, the wash solution includes about 200 mM acetate.

In some embodiments, where the Factor H composition is prepared from a Faction II+III silicon dioxide filter cake, Factor H is eluted from the mixed mode material under elution solution conditions including a conductivity from about 3 mS/cm to about 10 mS/cm and a pH from about 4.2 to about 4.7. In some embodiments, the elution solution conditions include a conductivity from about 6 mS/cm to about 7 mS/cm. In some embodiments, the elution solution conditions include a conductivity of about 5±2 mS/cm, 6±2 mS/cm, 7±2 mS/cm, 8±2 mS/cm, 4±1 mS/cm, 5±1 mS/cm, 6±1 mS/cm, 7±1 mS/cm, 8±1 mS/cm, or 9±1 mS/cm. In some embodiments, the elution solution conditions include a pH of about 4.4±0.2. In some embodiments, the elution solution conditions include a pH of about 4.4±0.1. In some embodiments, the elution solution conditions include a conductivity from about 6 mS/cm to about 7 mS/cm and a pH from about 4.3 to about 4.5. In some embodiments, the elution solution includes an acetate buffer sufficient to provide the elution solution conditions above. In a specific embodiment, the wash solution includes about 120 mM acetate.

In some embodiments, a heparin affinity eluate is loaded onto the mixed mode resin (e.g., a mixed mode resin having a hexylamine ligand). In certain embodiments, the heparin eluate will be loaded onto the mixed mode resin without adjusting the pH or conductivity/ionic strength of the solution prior to loading. In some embodiments, the heparin affinity eluate is loaded without adjustment (e.g., loaded directly without adjusting the pH or conductivity/ionic strength of the solution) where the heparin affinity eluate has a pH above the isoelectric point of Factor H (e.g., above pH 6.0, or above pH 6.5, about 6.5 to 9.0, about 7.0 to 9.0, about 7.5 to 8.5).

D. Virus Inactivation and Removal

In some embodiments, the methods provided herein for the preparation of an enriched Factor H composition include at least one, preferably at least two, more preferably three different viral inactivation and/or removal steps. Non-limiting examples of viral inactivation or removal steps that may be employed with the methods provided herein include, solvent detergent treatment (Horowitz et al., Blood Coagul Fibrinolysis 1994 (5 Suppl 3):S21-S28 and Kreil et al., Transfusion 2003 (43):1023-1028, the disclosures of which are hereby expressly incorporated herein by reference in their entireties for all purposes), nanofiltration (Hamamoto et al., Vox Sang 1989 (56) 230-236 and Yuasa et al., J Gen Virol. 1991 (72 (pt 8)):2021-2024, the disclosures of which are hereby expressly incorporated herein by reference in their entireties for all purposes), and low pH incubation at high temperatures (Kempf et al., Transfusion 1991 (31) 423-427 and Louie et al., Biologicals 1994 (22):13-19, the disclosure of which is hereby expressly incorporated herein by reference in its entirety for all purposes). In some embodiments, the methods provided herein include S/D treatment and nanofiltration steps.

Viral inactivation or removal may be performed on a final enriched Factor H composition and/or on any intermediate Factor H compositions generated during the manufacturing process. For example, in one embodiment, a viral inactivation or removal step may be performed on a Fraction I precipitate extract, a Fraction II+III silicon dioxide filter cake extract, a cell culture supernatant, an anion exchange eluate, a heparin affinity eluate, a mixed mode chromatography eluate, an ultrafiltration or diafiltration product, etc.

In one embodiment, a solvent and detergent treatment is performed prior to the first chromatographic enrichment step and nonfiltration is performed prior to final formulation of the Factor H composition.

1. Solvent and Detergent (S/D) Treatment

In order to inactivate various viral contaminants which may be present in plasma-derived or recombinant products, one or more Factor H intermediate compositions may be subjected to a solvent detergent (S/D) treatment. Methods for the detergent treatment of plasma-derived fractions are well known in the art (for review see, Pelletier J P et al., Best Pract Res Clin Haematol. 2006; 19(1):205-42, the disclosure of which is expressly incorporated by reference herein in its entirety for all purposes). Generally, any standard S/D treatment may be used in conjunction with the methods provided herein. For example, an exemplary protocol for an S/D treatment is provided below.

In some embodiments, Triton X-100, Tween-20, and tri(n-butyl)phosphate (TNBP) are added to a Factor H intermediate composition at final concentrations of at or about 1.0%, 0.3%, and 0.3%, respectively. The mixture is then stirred at a temperature of between about 18° C. and about 25° C. for at least about an hour.

In one embodiment, the S/D reagents (e.g., Triton X-100, Tween-20, and TNBP) are added by spraying rather than by fluent addition. In other embodiments, the detergent reagents may be added as solids to the Factor H intermediate solution, which is being mixed to ensure rapid distribution of the S/D components. In certain embodiments, it is preferable to add solid reagents by sprinkling the solids over a delocalized surface area of the filtrate such that local overconcentration does not occur, such as in fluent addition. In another embodiment, the Factor H containing solution is pumped into a tank where the SD-reagents are already present either in concentrated or diluted form.

2. Nanofiltration

In some embodiments, the methods provided herein include nanofiltration of an enriched Factor H composition, or an intermediate thereof, using a suitable nanofiltration device. In certain embodiments, the nanofiltration device will have a mean pore size of from about 15 nm to about 100 nm. Examples of nanofilters suitable for this use include, without limitation, DVD, DV 50, DV 20 (Pall), Viresolve NFP, Viresolve NFR (Millipore), Planova 15N, 20N, 35N, and 75N (Planova). In some embodiments, the nanofilter has a mean pore size of from about 15 nm to about 72 nm, or from about 19 nm to about 35 nm, or about 15 nm, 19 nm, 35 nm, or 72 nm. In some embodiments, the nanofilter has a mean pore size of about 19 nm, such as an Asahi PLANOVA 20N filter, or equivalent thereof.

3. Incubation at Low pH

In some embodiments, the enriched Factor H composition, or an intermediate thereof, is incubated at low pH to reduce or inactivate the viral load of the composition. In one embodiment, this is achieved by adjusting the pH of the of the composition to low pH, for example, less than at or about 6.0, and incubating for at least about a week prior to releasing the composition. In a preferred embodiment, the pH of the bulk solution is adjusted to less than at or about 5.5 prior to incubation. In a more preferred embodiment, the pH of the solution is lowered to less than at or about 5.0 prior to incubation. In certain embodiments, the pH of the solution is lowered to less than at or about 6.0 or less than at or about 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, or lower prior to incubation.

In some embodiments, the enriched Factor H composition, or an intermediate thereof, is incubated for at least about one week, or at least about 2, 3, 4, or more weeks, or for at least about 1, 2, 3, or more months. In some embodiments, the composition is incubated at a temperature above about 20° C., or above about 25° C., or above about 30° C. In some embodiments, the composition is incubated at a temperature of at or about 20° C., or at or about 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., or higher.

4. Lyophilization and Heat Treatment

In some embodiments, in which the enriched Factor H composition is lyophilized, the method for preparing the composition includes heat treatment of the lyophilized composition. Heat treatments for the inactivation of viruses in compositions of blood factors are well known in the art (for example, see, Piszkiewicz et al., Thromb Res. 1987 Jul. 15; 47(2):235-41; Piszkiewicz et al., Curr Stud Hematol Blood Transfus. 1989; (56):44-54; Epstein and Fricke, Arch Pathol Lab Med. 1990 March; 114(3):335-40, the disclosures of which are hereby expressly incorporated by reference in their entireties for all purposes).

E. Ultrafiltration and Diafiltration

In some embodiments, the methods provided herein include an ultrafiltration step to concentrate and/or formulate the enriched Factor H composition. In some embodiments, ultrafiltration is performed using a cassette (e.g., with an open channel screen) and an ultrafiltration membrane having a nominal molecular weight cut off (NMWCO) of no more than about 150 kDa or no more than about 140, 130, 120, 100, 90, 80, 70, 60, 50, 40, or 30 kDa. In some embodiments, the ultrafiltration membrane has a NMWCO of about 50 kDa. In one embodiment, the ultrafiltration membrane has a NMWCO of about 70 kDa. In one embodiment, the ultrafiltration membrane has a NMWCO of about 30 kDa.

In some embodiments, the Factor H solution is concentrated to a final protein concentration of at or about between 0.5% and 25% (w/v), or at or about between 1% and 25% (w/v), or at or about between 2% and 20% (w/v), or at or about between 3% and 15% (w/v), or at or about between 5% and 10% (w/v), or at or about between 9% and 12%, or at or about between 3% and 7% (w/v), or at or about between 8% and 14% (w/v), or at or about between 4% and 6%, or to a final concentration of at or about 0.1%, 0.25%, 0.5%, 1%, 2%, 3%, 4%, 5%, or 6%, 7%, 8%, 9%, 10%, 11%, 12%, 13%, 14%, 15%, 16%, 17%, 18%, 19%, 20%, 21%, 22%, 23%, 24%, 25%, or higher.

In some embodiments, prior to and/or after ultrafiltration, buffer exchange may be performed by diafiltration against a solution suitable for intravenous, intramuscular, intraocular, subcutaneous, or other appropriate route for administration of Factor H. Typically, the minimum exchange volume is at least about 3 times the original concentrate volume or at least about 4, 5, 6, 7, 8, 9, or more times the original concentrate volume.

VII. Factor H Compositions

Factor H compositions have been described for the treatment of certain complement related disorders. (See, for example, U.S. Patent Publication No. US 2009/0118163 and European Patent Application No. EP 0 222 611 A2, the disclosures of which are hereby expressly incorporated herein by reference in their entireties for all purposes.)

In one aspect, enriched Factor H compositions prepared according to any of the methods described herein are provided. In some embodiments, the enriched Factor H composition is an aqueous composition. In some embodiments, the enriched Factor H composition is formulated for pharmaceutical administration, for example by intravenous, intramuscular, intraocular, subcutaneous, or any other appropriate route for therapeutic administration of Factor H.

In some embodiments, Factor H is provided in a therapeutically effective dose between about 0.05 mg/mL and about 50 mg/mL. In some embodiments, Factor H is present at a concentration of between about 0.1 mg/mL and about 25 mg/mL. In some embodiments, Factor H is present at a concentration of between about 0.1 mg/mL and about 10 mg/mL. In some embodiments, Factor H is present at a concentration of between about 0.1 mg/mL and about 5 mg/mL. In another embodiment, Factor H is present at a concentration of between about 0.1 mg/mL and about 2 mg/mL. In another embodiment, Factor H is present at a concentration of between about 1 mg/mL and about 2 mg/mL. In yet other embodiments, Factor H may be present at about 0.01 mg/mL, or at about 0.02 mg/mL, 0.03 mg/mL, 0.04 mg/mL, 0.05 mg/mL, 0.06 mg/mL, 0.07 mg/mL, 0.08 mg/mL, 0.09 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10.0 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 22.5 mg/mL, 25 mg/mL, 27.5 mg/mL, 30 mg/mL, 35 mg/mL, 40 mg/mL, 45 mg/mL, 50 mg/mL, or a higher concentration.

In some embodiments, the concentration of a Factor H formulation may be determined by spectroscopy (e.g., total protein measured at A280) or other bulk determination (e.g., Bradford assay, silver stain, weight of a lyophilized powder, etc.). In some embodiments, the concentration of Factor H may be determined by a Factor H ELISA assay (e.g., mg/mL antigen).

In some embodiments, a pharmaceutical Factor H composition has a purity of at least 80% Factor H. In some embodiments, a pharmaceutical Factor H composition has a purity of at least 85% Factor H. In some embodiments, a pharmaceutical Factor H composition has a purity of at least 90% Factor H. In some embodiments, a pharmaceutical Factor H composition has a purity of at least 95% Factor H. In some embodiments, a pharmaceutical Factor H composition has a purity of at least 98% Factor H. In some embodiments, a pharmaceutical Factor H composition has a purity of at least 99% Factor H.

Pharmaceutical carriers and excipients as well as suitable pharmaceutical formulations are well known in the art (see, for example "Pharmaceutical Formulation Development of Peptides and Proteins," Frokjaer et al., Taylor & Francis (2000) or "Handbook of Pharmaceutical Excipients", 3rd edition, Kibbe et al., Pharmaceutical Press (2000)).

In some embodiments, the enriched Factor H pharmaceutical composition is formulated in lyophilized or stable soluble form. The Factor H pharmaceutical composition may be lyophilized by a variety of procedures known in the art. Lyophilized formulations are reconstituted prior to use by the addition of one or more pharmaceutically acceptable diluents such as sterile water for injection or sterile physiological saline solution.

Formulations of the enriched Factor H composition are delivered to the individual by any pharmaceutically suitable means of administration. Various delivery systems are known and can be used to administer the composition by any convenient route. In some embodiments, the compositions of the invention are administered systemically. For systemic use, in accordance with some embodiments, Factor H is formulated for parenteral (e.g. intravenous, subcutaneous, intramuscular, intraperitoneal, intracerebral, intrapulmonar, intranasal, intravitreal, or transdermal) or enteral (e.g., oral, vaginal or rectal) delivery according to conventional methods. The formulations can be administered continuously by infusion or by bolus injection. Some formulations encompass slow release systems. Preferred routes of administration will depend upon the indication being treated, managed, or prevented. For example, in one embodiment, wherein Factor H is administered for the treatment of AMD, the preferred route of administration will be intravitreal. In a second embodiment, wherein Factor H is being administered for the treatment or management of aHUS, the preferred route of administration will be intravenous. A skilled physician will readily be able to determine the preferred route of administration for the particular affliction being treated, managed, or prevented.

VIII. Methods of Treatment

In one aspect, methods for treating a disease or disorder associated with a Factor H dysfunction or abnormal alternative pathway complement activity in a subject in need thereof are provided by administering a therapeutically effective dose of an enriched Factor H composition provided herein.

In some embodiments, the present disclosure provides a therapeutically effective dose of an enriched Factor H composition prepared by a method disclosed herein for use in a method for treating a disease associated with Factor H dysfunction in a subject in need thereof. In some embodiments, the disease or disorder associated with a Factor H dysfunction is selected from atypical haemolytic uremic syndrome (aHUS), age-related macular degeneration (AMD), membranoproliferative glomulonephritis type II (MPGNII), myocardial infarction, coronary heart disease/coronary artery disease (CAD/CHD), and Alzheimer's disease. In one particular embodiment, the disease is atypical haemolytic uremic syndrome (aHUS). In another particular embodiment, the disease is age-related macular degeneration (AMD). In yet another particular embodiment, the disease is membranoproliferative glomulonephritis type II (MPGNII).

In some embodiments, the present disclosure provides a therapeutically effective dose of an enriched Factor H composition prepared by a method disclosed herein for use in a method for treating a disease associated with abnormal alternative pathway complement activity in a subject in need thereof. In some embodiments, the disease or disorder associated with abnormal alternative pathway complement activity is selected from an autoimmune disease (such as rheumatoid arthritis, IgA nephropathy, asthma, systemic lupus erythematosus, multiple sclerosis, Anti-Phospholipid syndrome, ANCA-associated vasculitis, pemphigus, uveitis, myathemia gravis, Hashimoto's thyroiditis), a renal disease (such as IgA nephropathy, hemolytic uremic syndrome, membranoproliferative glomerulonephritis) asthma, Alzheimer disease, adult macular degeneration, proximal nocturnal hemoglobinuria, abdominal aortic aneurism, ischemia reperfusion injury, sepsis, and solid organ transplant.

In some embodiments, an enriched Factor H pharmaceutical composition, as provided herein, is administered alone. In some embodiments, an enriched Factor H pharmaceutical composition, as provided herein, is administered in conjunction with other therapeutic agents. In some embodiments, the additional therapeutic agents may be incorporated as part of the same pharmaceutical composition as Factor H. In some embodiments, the additional therapeutic agents may be formulated as a separate pharmaceutical composition as Factor H.

In accordance with some embodiments, the time needed to complete a course of treatment with a Factor H composition can be determined by a physician and may range from as short as one day to more than a year.

An effective amount of a Factor H preparation is administered to the subject by any suitable means to treat the disease or disorder. For example, in certain embodiments, Factor H may be administered by intravenous, intraocular, subcutaneous, and/or intramuscular means. In a preferred embodiment, a method for treating age-related macular degeneration in a subject in need thereof is provided comprising the intraocular administration of a Factor H composition to the patient.

In certain embodiments, the Factor H compositions provided herein can be administered either systemically or locally. Systemic administration includes: oral, transdermal, subdermal, intraperitioneal, subcutaneous, transnasal, sublingual, or rectal. The most preferred systemic route of administration is oral. Local administration for ocular administration includes: topical, intravitreal, periocular, transscleral, retrobulbar, juxtascleral, sub-tenon, or via an intraocular device. Preferred methods for local delivery include transscleral delivery to the macula by posterior juxtascleral administration; via intravitreal injection; or via cannula, such as that described in U.S. Pat. No. 6,413,245, the disclosure of which is incorporated by reference herein in its entirety for all purposes. Alternatively, Factor H may be delivered via a sustained delivery device implanted intravitreally or transsclerally, or by other known means of local ocular delivery.

In certain embodiments, the term "effective amount" refers to an amount of a Factor H preparation that results in an improvement or remediation of disease or condition in the subject. An effective amount to be administered to the subject can be determined by a physician with consideration of individual differences in age, weight, the disease or condition being treated, disease severity and response to the therapy. In certain embodiments, a Factor H preparation can be administered to a subject at dose of between about 0.1 mg/kilogram and about 2000 mg/kilogram per administration. In certain embodiments, the dose may be at least about 0.1 mg/kg, at least about 0.2 mg/kg, at least about 0.5 mg/kg, or at least about 1.0 mg/kg, 2.0 mg/kg, 3.0 mg/kg, 4.0 mg/kg, 5.0 mg/kg, 7.5 mg/kg, 70 mg/kg, 15 mg/kg, 20 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, or 2000 mg/kg. The dosage and frequency of Factor H treatment will depend upon, among other factors, the disease or condition being treated and the severity of the disease or condition in the patient.

In some embodiments, Factor H is administered at an absolute dosage, rather than a dosage dependent upon the weight of the individual. For example, in some embodiments, Factor H is administered intravitreally at a dosage set based on the identity and severity of the particular indication being treated (e.g., macular degeneration or age-related macular degeneration). In some embodiments, Factor H is administered at a fixed dose of from about 0.1 mg to about 200 g. In some embodiments, Factor H is administered at a fixed dose of from about 0.1 mg to about 20 g. In some embodiments, Factor H is administered at a fixed dose of from about 0.1 mg to about 2 g. In some embodiments, Factor H is administered at a fixed dose of from about 0.1 mg to about 200 mg. In some embodiments, Factor H is administered at a fixed dose of from about 0.1 mg to about 20 mg. In some embodiments, Factor H is administered at a fixed dose of from about 0.1 mg to about 10 mg. In some embodiments, Factor H is administered at a fixed dose of from about 0.1 mg to about 5 mg. In some embodiments, Factor H is administered intravitreally at a fixed dose of about 0.1 mg to about 10 mg. In some embodiments, Factor H is administered intravitreally at a fixed dose of about 0.1 mg to about 5 mg. In some embodiments, Factor H is administered intravitreally at a fixed dose of about 1 mg to about 3 mg. In some embodiments, Factor H is administered intravitreally at a fixed dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6, mg 2.7 mg, 2.8 mg, 2.9 mg, 3.0 mg, 2.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10.0 mg or more.

IX. Examples

The following examples are provided by way of illustration only and not by way of limitation. Those of skill in the art will readily recognize a variety of non-critical parameters that could be changed or modified to yield essentially the same or similar results.

Figure 1:
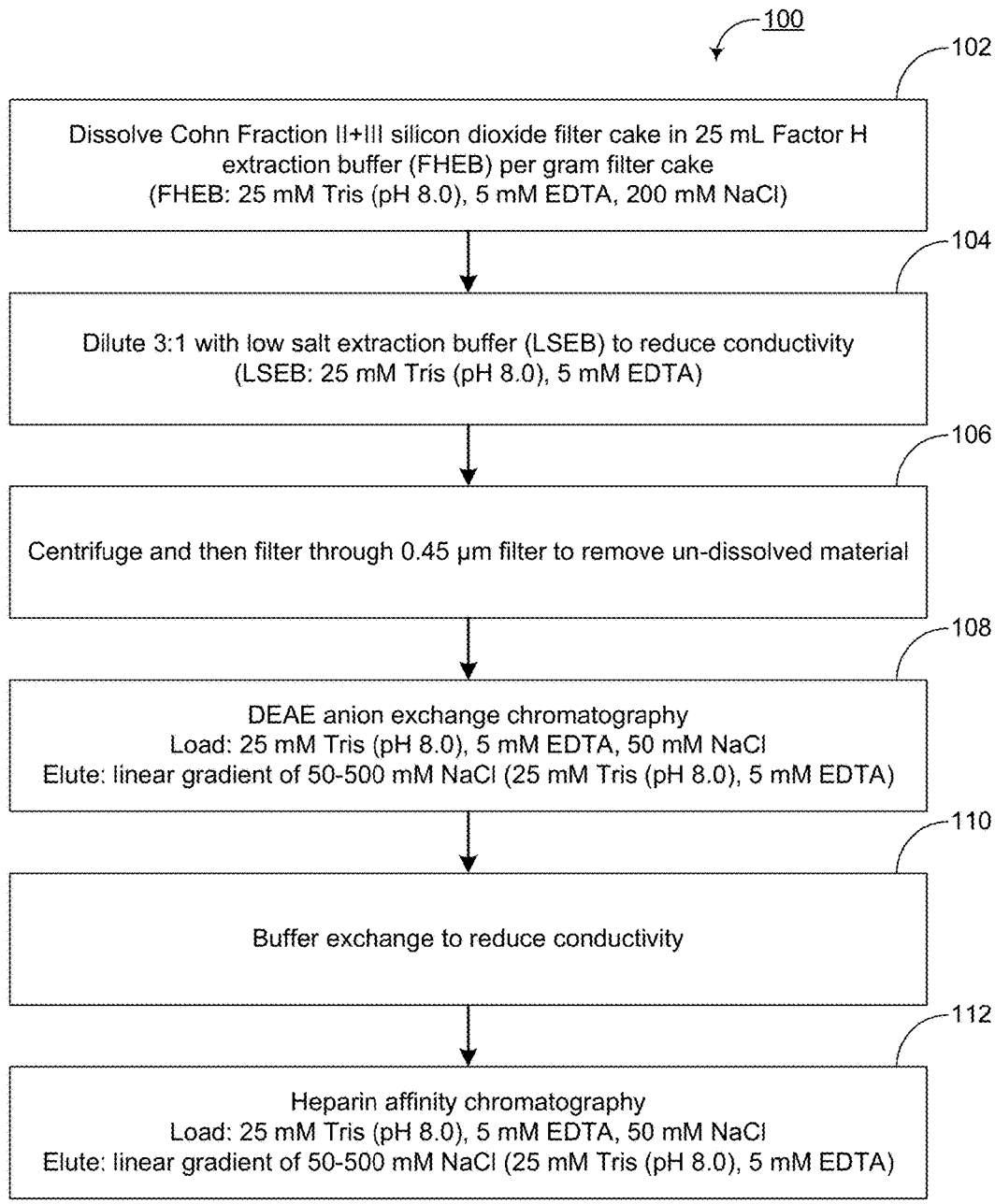
FIG. 1 illustrates a method provided in U.S. Pat. No. 8,304,524 for purifying Factor H from Cohn Fraction II+III silicon dioxide filter cake.

Example 1—Purification of Factor H from Cohn Fraction II+III Silicon Dioxide Filter Cake As reported in U.S. Pat. No. 8,304,524, Factor H can be purified from Cohn Fraction II+III silicon dioxide filter cake, a byproduct of the process used to manufacture pooled human immunoglobulin G compositions. The method used for Factor H purifications from Cohn Fraction II+III silicon dioxide filter cake in U.S. Pat. No. 8,304,524 is outlined as method 100 in FIG. 1. Briefly, method 100 includes: dissolving (102) the filter cake to extract Factor H, reducing the conductivity (102) of the dissolved solution, centrifuging and filtering (106) to clarify the dissolved solution, enriching Factor H (108) by DEAE anion exchange chromatography, reducing the conductivity (110) of the DEAE eluate, and enriching Factor H (112) by heparin affinity chromatography.

Example 2—Stability Characterization of Factor H Purified from Fraction II+III Silicon Dioxide Filter Cake During the purification of Factor H from Cohn Fraction II+III silicon dioxide filter cake, as described in Example 1, it was noticed that under reducing conditions, e.g., conditions that eliminate disulfide bonds, purified Factor H resolved as two major bands during SDS-PAGE analysis, suggesting that Factor H was being proteolytically clipped (e.g., the Factor H polypeptide backbone was being broken at a discreet location). Due to the extensive network of disulfide bonds that stabilize the tertiary structure of Factor H, this proteolytic clipping was not observed under non-reducing conditions.

Figure 2:
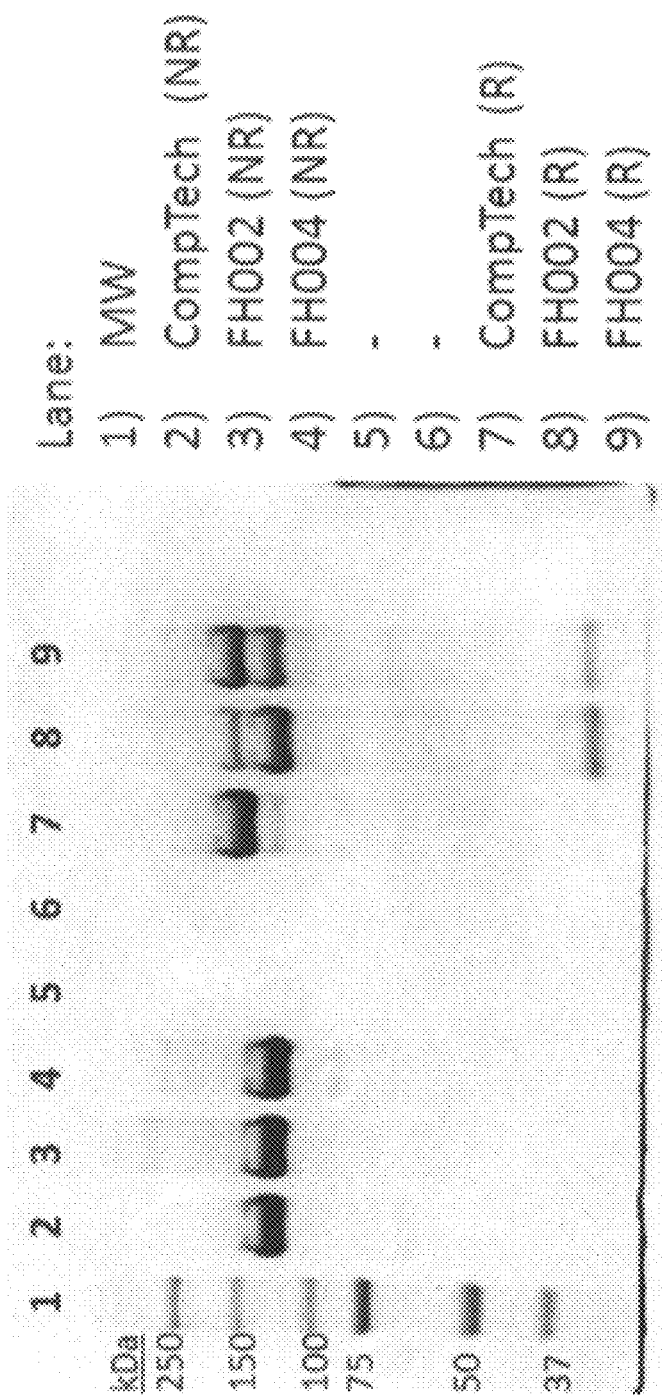
FIG. 2 shows an SDS-PAGE analysis of the structure of reduced (R) and non-reduced (NR) recombinant Factor H (CompTech) and Factor H prepared from Fraction II+III silicon dioxide filter cake (FH002 and FH004).

For example, the SDS-PAGE gel reproduced in FIG. 2 shows that under non-reducing condition (NR), the migration pattern of Factor H purified from Cohn Fraction II+III silicon dioxide filter cake (FH002 and FH004), as described in Example 1, is indistinguishable from the migration pattern of a plasma-derived Factor H standard (CompTech, Tyler, Tex.), and appears as a single band of the gel (compare Fraction II+III purified Factor H in lanes 3 and 4 to plasma-derived Factor H in lane 2). However, under reducing the conditions, the Factor H purified from Cohn Fraction II+III silicon dioxide filter cake migrates as three distinct bands (FIG. 7, lanes 8 and 9), including a doublet centered around 140 kDa (e.g., corresponding to full-length and the large fragment of the proteolytically clipped Factor H) and a single band migrating around 35 kDa (e.g., corresponding to the small fragment of the proteolytically clipped Factor H). In contrast, the plasma-derived Factor H control (FIG. 7, lane 7) migrates largely as a single band around 155 kDa (e.g., corresponding to the full-length Factor H). Without being bound by theory, the proteolytic clipping of Factor H purified from Cohn Fraction II+III silicon dioxide filter cake was attributed to amidolytic proteases known to be present in Cohn Fraction II+III silicon dioxide filter cakes.

Figure 3:
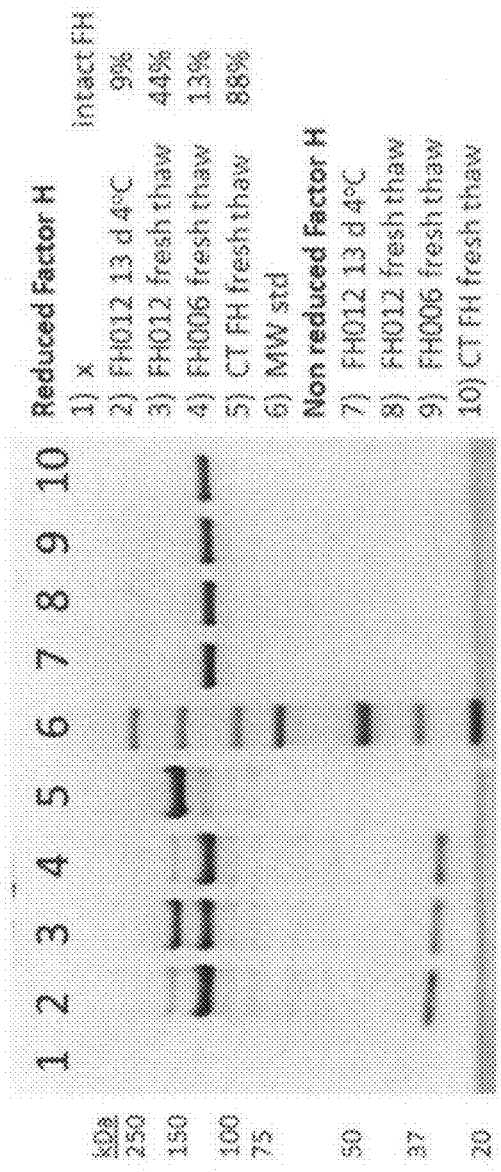
FIG. 3 shows an SDS-PAGE analysis of the structure of recombinant Factor H (CompTech) and Factor H prepared from Fraction II+III silicon dioxide filter cake (FH006 and FH012) treated with (13 d 4° C.) and without (fresh thaw) incubation for 13 days at 4° C.

Example 3—Characterization of Proteolytic Activity in Factor H Compositions Purified from Fraction II+III Silicon Dioxide Filter Cake The source of the observed proteolytic clipping of Factor H in compositions enriched from Cohn Fraction II+III silicon dioxide filter cake was further investigated. An experiment testing the stability of Factor H upon incubation at 4° C. for an extended time demonstrated that Factor H compositions purified from Cohn Fraction II+III silicon dioxide filter cake (lots FH002 and FH004), as described in Example 1, contained proteolytic activities. Briefly, an aliquot of Factor H isolated from Cohn Fraction II+III silicon dioxide filter cake (lot FH012) was incubated for 13 days at 4° C. The structure of the incubated Factor H (FH12 13 d 4° C., lane 2) is compared in FIG. 3 to the structure of: Factor H from the same purification lot (FH012 fresh thaw, lane 3); Factor H from an equivalent lot purified from Cohn Fraction II+III silicon dioxide filter cake (FH006 fresh thaw, lane 4); and plasma-derived Factor H (CompTech, Tyler, Tex., lane 5), by SDS PAGE analysis of the reduced protein. Quantitation of the respective full length Factor H bands (e.g., the bands migrating at about 155 kDa) in FIG. 3 reveals that incubation of the purified Factor H composition results in further proteolytic clipping. For example, FH012 incubated at 4° C. for 13 days (lane 2) has nearly five times less fully intact Factor H (9% intact Factor H) than does freshly thawed FH012 (lane 3, 44% intact Factor H). Coupled with the concurrent increase in the intensity of the 120 kDa (corresponding to the larger proteolytic product) and 35 kDa (corresponding to the smaller proteolytic product) bands, these data evidence the presence of proteolytic enzymes in the purified Factor H composition.

The presence of amidolytic activity in Factor H lot FH012 was further confirmed by thromboelastographic (TEG) measurements showing that FH012 has a decreased clotting time as compared to normal citrated blood. Furthermore, western blotting analysis shows that Factor XI, an amidolytic component of the coagulation cascade, is present in Factor H lot FH012.

Figure 4:
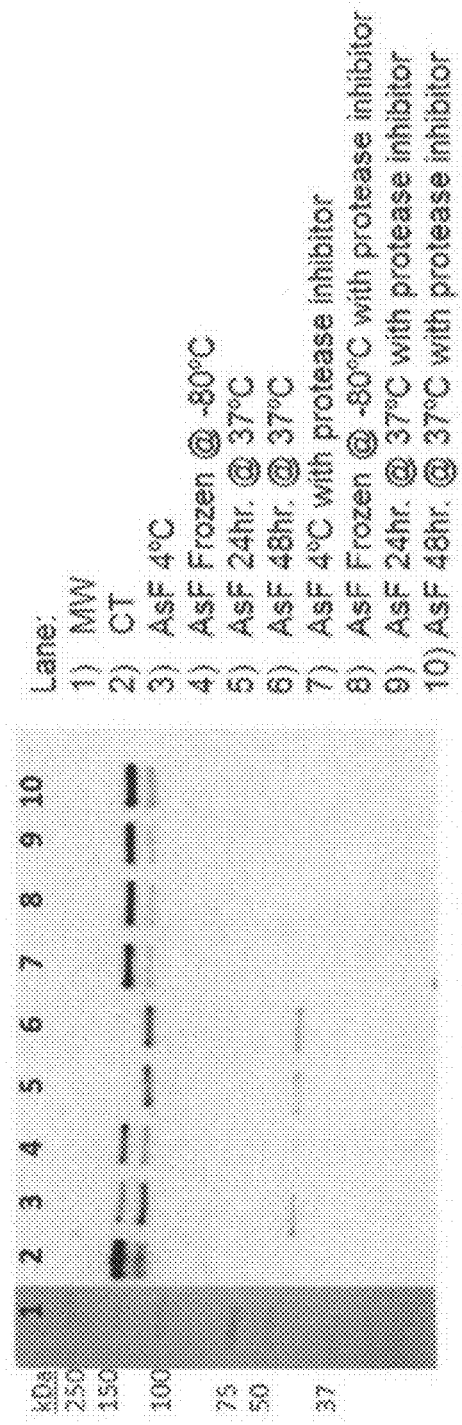
FIG. 4 shows an SDS-PAGE analysis of the stability of Factor H in suspended Cohn Fraction II+III silicon dioxide filter cake upon incubation at 37° C. for 24 or 48 hours in the presence or absence of protease inhibitors.

The proteolytic activity in Factor H lot FH012 was also observed in Cohn Fraction II+III silicon dioxide filter cake starting material. As shown in FIG. 4, Factor H present in Cohn Fraction II+III silicon dioxide filter cake starting material was completely clipped to the 120 kDa fragment when the filter cake extract is incubated for 24 hours at 37° C. (lane 5). The proteolytic clipping was nearly eliminated by the addition of a protease inhibitor cocktail (Thermo Scientific, Rockford, Ill.), even after a 48 hour incubation at 37° C. (lane 10).

Figure 5A:
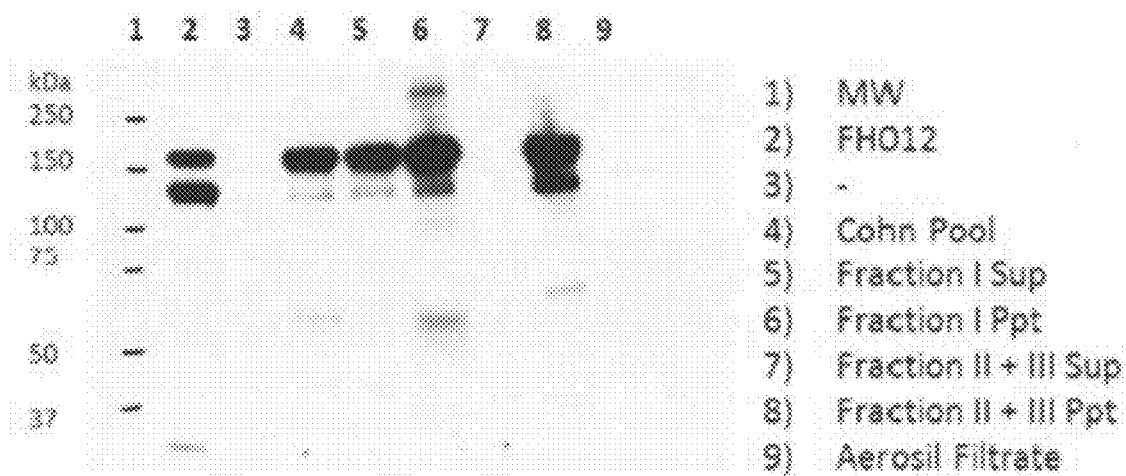
FIGS. 5A and 5B show an anti-Factor H western blot analysis (FIG. 5A) of Factor H plasma fractions formed during the manufacture of pooled human IgG and albumin according to the fractionation scheme illustrated in FIG. 5B.
Figure 5B:
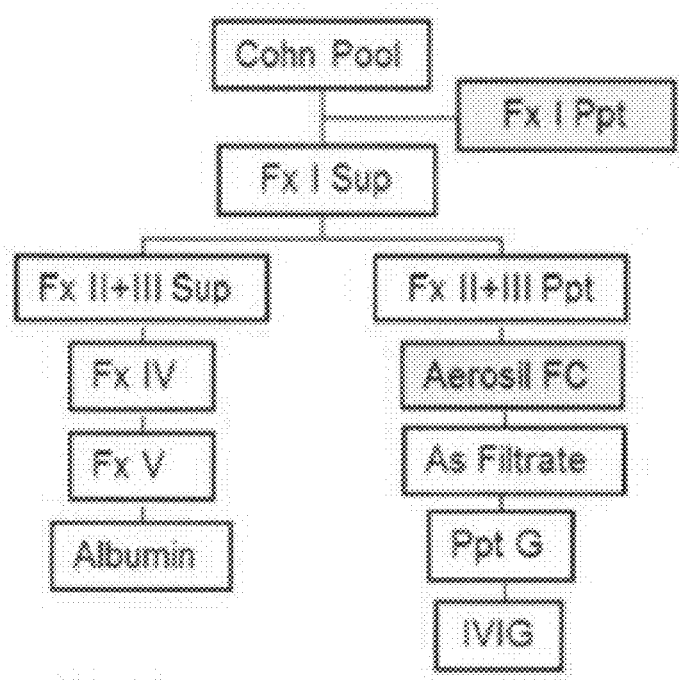

Example 4—Characterization of Factor H Proteolysis in Fractions Generated During Alcohol Fractionation of Human Plasma The proteolytic state of Factor H in various plasma fractions produced during the manufacture of pooled human immunoglobulin G compositions, such as GAMMAGARD® LIQUID (Baxter Healthcare Corporation, Westlake Village, Calif.), was investigated by western blot analysis. As seen in the western blot reproduced in FIG. 5A, the proteolysis of Factor H increases as Factor H progresses through the plasma fractionation process shown in FIG. 5B. For example, the percentage of clipped Factor H in the Fraction II+III precipitate is greater than in the Fraction I precipitate (e.g., as indicated by the ratio of the intensities of the 120 kDa and 155 kDa bands in lanes 8 and 6, respectively). These results suggest that Factor H compositions purified from Fraction I precipitates will have a better proteolytic profile (e.g., a smaller percentage of clipped Factor H) than Factor H compositions purified from Fraction II+III precipitates (e.g., from Cohn Fraction II+III silicon dioxide filter cake).

Example 5—Activity Profiles of Factor H Compositions Purified from Human Plasma

Functional effects of the observed proteolytic clipping of Factor H purified from Cohn Fraction II+III silicon dioxide filter cake were investigated by performing assays assessing various biological functions of Factor H. It was found that proteolytic clipping of Factor H did not have a significant effect on Factor I cofactor activity, but did significant reduce C3b binding, $AH_{50}$ heamolysis, and decay acceleration (DAF) activity in preparations isolated from Cohn Fraction II+III silicon dioxide filter cake.

Figure 6:
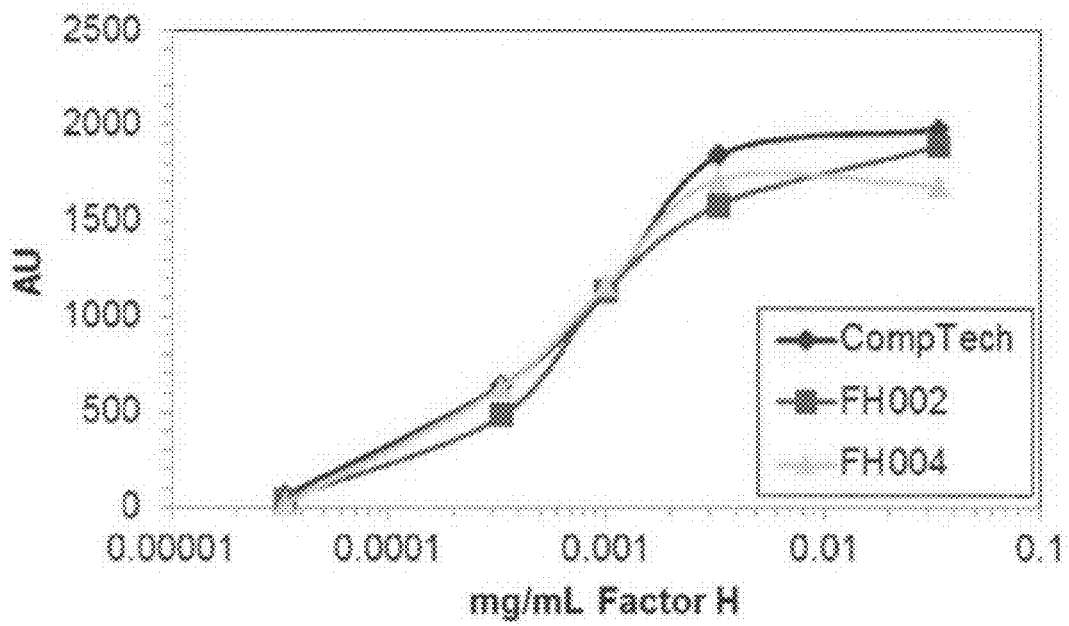
FIG. 6 illustrates the results of Factor I cofactor assays performed with recombinant Factor H (CompTech) and Factor H purified from Fraction II+III silicon dioxide filter cake (FH002 and FH004).

FIG. 6 shows the results of Factor I cofactor assays performed with Factor H isolated from Cohn Fraction II+III silicon dioxide filter cake (FH002 and FH004) and plasma-derived Factor H (CompTech, Tyler, Tex.). These results demonstrate that proteolytic clipping of Factor H does not affect Factor I cofactor activity (compare FH002 and FH004 to CompTech).

Figure 7:
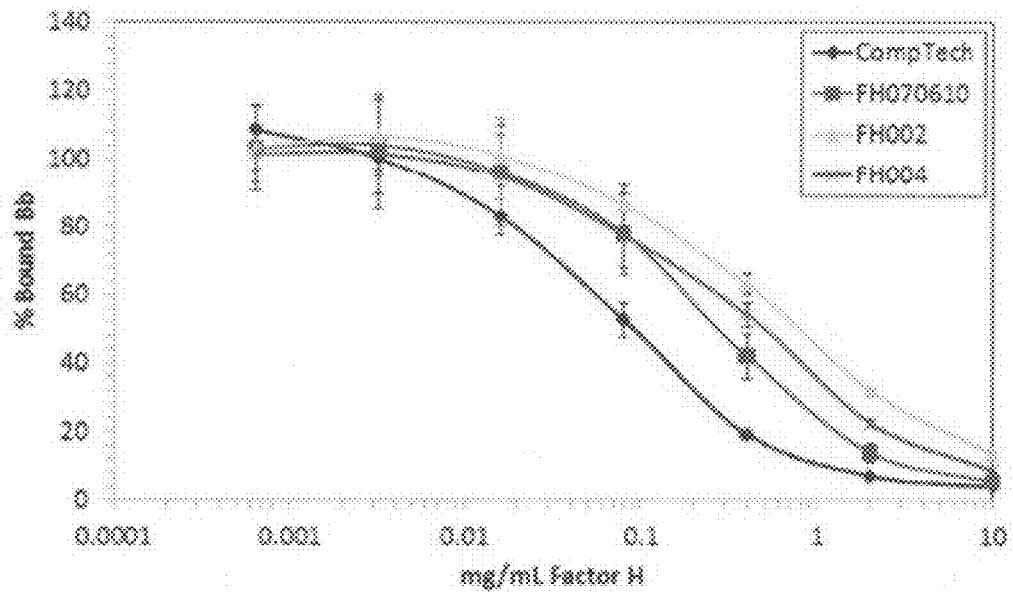
FIG. 7 illustrates the results of decay acceleration (DAF) assays performed with recombinant Factor H (CompTech) and Factor H purified from Fraction II+III silicon dioxide filter cake (FH002, FH004, and FH070610).

FIG. 7 shows the results of decay acceleration (DAF) ELISA assays performed with Factor H isolated from Cohn Fraction II+III silicon dioxide filter cake (FH002, FH004, and FH070610) and plasma-derived Factor H (CompTech, Tyler, Tex.).

Figure 8:
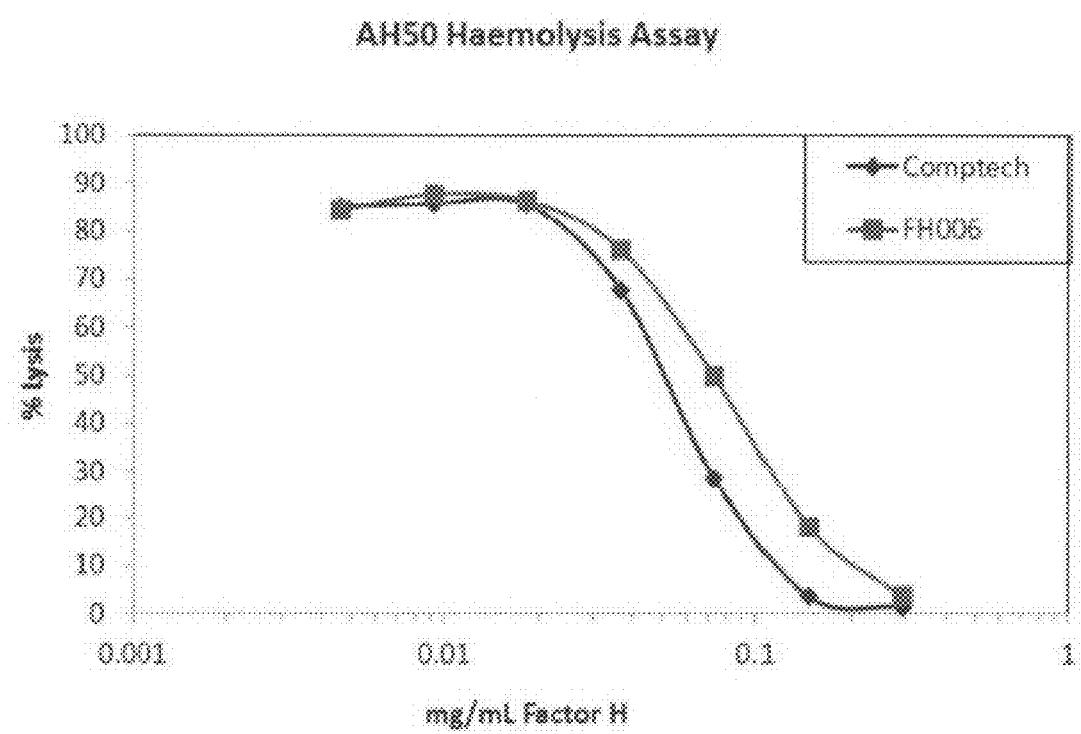
FIG. 8 illustrates the results of $AH_{50}$ haemolysis assays performed with recombinant Factor H (CompTech) and Factor H purified from Fraction II+III silicon dioxide filter cake (FH006).

FIG. 8 shows the results of AHSO heamolysis activity assays performed with Factor H isolated from Cohn Fraction II+III silicon dioxide filter cake (FH006) and plasma-derived Factor H (CompTech, Tyler, Tex.). These results demonstrate that the proteolytic clipping in Factor H observed in compositions prepared from reduces Cohn Fraction II+III silicon dioxide filter cake reduces the compositions ability to promote haemolysis.

Taken together, these results suggest that proteolytically clipped Factor H has a reduced binding affinity for surface bound C3b. Without being bound by theory, the reduced binding affinity is likely due to a disruption in the C3b binding site found in short consensus repeat (SCR) domains 6-8 adjacent to the proteolytically clipped site in SCR domain 5. The finding that Factor I cofactor activity is not disrupted in Factor H preparations from Cohn Fraction II+III silicon dioxide filter cake is consistent with clipping in SCR domain 5, because SCR domains 1-4, critical for Factor I cofactor activity, remain intact.

Figure 9:
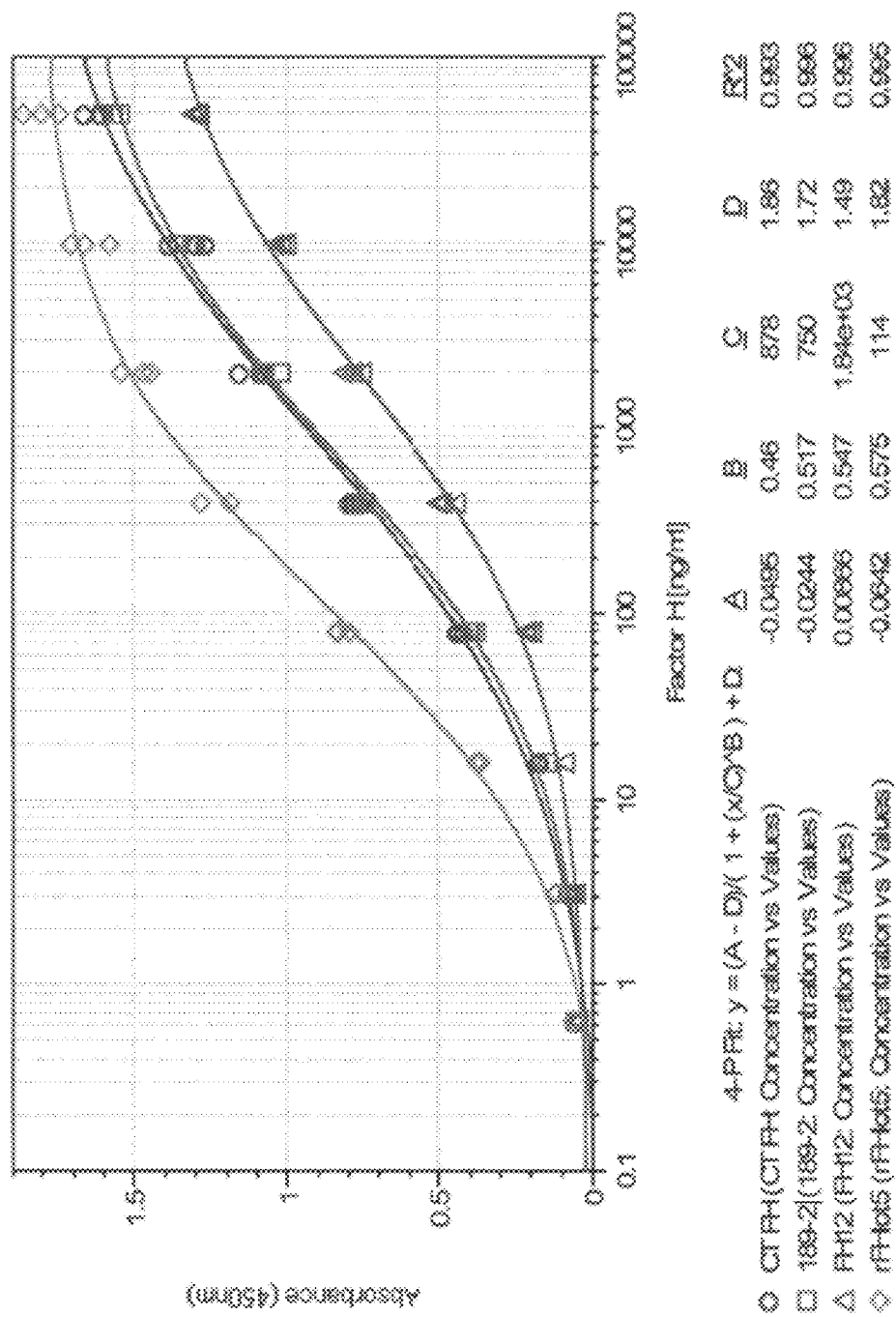
FIG. 9 illustrates the results of C3b ELISA assays performed with commercially available recombinant Factor H (CompTech), Baxter in-house recombinant Factor H (rF-Hlot5), Factor H purified from Fraction II+III silicon dioxide filter cake (FH12), and Factor H purified from Fraction I precipitate (189-2).

Example 6—Biochemical Analysis of Factor H Purified from Fraction I Precipitate and Comparison to Factor H Purified from Fraction II+III Silicon Dioxide Filter Cake As discussed in Example 3, Factor H compositions prepared from Fraction II+III silicon dioxide filter cake contain proteases that proteolytically clip Factor H at SCR domain 5. As described above, proteolytically clipped Factor H has reduced binding to C3b in ELISA assays. The C3b binding activity of Factor H purified from Fraction II+III silicon dioxide filter cake according to old methods (FH12) was compared to C3b binding activities of Factor H purified from Fraction I precipitate (189-2), commercially available plasma-derived Factor H (CT FH; CompTech, Tyler, Tex.), and recombinant Factor H prepared in-house at Baxter (rFHlot5). The results of this comparison, shown in FIG. 9, demonstrate that Factor H purified from Fraction II+III silicon dioxide filter cake has significantly lower binding affinity to immobilized (e.g., surface bound) C3b than does both Factor H prepared from Fraction I precipitate commercially available plasma-derived Factor H. Without being bound by theory, it is likely that the loss of C3b binding activity can be attributed to the extensive proteolytic clipping of Factor H purified from Fraction II+III silicon dioxide filter cake containing high amidolytic activity.

Example 7—Extraction of Factor H from Fraction II+III Silicon Dioxide Filter Cake As shown in Example 4, Fraction II+III silicon dioxide filter cake fractions contain high levels of proteolytic activity, causing the proteolytic clipping of Factor H. This disruption in the structure of Factor H is believed to be responsible for reduced biochemical activities of Factor H compositions purified from Fraction II+III silicon dioxide filter cake, as compared to Factor H purified from Fraction I precipitate and plasma-derived Factor H (see, FIGS. 7-9). To reduce proteolytic clipping of Factor H, the conditions used to extract Factor H from Fraction II+III silicon dioxide filter cake were investigated to identify conditions that reduce co-extraction of proteolytic activity.

Briefly, experiments varying the pH and ionic strength of 20 mM and 50 mM sodium citrate extraction buffer systems were performed. Two series of twelve extraction buffers containing 20 mM sodium citrate or 50 mM citrate were formulated, each with a different combination of 0 mM, 75 mM, and 150 mM sodium chloride at pH 5.0, 5.5, 6.0, and 6.5. Each buffer was then used for the extraction of Factor H from 12 grams of a Fraction II+III silicon dioxide filter cake. The Factor H content of each resulting extract was determined by ELISA and the proteolytic profile of each extract was evaluated by protease activity assays using CS-2166 (activated protein C and FXIa) and CS-3102 (Kallikrein and Factor FXIIa) protease substrates.

Figures 10A, 10B, 10C:
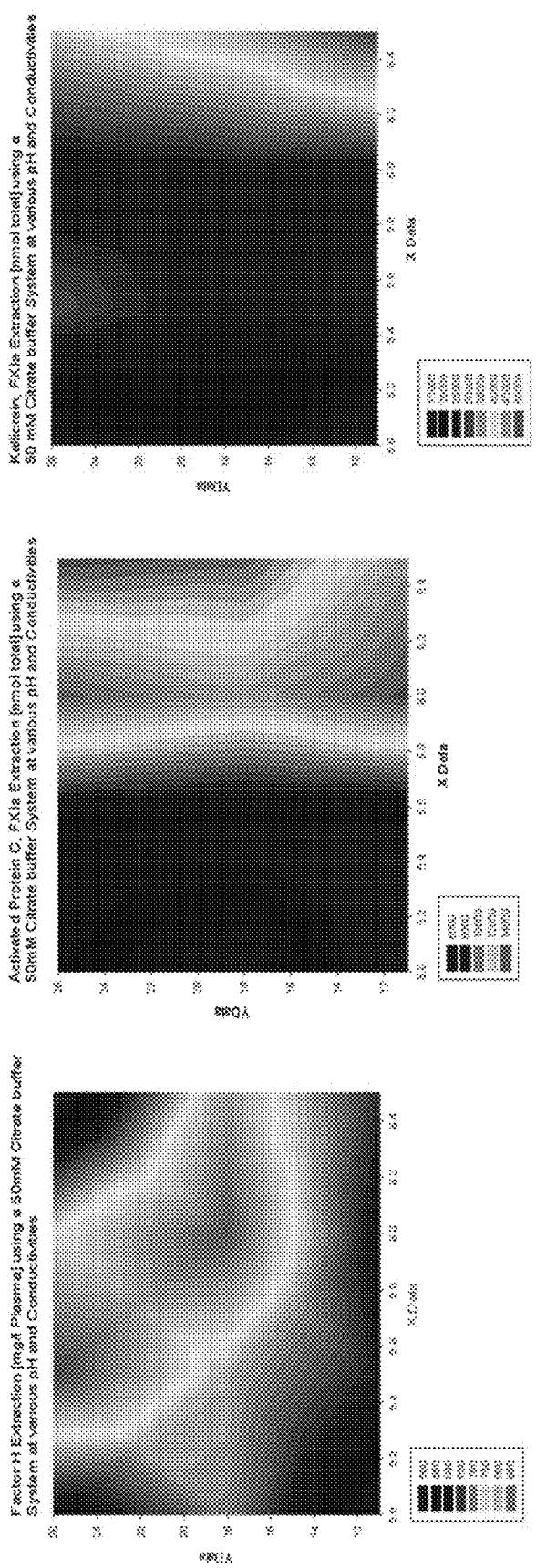
FIG. 10A-10C illustrate contour plats generated from experiments evaluating the extraction of Fraction II+III silicon dioxide filter cake using 50 mM sodium citrate buffer systems formulated with 0 mM, 75 mM, and 150 mM sodium chloride at pH 5.0, 5.5, 6.0, and 6.5.

The result of the experiment was that the 50 mM citrate buffer system provided better extraction of Factor H and separation from amidolytic activities. The contour plot generated for Factor H (FIG. 10A) and amidolytic activity (FIGS. 10B and 10C) show that the patterns of Factor H and amidolytic activity extraction have different dependencies on the pH and ionic strength of the extraction buffer system. For example, Factor H extraction depends relatively equally upon conductivity and ionic strength, with maximal extraction conditions running diagonally from relative high ionic strength, relative low pH (FIG. 10A, upper left quadrant) to relative low ionic strength, relative high pH (FIG. 10A, lower right quadrant). Three local maximums for Factor H extraction were identified, centered around about (18 mS/cm, pH 6.0), (25 mS/cm, pH 5.5), and (19 mS/cm, pH 5.2), respectively.

In contrast, the extraction of CS-2166 (activated protein C and FXIa; FIG. 10B) and CS-3102 (Kallikrein and Factor FXIIa; FIG. 10C) amidolytic activities were more dependent upon pH than ionic strength. For example, extraction of CS-2166 activity increased upwards from a pH of about 5.5 and downwards from a pH of about 6.6-7.0 (extrapolated), with local maximums at all tested ionic strengths around pH 6.0. Likewise, extraction of CS-3102 activity increased upwards from a pH of about 6.0, reaching local maximum tested levels at pH 6.0 for all tested ionic strengths. Generally, using the citrate buffer, extraction at a pH below 5.7 reduces extraction of amidolytic activities. At these pH values, higher conductivities may be employed to improve extraction of Factor H.

Thus, because the Factor H local maximum centered around about 18 mS/cm, pH 6.0 overlaps with maximum CS-2166 amidolytic activity extraction, conditions surrounding the other Factor H extraction maximums (25 mS/cm, pH 5.5) and (19 mS/cm, pH 5.2) were selected as candidate conditions for the large scale extraction of Factor H from Fraction II+III silicon dioxide filter cake produced during industrial plasma fractionation.

Example 8—Scale-Up of Factor H Extraction from Fraction II+III Aerosil Filter Cake To investigate whether the differential extraction of Factor H and amidolytic activity is preserved in large-scale, extraction was repeated with three-1 kg lots of Fraction II+III aerosil filter cake. Briefly, each filter cake was extracted with five volumes of extraction buffer containing 50 mM sodium citrate and 75 mM sodium chloride at pH 5.0. As shown in Table 3, Factor H extraction was slightly reduced in the scaled-up extractions, while amidolytic activities were increased. The increase in extraction of the amidolytic activity may be due to increased sheer force applied by use of a larger metal stirrer, as compared to the magnetic stirrer used for the smaller scale experiment. Regardless, the level of amidolytic impurities still appear to be within ranges suitable for further enrichment of Factor H.

TABLE 3

Comparison and variance of small scale (12 g filter cake) and large scale
(1 kg filter cake) extraction of Factor H and amidolytic activities from
Fraction II + III aerosil filter cake.

| Lot | Factor H [mg/L plasma] | Hydrolysis rate | |
| --- | --- | --- | --- |
| | | CS-2166 [nmol * min total] | CS-3102 [nmol * min total] |
| Small Scale | 700 | 8000 | 20000 |
| Larger Scale Lot A | 460 | 10629 | 30837 |
| Larger Scale Lot B | 565 | 12145 | 34523 |
| Larger Scale Lot C | 488 | 10519 | 29099 |
| Average of Lot A, B, C | 504 | 11098 | 31486 |
| Variance from small-scale (%) | +/−28 | −+/−39 | −+/−57 |

Example 9—Effect of Detergent on the Extraction of Factor H and Amidolytic Activities from Fraction II+III Filter Cake Detergents are known to increase protein extraction from precipitates and to generally stabilize proteins. To determine whether inclusion of a non-ionic detergent in the extraction buffer would improve Factor H extraction, 0.2% polysorbate 80 was added to extraction buffer containing 50 mM sodium citrate and 75 mM sodium chloride at pH 5.0. The buffer was then used to extract seven samples of Fraction II+III filter cake. As shown in Table 4, addition of polysorbate 80 increased Factor H extraction by an average of 15% across the seven samples. However, inclusion of polysorbate 80 also increased extraction of CS-2166 and CS-3102 amidolytic activities by more than 70% and 65%, respectively. Accordingly, non-ionic detergent should not be added to the extraction buffer where the amidolytic activities are a major concern to the preparation.

TABLE 4

Increase in extraction of Factor H and amidolytic activity from
Fraction II + III filter cake by the addition of
polysorbate 80 to the extraction buffer.

| | Factor H yield Increase | Increase of hydrolysis rates | |
| --- | --- | --- | --- |
| | | CS-2166 % | CS-3102 |
| Ultra-Dia/Filtrate: Average of 7 Lots compared to 3 Lots without 0.2% Polysorbate 80 | 15.78 | 72.87 | 67.18 |

Example 10—Comparison of Citrate and Phosphate Buffered Extraction Systems for Extraction of Factor H from Fraction II+III Aerosil Filter Cake To determine the effect a phosphate buffered system on Factor H extraction from a Fraction II+III aerosil filter cake, five-1 kg extractions were performed using buffer containing 100 mM phosphate buffer at pH 6.0 and compared to four-1 kg extrations using the citrate buffer described above. As shown in Table 5, extraction with the citrate-buffered system described above resulted in 45% greater extraction of Factor H, with slightly increased purity (35.3% vs. 33.9%), and reduced extraction of amidolytic activity, as compared to extraction using the phosphate-buffered system.

TABLE 5

Comparison of Factor H and amidolytic activity extraction from
Fraction II + III filter cake using citrate and
phosphate-based extraction buffer systems.

| | Factor H | | Hydrolysis rates | |
| --- | --- | --- | --- | --- |
| | [mg/L Plasma] | % total protein | CS-2166 [nmol * min total] | CS-3102 [nmol * min total] |
| 1 kg filter cake extraction (100 mM Phosphate buffer pH 6.0) and filtration; Average of 5 lots | 387 | 33.87 | 542336 | 1420314 |
| 1 kg filter cake extraction (50 mM Na-Citrate, 75 mM NaCl pH 5.0) and filtration; Average of 4 lots | 561 | 35.30 | 399609 | 1259959 |

Example 11—Reduction of Amidolytic Activity by Heat Inactivation

It was investigated whether the high heat stability of Factor H (reported in Kask et al., 2004) would allow inactivation of amidolytic impurities in the preparation at high temperatures without jeopardizing Factor H activity. Pasteurization is known to reduce amidolytic activities within the production of several plasmatic protein products like Albumin, FLEBOGAMMA®, and FLEBOGAMMA® DIF produced by Grifols, SA (Jose et al., 2010). The goal here is to identify a treatment that maintains the Factor H activity of the composition, but provides a significant reduction in protease activity. To determine whether dissovled Fraction II+III filtercake could be heat treated prior to filtration, the following experiments were performed.

Several conditions with varying pH, sugar addition, temperature, and incubation time were evaluated. Briefly, the samples are dissolved for 2 h at 2-8° C., pH is adjusted to pH 6.5, 5% glucose is added each, and heat incubation is performed for 2 hours at 70° C. After this time the samples are filtered through Ahlstrom filters (Grade 988) and measured for amidolytic impurities as well as Factor H content via ELISA. Table 6 provides a summary of the additives added to each sample. As shown in Table 7, both Factor H and amidolytic impurities are reduced by the heat treatment. The additives used in the experiment did not stabilize Factor H during the treatment.

TABLE 6

Additives for Factor H heat treatment experiments.

| Sample | Additives |
| --- | --- |
| 1 | Albumin (20%) is added 1 + 1 to the dissolved solution |
| 2 | Albumin (20%) is added 1 + 9 to the dissolved solution |
| 3 | Albumin (20%) is added 1 + 99 to the dissolved solution |
| 4 | Dissolved Aprotinin (Aprotinin#VNL3J002) is added 1 + 1 to the dissolved solution |
| 5 | Dissolved Aprotinin (Aprotinin#VNL3J002) is added 1 + 9 to the dissolved solution |

TABLE 6-continued

Additives for Factor H heat treatment experiments.

| Sample | Additives |
|---|---|
| 6 | Dissolved Aprotinin (Aprotinin#VNL3J002) is added 1 + 99 to the dissolved solution |
| 7 | Antithrombin III is added 1 + 9 to the dissolved solution |
| 8 | Antithrombin III + Heparin (Heparin#VNB4J005) are added 1 + 1 + 8 to the dissolved solution |
| 9 | Heparin (Heparin#VNB4J005) are added 1 + 9 to the dissolved solution |
| 10 | Blank (dissolved filter cake) |

TABLE 7

Heat treatment prior to the filer cake filtration under the addition of defined additives like albumin, ATIII and Heparin.

| Sample | Factor H (g/L plasma) | Substrates CS-2166 [nmol/ml * min] | CS-3102 [nmol/ml * min] |
|---|---|---|---|
| Additive: Albumin (1 + 1) | | | |
| Filter cake dissolved | 0.41 | 725.86 | 1132.48 |
| Filter cake dissolved after 2 h 70° C. | 0.13 | 105.28 | 147.92 |
| Filter cake filtered | 0.05 | 10.41 | 8.99 |
| Additive: Albumin (1 + 9) | | | |
| Filter cake dissolved | 0.44 | 876.33 | 1423.33 |
| Filter cake dissolved after 2 h 70° C. | 0.06 | 152.52 | 183.26 |
| Filter cake filtered | 0.02 | <5.00 | 6.15 |
| Additive: Albumin (1 + 99) | | | |
| Filter cake dissolved | 0.53 | 779.80 | 1339.11 |
| Filter cake dissolved after 2 h 70° C. | 0.14 | 86.89 | 162.72 |
| Filter cake filtered | 0.08 | 8.87 | 7.93 |
| Additive: Aprotinin (1 + 1) | | | |
| Filter cake dissolved | 0.38 | 459.22 | 985.80 |
| Filter cake dissolved after 2 h 70° C. | 0.05 | 134.38 | 193.29 |
| Filter cake filtered | 0.02 | <5.00 | <5.00 |
| Additive: Aprotinin (1 + 9) | | | |
| Filter cake dissolved | 0.42 | 622.59 | 1096.52 |
| Filter cake dissolved after 2 h 70° C. | 0.11 | 105.28 | 236.04 |
| Filter cake filtered | 0.05 | <5.00 | <5.00 |
| Additive: Aprotinin (1 + 99) | | | |
| Filter cake dissolved | 0.51 | 838.07 | 1419.55 |
| Filter cake dissolved 2 h 70° C. | 0.16 | 136.12 | 286.42 |
| Filter cake filtered | 0.06 | <5.00 | 6.51 |
| Additive: ATIII (1 + 9) | | | |
| Filter cake dissolved | 0.58 | 577.52 | 1064.34 |
| Filter cake dissolved 2 h 70° C. | 0.02 | 63.60 | 56.31 |
| Filter cake filtered | 0.03 | <5.00 | <5.00 |
| Additive: ATIII + Heparin (1 + 1 + 8) | | | |
| Filter cake dissolved | 0.58 | 561.08 | 928.38 |
| Filter cake dissolved 2 h 70° C. | 0.07 | 148.87 | 127.11 |
| Filter cake filtered | 0.04 | <5.00 | <5.00 |
| Additive: Heparin (1 + 9) | | | |
| Filter cake dissolved | 0.64 | 770.66 | 1361.82 |
| Filter cake dissolved 2 h 70° C. | 0.07 | 157.00 | 134.94 |
| Filter cake filtered | 0.04 | <5.00 | <5.00 |
| No additive: Blank | | | |
| Filter cake dissolved | 0.50 | 781.38 | 1274.44 |
| Filter cake dissolved 2 h 70° C. | 0.07 | 97.14 | 61.04 |
| Filter cake filtered | 0.05 | <5.00 | <5.00 |

Example 12—Stabilization of Factor H During Heat Treatment

The addition of sugar is known to increase protein stability (Arakawa & Timasheff, 1982). In an effort to further reduce the level of proteolytic activity in Factor H compositions extracted from Fraction II+III silicon dioxide filter cake, heat treatment of these compositions was investigated. Studies were undertaken to identify solution conditions that stabilized Factor H during incubation at high temperature (70° C.) for extended periods of time (1-4 hours).

Figure 11:
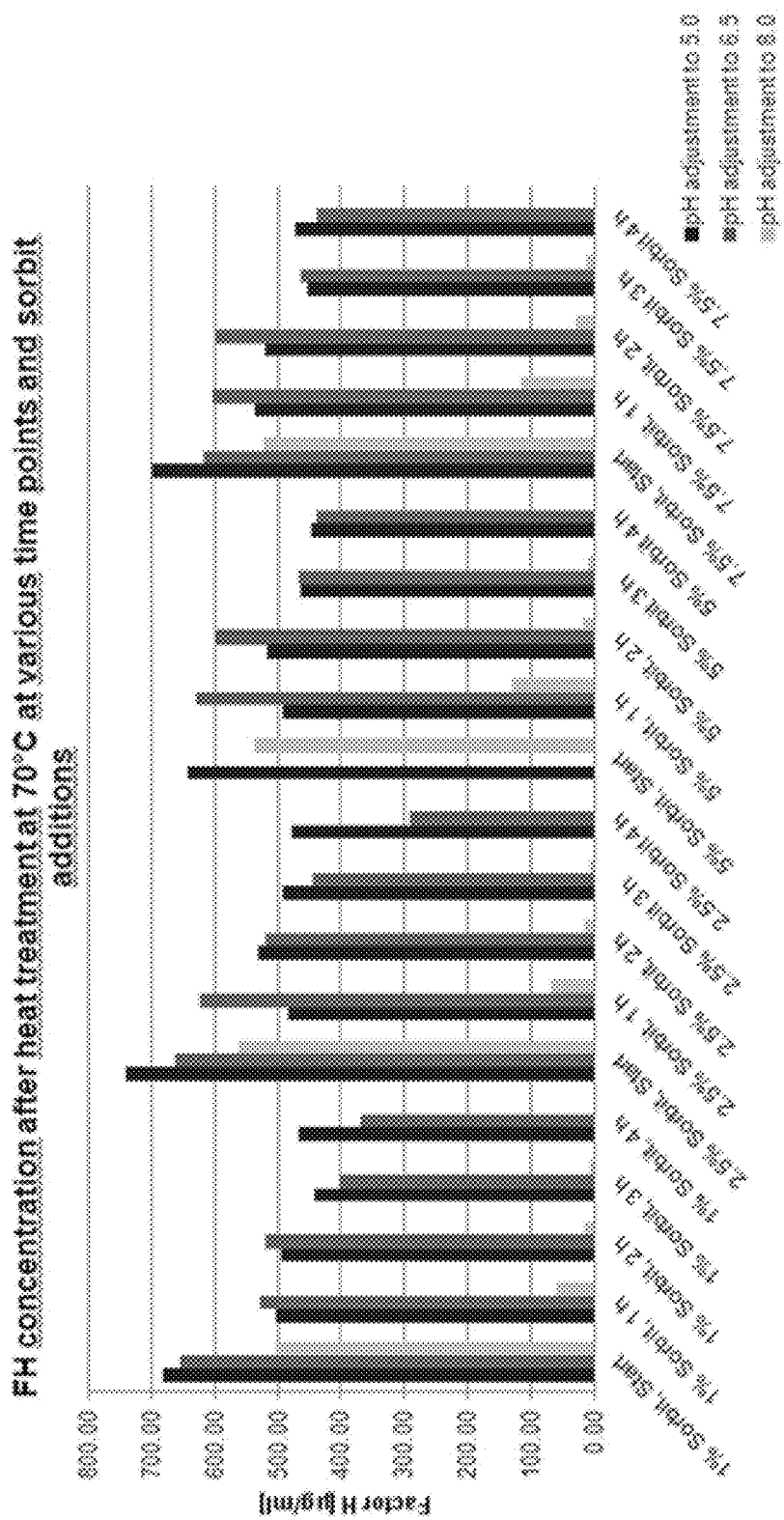
FIG. 11 illustrates Factor H concentrations (µg/mL) of Factor H samples prepared according to Example 16 after heat treatment performed at 70° C. for 1, 2, 3, or 4 hours in the presence of 1%, 2.5%, 5%, or 7.5% sorbitol ("sorbit").

Briefly, aliquots of a Factor H composition extracted from Fraction II+III silicon dioxide filter cake was formulated with increasing concentrations from 1% to 7.5% of the stabilizing agent sorbitol ("sorbit") at pH 5.0, 6.5, and 8.0. The various formulations were then incubated for 1, 2, 3, and 4 hours at 70° C. The results, illustrated in FIG. 11, show that Factor H is equally stabilized with 5% and 7.5% sorbitol in the pH 6.5 and 5.0 formulations. Maximum Factor H stability was identified upon a 2 hour heat treatment using 5% sorbitol at pH 6.5. This condition was used as a starting point for further experimentation. Notably, at all concentrations of sorbitol, Factor H formulated at pH 8.0 was almost completely denatured after 1 hour of incubation at 70° C. Taken together, these results suggest that formulation at mildly acidic to acid conditions with moderate levels of a sugar and/or sugar alcohol stabilize Factor H at high temperatures for extended periods.

Example 13—Stabilization of Factor H and Reduction of Amidolytic Activity During Heat Treatment The effect of heat treatment on Factor H content and amidolytic activity was determined across a range of pH values and temperatures. Briefly, Factor H was extracted from a Fraction II+III aerosil filter cake at pH 6.0 in a 100 mM phosphate buffer and clarified by filtration using a Cuno 50 SA filter. The clarified extracted was separated into samples, to which sorbitol was added to a final concentration of 1%, 2.5%, 5%, or 7.5%, and the pH adjusted to 5.0, 6.5, or 8.0. The samples were then heated for four hours at 60° C. (Table 8), 65° C. (Table 9), or 70° C. (Table 10). Each sample was tested hourly during the incubation for Factor H stability, S-2302 (Kallikrein and Factor FXIIa) proteolytic activity, and CS-2166 (activated protein C and FXIa) proteolytic activity. As shown in Table 8-Table 10, incubation at pH 5.0 resulted in significant losses of Factor H content, while incubation at pH 8.0 resulted in inadequate reduction in amidolytic activity. Incubation at pH 6.5 provided satisfactory reduction of amidolytic activity without large losses of Factor H content.

TABLE 8

Heat treatment of Factor H at 60° C. for various times, pH values, and sorbitol concentrations.

| Sorbit Addition (%) | Incubation (h) Condition | S-2302 [nmol/mL * min] | CS-2166 [nmol/mL * min] | Factor H [µg/mL] | S-2302 [nmol/mL * min] | CS-2166 [nmol/mL * min] | Factor H [µg/mL] | S-2302 [nmol/mL * min] | CS-2166 [nmol/mL * min] | Factor H [µg/mL] |
|---|---|---|---|---|---|---|---|---|---|---|
| | | pH adjustment to 5.0 | | | pH adjustment to 6.5 | | | pH adjustment to 8.0 | | |
| 1.0% | Start | 1166.55 | 559.42 | 681.52 | 1138.16 | 652.52 | 653.49 | 1073.49 | 768.76 | 504.51 |
| | 1 | 74.53 | 37.03 | 380.80 | 263.94 | 122.27 | 500.12 | 167.21 | 235.59 | 595.86 |
| | 2 | 78.78 | 33.75 | 343.65 | 182.71 | 89.43 | 477.19 | 123.31 | 150.59 | 601.68 |
| | 3 | 37.07 | 28.00 | 338.17 | 171.29 | 76.18 | 544.89 | 174.08 | 81.48 | 508.33 |
| | 4 | 37.62 | 29.02 | 386.97 | 184.78 | 82.07 | 536.00 | 197.13 | 87.61 | 459.65 |
| 2.5% | Start | 1119.55 | 492.46 | 739.42 | 1190.53 | 684.22 | 663.39 | 1048.57 | 742.90 | 561.62 |
| | 1 | 77.96 | 38.76 | 389.88 | 234.32 | 111.67 | 437.11 | 205.69 | 286.12 | 567.14 |
| | 2 | 55.56 | 32.33 | 381.85 | 189.92 | 90.82 | 548.30 | 157.87 | 221.57 | 659.95 |
| | 3 | 36.75 | 27.44 | 372.91 | 180.05 | 79.02 | 497.92 | 181.29 | 81.95 | 521.23 |
| | 4 | 34.03 | 26.32 | 376.07 | 177.32 | 79.05 | 572.40 | 191.97 | 84.61 | 448.42 |
| 5.0% | Start | 1134.06 | 551.26 | 641.30 | n.a. | n.a. | n.a. | 954.88 | 675.07 | 536.33 |
| | 1 | 87.12 | 43.30 | 400.74 | 321.57 | 152.36 | 427.99 | 251.64 | 309.71 | 658.08 |
| | 2 | 58.20 | 35.37 | 377.37 | 226.36 | 99.49 | 470.88 | 144.42 | 212.99 | 616.43 |
| | 3 | 40.69 | 31.27 | 399.66 | 207.58 | 85.65 | 547.45 | 230.63 | 97.81 | 581.56 |
| | 4 | 35.02 | 26.46 | 371.68 | 188.86 | 52.54 | 549.28 | 184.25 | 81.98 | 490.64 |
| 7.5% | Start | 1105.98 | 563.68 | 697.61 | 1128.07 | 1081.38 | 618.17 | 1016.08 | 730.91 | 521.59 |
| | 1 | 99.04 | 47.44 | 483.90 | 289.35 | 132.77 | 395.55 | 261.29 | 363.09 | 595.44 |
| | 2 | 53.86 | 35.61 | 374.47 | 292.62 | 121.30 | 411.96 | 170.88 | 238.67 | 607.79 |
| | 3 | 37.70 | 27.86 | 405.27 | 232.95 | 89.88 | 495.31 | 214.26 | 93.60 | 583.14 |
| | 4 | 35.57 | 20.50 | 383.45 | 47.40 | 33.95 | 529.56 | 210.00 | 89.23 | 626.50 |

TABLE 9

Heat treatment of Factor H at 65° C. for various times, pH values, and sorbitol concentrations.

| Sorbit Addition (%) | Incubation (h) Condition | S-2302 [nmol/mL * min] | CS-2166 [nmol/mL * min] | Factor H [µg/mL] | S-2302 [nmol/mL * min] | CS-2166 [nmol/mL * min] | Factor H [µg/mL] | S-2302 [nmol/mL * min] | CS-2166 [nmol/mL * min] | Factor H [µg/mL] |
|---|---|---|---|---|---|---|---|---|---|---|
| | | pH adjustment to 5.0 | | | pH adjustment to 6.5 | | | pH adjustment to 8.0 | | |
| 1.0% | Start | 1166.55 | 559.42 | 681.52 | 1138.16 | 652.52 | 653.49 | 1073.49 | 768.76 | 504.51 |
| | 1 | 61.04 | n.a. | 464.87 | 68.26 | 54.95 | 670.29 | 27.36 | 20.50 | 279.89 |
| | 2 | 52.29 | 31.70 | 423.35 | 68.20 | 50.60 | 648.91 | 12.66 | 11.47 | 91.10 |
| | 3 | 41.46 | 26.81 | 478.09 | 79.38 | 41.21 | 587.84 | 13.37 | <5 | 57.91 |
| | 4 | 52.32 | 30.56 | 440.40 | 49.72 | 35.02 | 597.50 | n.a. | n.a. | 37.22 |
| 2.5% | Start | 1119.55 | 492.46 | 739.42 | 1190.53 | 684.22 | 663.39 | 1048.57 | 742.90 | 561.62 |
| | 1 | 54.77 | 33.83 | 478.73 | 78.16 | 61.63 | 634.66 | 27.39 | 26.50 | 333.69 |
| | 2 | 42.35 | 28.00 | 427.20 | 83.93 | 59.89 | 651.64 | 13.49 | 11.60 | 112.63 |
| | 3 | 41.40 | 28.86 | 442.87 | 109.71 | 56.63 | 640.51 | 15.38 | 21.35 | 63.49 |
| | 4 | 41.76 | 24.13 | 476.10 | 63.08 | 41.17 | 594.02 | n.a. | n.a. | 40.67 |
| 5.0% | Start | 1134.06 | 551.26 | 641.30 | n.a. | n.a. | n.a. | 954.88 | 675.07 | 536.33 |
| | 1 | 50.28 | 34.07 | 483.78 | 92.12 | 65.69 | 591.81 | 54.02 | 32.18 | 371.11 |
| | 2 | 40.89 | 25.83 | 432.42 | 98.13 | 71.95 | 664.26 | 19.16 | 14.73 | 132.59 |
| | 3 | 49.37 | 27.44 | 431.66 | 117.04 | 60.33 | 627.72 | 16.92 | 11.42 | 101.91 |
| | 4 | 37.32 | 23.42 | 433.99 | 195.64 | 131.36 | 654.14 | n.a. | n.a. | 47.47 |
| 7.5% | Start | 1105.98 | 563.68 | 697.61 | 1128.07 | 1081.38 | 618.17 | 1016.08 | 730.91 | 521.59 |
| | 1 | 52.61 | 31.90 | 495.72 | 99.01 | 74.57 | 594.00 | 78.70 | 50.33 | 332.40 |
| | 2 | n.a. | 25.12 | 429.65 | 8.75 | 8.04 | 626.62 | 93.71 | 48.09 | 172.05 |
| | 3 | 40.69 | 20.89 | 458.66 | 9.11 | <5 | 589.40 | 49.62 | 36.71 | 120.41 |
| | 4 | 59.62 | 53.82 | 434.60 | 191.47 | 238.63 | 607.91 | n.a. | n.a. | 62.81 |

TABLE 10

Heat treatment of Factor H at 70° C. for various times, pH values, and sorbitol concentrations.

| Sorbit Addition (%) | Incubation (h) Condition | S-2302 [nmol/mL * min] | CS-2166 [nmol/mL * min] | Factor H [µg/mL] | S-2302 [nmol/mL * min] | CS-2166 [nmol/mL * min] | Factor H [µg/mL] | S-2302 [nmol/mL * min] | CS-2166 [nmol/mL * min] | Factor H [µg/mL] |
|---|---|---|---|---|---|---|---|---|---|---|
| | | pH adjustment to 5.0 | | | pH adjustment to 6.5 | | | pH adjustment to 8.0 | | |
| 1.0% | Start | 1166.55 | 559.42 | 681.52 | 1138.16 | 652.52 | 653.49 | 1073.49 | 768.76 | 504.51 |
| | 1 | 51.02 | 33.60 | 501.91 | 34.70 | 17.98 | 527.93 | <5 | 84.07 | 60.99 |
| | 2 | 49.30 | 35.61 | 494.81 | 18.28 | 13.25 | 519.34 | <5 | 85.80 | 14.18 |
| | 3 | 39.27 | 25.67 | 441.29 | 16.56 | 10.23 | 402.34 | <5 | 13.49 | 6.39 |
| | 4 | 43.12 | 31.23 | 466.15 | 14.49 | 10.59 | 368.51 | n.a. | n.a. | n.a. |

TABLE 10-continued

Heat treatment of Factor H at 70° C. for various times, pH values, and sorbitol concentrations.

| Sorbit Addition (%) Condition | Incubation (h) | S-2302 [nmol/ mL * min] | CS-2166 [nmol/ mL * min] | Factor H [µg/mL] | S-2302 [nmol/ mL * min] | CS-2166 [nmol/mL * min] | Factor H [µg/mL] | S-2302 [nmol/ mL * min] | CS-2166 [nmol/mL * min] | Factor H [µg/mL] |
|---|---|---|---|---|---|---|---|---|---|---|
| | | pH adjustment to 5.0 | | | pH adjustment to 6.5 | | | pH adjustment to 8.0 | | |
| 2.5% | Start | 1119.55 | 492.46 | 739.42 | 1190.53 | 684.22 | 663.39 | 1048.57 | 742.90 | 561.62 |
| | 1 | 48.82 | 32.93 | 483.01 | 49.27 | 24.61 | 623.21 | <5 | <5 | 68.01 |
| | 2 | 48.11 | 35.88 | 530.14 | 19.22 | 13.72 | 519.93 | <5 | <5 | 14.26 |
| | 3 | 40.10 | 27.80 | 493.28 | 20.23 | 11.00 | 445.70 | <5 | 13.54 | 6.16 |
| | 4 | 35.80 | 29.83 | 479.04 | 15.26 | 11.71 | 290.13 | n.a. | n.a. | n.a. |
| 5.0% | Start | 1134.06 | 551.26 | 641.30 | n.a. | n.a. | n.a. | 954.88 | 675.07 | 536.33 |
| | 1 | 47.95 | 35.90 | 492.18 | 47.29 | 23.48 | 628.68 | 6.74 | <5 | 128.28 |
| | 2 | 38.64 | 26.70 | 516.79 | 22.18 | 14.96 | 597.69 | <5 | <5 | 16.97 |
| | 3 | 44.01 | 33.64 | 464.22 | 19.64 | 9.11 | 465.98 | <5 | 14.96 | 9.24 |
| | 4 | 43.06 | 25.03 | 448.50 | 17.39 | 8.87 | 438.04 | n.a. | n.a. | n.a. |
| 7.5% | Start | 1105.98 | 563.68 | 697.61 | 1128.07 | 1081.38 | 618.17 | 1016.08 | 730.91 | 521.59 |
| | 1 | 41.96 | 29.06 | 537.03 | 57.87 | 22.95 | 603.76 | 7.33 | 6.62 | 116.84 |
| | 2 | n.a. | 28.08 | 518.57 | 23.95 | 17.98 | 596.95 | <5 | <5 | 27.80 |
| | 3 | 39.59 | 25.59 | 453.84 | 15.44 | 8.52 | 464.98 | <5 | 16.32 | 11.01 |
| | 4 | n.a. | n.a. | 473.64 | 21.23 | 11.69 | 440.30 | n.a. | n.a. | n.a. |

Example 14—Effect of Sugar on Factor H Stability During Heat Treatment

To investigate the inactivation of proteolytic activities and effects of various stabilizing agents, as second set of experiments were performed. Briefly, aliquots of a Factor H composition extracted from Fraction II+III silicon dioxide filter cake was formulated with 5% sorbitol, 5% glucose, or 5% sucrose ("saccharose") at pH 6.5 and again incubated for 1-4 hours at 70° C. After the heat treatments, each sample was tested for Factor H stability, S-2302 (Kallikrein and Factor FXIIa) proteolytic activity, and CS-2166 (activated protein C and FXIa) proteolytic activity.

The results, illustrated in FIG. 12, show that under all conditions, S-2302 and CS-2166 amidolytic activities are almost completely eliminated (greater than 96% reduction in tested amidolytic activities) after incubation for two hours at 70° C. No additional benefit was found when increasing the incubation time to 4 hours. All three sugars/sugar alcohols stabilized Factor H for up to four hours at 70° C., although glucose provided the best stabilization (98% Factor H recovery). These results demonstrate that heat treatment is an effective strategy for significantly reducing amidolytic activities in sugar/sugar alcohol stabilized Factor H compositions.

Example 15—Reduction of Factor XI Activity by Heat Treatment

It was next investigated whether Factor XI activity is also reduced by heat treatment. Briefly, Fraction II+III Aeorosil filter cake was dissolved in buffer containing 50 mM sodium citrate, 75 mM sodium chloride, and 0.2% Tween at pH 5.0. The suspension was then filtered using an Ahlstrom 988 filter. Glucose was added to the filtrate at a final concentration of 5% and the filtrate was adjusted to pH 6.5. The sample was then incubated at 70° C. for two hours. After heat treatment, the sample was concentrated using ultra/diafiltration. As shown in Table 11, the heat treatment reduced Factor XI activity by greater than 99%.

TABLE 11

Reduction of Factor XI activity by heat treatment of Factor H composition at 70° C. for two hours.

| | Volume (g) | Factor XI Zymogen (ELISA) | | | Factor H Step recovery (%) |
|---|---|---|---|---|---|
| | | [U/ml] | [U total] | Removal [U total in (%)] | |
| Filter cake dissolved in 50 mM Na-Citrate, 75 mM NaCl + 0.2% Tween pH 5.0 | 6281.0 | 1.3 | 8165.3 | 100 | 100 |
| Ahlstrom 988 filtrate | 6185.8 | 1.2 | 7299.3 | 10.6 | 97.7 |
| Filtrate pH (6.5) adjusted and incubated for 2 h at 70° C. | 6631.3 | <0.01 | <66.3 | >99.2 | 89.9 |
| Ultra-Dia/filtrate of the incubated filtrate | 729.7 | <0.01 | <7.3 | >99.9 | 73.6 |

Example 16—Extraction of Factor H from Fraction II+III Aerosil Filter Cake and Reduction of Amidolytic Activities This example demonstrates the recovery of Factor H and reduction in amidolytic activites after extraction from Fraction II+III aerosil filter cake. Briefly, 1 kg of Fraction II+III aerosil filter cake was extracted using buffer containing 50 mM sodium citrate and 75 mM sodium chloride at pH 5.0. The extract was filtered through Ahlstrom 988 filter paper to remove solid particles and serine proteases bound thereto. The filtrate was then adjusted to pH 6.5 and dextrose (i.e., glucose) was added to a final concentration of 5%. The filtrate was then incubated at 70° C. for two hours to inactivate amidolytic activities. After cooling, the heat-treated sample was concentrated to 2% protein (20 g/L) by ultrafiltration and diafiltered against 6-8 volumes of buffer containing 15 mM sodium phosphate, 5 mM sodium acetate, and 20 mM sodium chloride (pH 6.4). The concentrate was filtered through a FLUORODYNE® II filter (Pall Corporation). Recovery of Factor H and reduction of amidolytic activity was determined at each step.

As shown in Table 12, each step in the process afforded greater than 80% recovery of Factor H, while the combination of Ahlstrom 988 filtration and heat treatment provided 98% and 99% reduction of CS-2166 and CS-3102 amidolytic activity, respectively. Overall, the process resulted in recovery of 0.3 g Factor H per L starting plasma at greater than a 60% process recovery.

Further purification of the S/D-treated Factor H composition was performed using anion exchange chromatography, heparin affinity chromatography, and hexylamine (HEA) mixed mode chromatography. Briefly, Factor H was bound to DEAE anion exchange resin pre-equilibrated with buffer containing 32 mM monobasic sodium phosphate (pH 6.4), 5 mM sodium acetate at a conductivity of 3-4 mS/cm at 18-26° C. The bound resin was washed with 30 column volumes of wash buffer containing 15 mM monobasic sodium phosphate (pH 6.4), 5 mM sodium acetate, and 30 mM sodium chloride to remove residual S/D reagents. Factor H was then eluted from the anion exchange column using a buffer containing 25 mM Tris (pH 8.0), 150 mM sodium chloride, and 5 mM EDTA.

Anion exchange eluate fractions containing Factor H were collected and the conductivity of the solution was reduced to a conductivity of 7-9 mS/cm using 25 mM Tris (pH 8.0), 5 mM EDTA. Factor H was then bound to heparin affinity resin using a buffer system including 25 mM Tris (pH 7.2)

TABLE 12

Step recovery of Factor H and reduction in CS-2166 and CS-3102 amidolytic activity.

| | Hydrolysis rates | | | Factor H | | |
| --- | --- | --- | --- | --- | --- | --- |
| | CS-2166 | | CS-3102 | | | |
| | [nmol * min total] | Reduction (%) | [nmol * min total] | Reduction (%) | [g/L plasma] | Recovery (%) | Step Recovery (%) |
| 1 kg filter cake dissolved in 50 mM Na-Citrate, 75 mM NaCl at pH 5.0 | 2320341 | — | 6493252 | — | 0.49 | 100 | 100 |
| Ahlstrom 988 filtrate | 879534 | 62 | 2551769 | 61 | 0.46 | 94 | 94 |
| Filtrate pH (6.5) adjusted | 905341 | 61 | 2781444 | 57 | 0.37 | 75 | 81 |
| 5% Dextrose addition + incubated for 2 h at 70° C. | <35528 | >98 | 61393 | 99 | 0.38 | 77 | 102 |
| 100 kDa Membrane Ultra-Dia/filtrate of the incubated filtrate | 42102 | 98 | 64213 | 99 | 0.32 | 66 | 86 |
| Flurodyne II filtrate | 37893 | 98 | 60782 | 99 | 0.30 | 61 | 93 |

Example 17—Improved Purification of Factor H from Fraction II+III Silicon Dioxide Filter Cake This example demonstrates the purification of a Factor H composition having reduced amidolytic activity and less than 20% proteolytic clipping from Fraction II+III silicon dioxide filter cake, generated as a side fraction of the manufacturing process for pooled human IgG products such as GAMMAGARD® LIQUID.

Factor H was extracted from 10 kg of Fraction II+III silicon dioxide filter cake (prepared according to standard methods as described above) by suspension in six volumes of buffer containing 50 mM sodium citrate (pH 5.0) and 75 mM sodium chloride to extract Factor H. The resulting Factor H extract was filtered, and the pH of the filtrate was adjusted to pH 6.5. Glucose was then added, as a stabilizing agent, to a final concentration of 5%. The stabilized Factor H extract was then incubated for two hours at 67-70° C. to inactivate amidolytic activity. After cooling, the composition was reformulated using Ultra-/Diafiltration against buffer containing 32 mM 32 mM monobasic sodium phosphate (pH 6.4) and subjected to S/D treatment under standard conditions (1% Triton X-100, 0.3% polysorbate 80, and 0.3% TNBP).

and 5 mM EDTA at a conductivity of 7.5-8.5 mS/cm. The bound heparin affinity resin was washed with 10 column volumes of buffer containing 25 mM Tris (pH 8.0), 5 mM EDTA, and 50 mM sodium chloride. Factor H was then eluted using buffer containing 25 mM Tris (pH 8.0), 5 mM EDTA, and 300 mM sodium chloride.

The heparin affinity eluate was loaded onto HEA Hyper-Cel mixed mode resin (Pall Corporation). The bound HEA mixed mode resin was washed with buffer containing 200 mM sodium acetate (pH 6.4) and 3.5 mM acetate. Factor H was eluted from the HEA mixed mode resin using buffer containing 90 mM sodium acetate (pH 4.4) and 130 mM acetate. The HEA mixed mode eluate was pre-filtered through a CUNO VR06 depth filter and then nanofiltered using a PLANOVA 20N (19±2 nm) filter. The nanofiltrate was then concentrated to 14 mg/mL by ultra-/diafiltration.

Example 18—Characterization of the Purity of Factor H Prepared from Fraction II+III Silicon Dioxide Filter Cake The purity of the Factor H composition prepared in Example 17 was investigated and compared to those of a Factor H composition prepared from Fraction II+III silicon dioxide filter cake as described in Example 1. These analyses show that the improved process steps provided herein for purifying Factor H from Fraction II+III silicon dioxide filter cake significantly reduce amidolytic activity and proteolytic clipping in the final Factor H composition. Furthermore, the methods provided herein result in a final enriched Factor H composition containing low lipopolysaccharide (LAL) content, and high overall purity. Taken together, these results demonstrate that the improved Factor H process steps, including Fraction II+III silicon dioxide filter cake extraction, heat treatment, and improved chromatographic enrichment, provide significant improvement over previously known methods for purifying Factor H from plasma.

Figure 13:
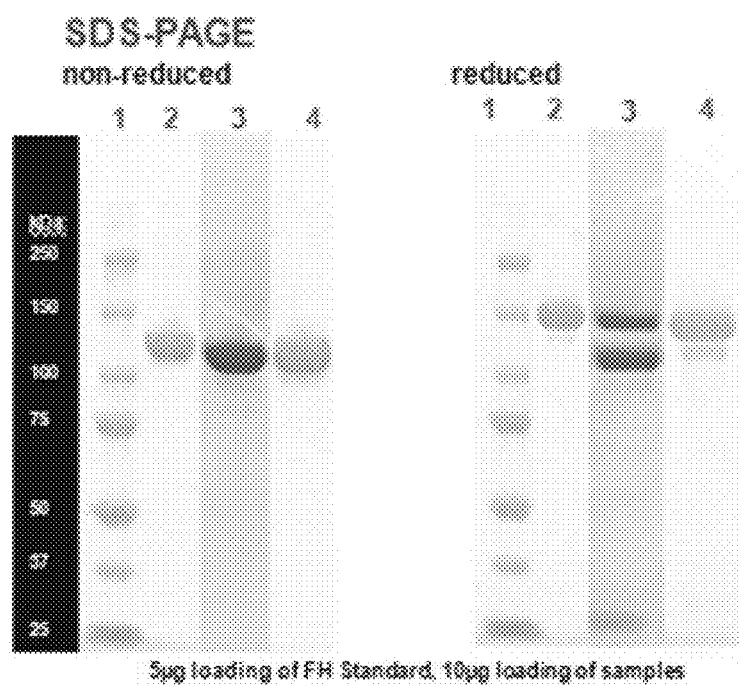
FIG. 13 shows an SDS-PAGE analysis of Factor H proteolytic clipping in composition prepared from Fraction II+III silicon dioxide filter cake according to the prior method described in Example 1 (FH012 FC; lane 3) and the improved method described in Example 16 (FH184 FC; lane 4). Recombinant Factor H (CompTech) is included in lane 2 for comparison.

First, the level of proteolytic clipping of the Factor H composition prepared in Example 17 is significantly lower than the level of proteolytic clipping in Factor H compositions prepared according to the method described in Example 1. FIG. 13 shows side by side SDS-PAGE analysis of the compositions, revealing that a Factor H composition prepared with the improved process steps is subject to less proteolytic clipping. Quantitation performed using ImageJ software shows that 81.5% of the Factor H prepared in Example 17 (FH184 FC) is intact, while Factor H prepared as in Example 1 (FH012 FC) is only 43% intact (compare reduced lanes 4 and 3, respectively).

Next, the amidolytic profile of a Factor H composition prepared according to Example 1 (FH012) was compared to the amidolytic profile of the Factor H composition prepared in Example 17 (FH184) using chromaogenic protease substrates for an array of amidolytic proteases found in human plasma. As shown in FIG. 14, purification according to the improved methods provided herein significantly reduces amidolytic activity having various specificities, most significantly Kallikrein, Factor XIa, and Factor XIIa activities, compare 248 nmol/mL*min for the old purification method to less than 5 nmol/mL*min for the improved purification.

It was also found that the improved chromatographic methods described herein result in a greater than 95% reduction in the level of lipopolysaccharides (LAL) present in the Factor H extract from Fraction II+III silicon dioxide filter cake. This is significant because Factor H has affinity for lipopolysaccharides (Tan et al., 2011), complicating their removal from plasma-derived Factor H compositions. The Factor H eluates of the heparin affinity chromatographic step and final product (which acts as a proxy for the HEA mixed mode chromatographic step, the final chromatographic enrichment step performed) formed in Example 17 were tested for FAF activity using an Endosafe®-PTS FAF cartridge reader (Charles River). As shown in FIG. 15, DEAE and Heparin affinity chromatographic steps reduced FAF activity by more than 70%, while the overall reduction from all chromatographic steps was greater than 95%.

Biochemical characterization data of the final Factor H composition purified as described in Example 17 shows very low levels of impurities (Table 13). The largest impurity tested was C3 (about 0.9% of total protein, 121 µg/mL). The TGA value is close to normal plasma and PKKA activity is within the specification limit provided in the European Pharmacopoeia, e.g., for. plasma-derived albumin. As described above, amidolytic impurities are below the detection limit. As a solvent detergent virus inactivation step is performed also Polysorbate 80, TNBP and Triton have to be determined. All values were below the detection limit showing an effective separation of factor H from S/D reagents using the chromatographic purification steps described above.

Several different chromogenic substrates with different specificities were used to assess amdiolytic impurities in the preparations. The specificity for each substrate is based on the amino acid sequence of the substrate. Upon cleavage, p-nitroaniline is released from the substrate and quantitated by photospectrometry (Snape et al, 1979). The substrates evaluated in this study include CS21(66), specific for activated protein C, FXIa, and CS31(02), specific for Kallikrein, Factor XIa and Factor XIIa, both distributed by Biophen. The substrate specific for Kallikrein only was purchased from Chromogenix-Instrumentation Laboratory SpA. The PL-1 substrate, manufactured by Pentapharm (Pefachrome® PL5272: H-D-Nle-CHA-Lys-pNA* 2HCl), is cleaved by Kallikrein, plasmin, and other plasmin-like proteases.

Non-activated partial thromboplastine-time (NAPTT) activity is determined using Factor XI deficient plasma. The assay is based on the recent revision of the European Pharmacopoeia (Ph. Eur.) entry for "Human prothrombin complex" and "Activated coagulation factors". All intravenous immunoglobulin solutions must be investigated with respect to procoagulant activity (Roemisch et al, 2012). As this is relevant for all plasmatic products the present method was applied in this study. The results are expressed as the amount of product in the test (100 µl of the sample is used in the test) which is able to shorten the Non-Activated Partial Thromboplastin Time (NAPTT) to 180 seconds, a value close to normal plasma control. If a sample having 50 mg/mL protein concentration does not shorten NAPTT the results is given as >5 mg (100 µg of a 50 mg/mL solution reflect 5 mg).

Thrombin generation assay (TGA) activity is determined via a method developed by Hemker 1986 (Hemker et al., 1986; Hemker, 2002). The test was further refined by Gatt and colleagues ((Gatt et al., 2008; van Veen et al., 2009)) appling a calibrated automated system.

PreKallikrein activator (PKA) activity is determined based on the European Pharmacopoeia (Ph. Eur.) monograph for determination of PKA (2.6.15; 2009). This assay uses a chromogenic substrate (Kallikrein Substrate PW-2302: H-D-Pro-Phe-Arg-pNA+H2O) manufactured by Pathway Diagnostics Ltd. The plasma PreKallikrein is activated to Kallikrein by the PKA activator (PKA-FXIIa). Kallikrein cleavage releases p-nitroaniline (pNA) from the Kallikrein substrate, which can be measured at 405 nm in a microtiter plate reader (Longstaff et al., 2005).

TABLE 13

Biochemical characterization of purified Factor H composition.

| Impurity | R&D Sample of a final container Protein value: 1.355, pH 6.8 | |
|---|---|---|
| | [µg/mL] | [% of protein total] |
| Immunoglobulins | | |
| IgM | 7.9 | 0.058 |
| IgA | 4.4 | 0.033 |
| IgG | 14.7 | 0.108 |
| Complement Components | | |
| C3 | 121.0 | 0.893 |
| C3a | <0.0039 | <0.00003 |
| C4 | 7.0 | 0.051 |

TABLE 13-continued

Biochemical characterization of purified Factor H composition.

| Others | | Unit |
|---|---|---|
| FXI | <0.25 | [ng/mL] |
|  | 0.02 | [IU/mL] |
| Endotoxin | <0.5 |  |
| TGA | 126.4 | [% of normal plasma control at 10 mg/mL protein] |
| PKKA | 6.7 | [IU/mL] |
| NAPTT | >1.36 | [mg] |

| Amdiolytic Impurities | | Unit |
|---|---|---|
| FXIa, Trypsin | 21 5 | [nmol/mL * min] |
| Plasmin | <5 |  |
| FXIa, glandular Kallikreins | <5 |  |
| Broad Spectrum (S-2288) | <5 |  |
| Broad Spectrum (PL-1) | <5 |  |
| Kallikrein, FXIa, FXIIa | <5 |  |

| Process Impurities | | Unit |
|---|---|---|
| Polysorbate 80 | <26 | ppm |
| TNBP | <0.2 |  |
| Triton | <0.1 |  |

To determine the factor H molecular size distribution profile as measured by SEC-HPLC, a standard plasma-derived Factor H sample (CompTech) was concentrated to 0.6% protein content and tested. The HPLC profile of a Factor H composition purified as described in Example 17 was also tested. Both profiles are shown in Table 14.

Interestingly, plasma-derived Factor H protein concentrated to 0.6%, which is necessary for HPLC testing, elutes with an apparent molecular weight of at about 400 kDa as a main peak (monomeric Factor H has a molecular weight: 155 kDa) and shows slight aggregation. No fragments were observed. The plasma derived Factor H sample prepared as above showed a similar elution profile, with slightly higher aggregation and fragment contents (1.1% aggregates, 95.3% monomer (eluting at 400 kDa) and 3.6% fragments, before sterile filtration).

TABLE 14

SEC-HPLC elution profile for plasma-derived Factor H (CompTech) and plasma-derived Factor H purified from Fraction II + III silicon dioxide filter cake (pFactor H).

| Sample | Peak 1 >450 Kda | Peak 2 ~400 kDa % area | Peak 3 <160 kDa |
|---|---|---|---|
| CompTech FH Standard (0.6% protein) | 0.37 | 99.6 | — |
| pFactor H | 1.1 | 95.3 | 3.6 |

Example 19—Biochemical Characterization of Factor H Prepared from Fraction II+III Silicon Dioxide Filter Cake The biochemical properties of the Factor H composition prepared in Example 17 were investigated and compared to those of a Factor H composition prepared from Fraction II+III silicon dioxide filter cake as described in Example 1. These analyses show that the improved process steps provided herein for purifying Factor H from Fraction II+III silicon dioxide filter cake significantly increase the biochemical activities of the final Factor H composition. Taken together, these results demonstrate that the improved Factor H process steps, including Fraction II+III silicon dioxide filter cake extraction, heat treatment, and improved chromatographic enrichment, provide significant improvement over previously known methods for purifying Factor H from plasma.

Figure 16:
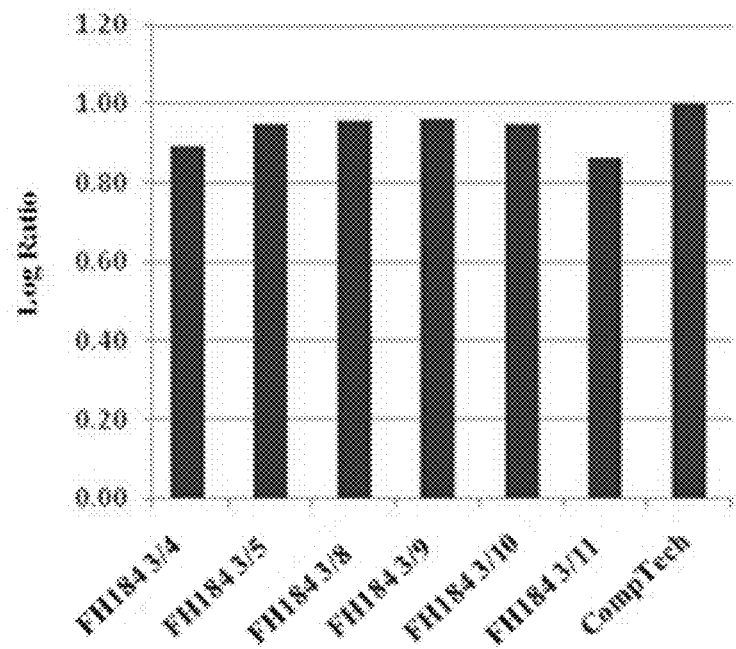
FIG. 16 illustrates the results of decay acceleration (DAF) assays performed with recombinant Factor H (CompTech) and Factor H purified from Fraction II+III silicon dioxide filter cake according to Example 16. FH184 3/4 (final container formulated at pH 5.3); FH184 3/8 (final container formulated at pH 5.3, lyophilized and dissolved in WFI directly before testing); FH184 3/10 (final container formulated at pH 5.3 and stored at 2-8° C. for 1 month); FH184 3/5 (final container formulated at pH 6.8); FH184 3/9 (final container formulated at pH 6.8, lyophilized and dissolved in WFI directly before testing); FH184 3/11 (final container formulated at pH 6.8 and stored at 2-8° C. for 1 month); and CompTech (recombinant Factor H standard).

First, the ability of Factor H to displace factor B fragment Bb from C3 convertase complexes (C3b-Bb) was determined by an ELISA method. Plasma-derived Factor H (CompTech) was used as a standard, and the ratio of sample binding to standard binding was evaluated at the logarithmic value of half maximal inhibitor concentration ($IC_{50}$). Lower values show increased Factor H activity, as they indicate less functional convertase complexes remaining after Factor H challenge. Notably, the ratio of decay acceleration activity is illustrated in FIG. 16 for samples of the Factor H composition prepared in Example 17, treated in various fashions. All of the plasma-derived Factor H samples have activity ratios below 1.0, reflecting a higher activity than the plasma-derived Factor H standard. This activity remains also intact after lyophilization and storage for 1 month at 2-8° C.

Samples tested include: FH184 3/4 (final container formulated at pH 5.3); FH184 3/8 (final container formulated at pH 5.3, lyophilized and dissolved in WFI directly before testing); FH184 3/10 (final container formulated at pH 5.3 and stored at 2-8° C. for 1 month); FH184 3/5 (final container formulated at pH 6.8); FH184 3/9 (final container formulated at pH 6.8, lyophilized and dissolved in WFI directly before testing); FH184 3/11 (final container formulated at pH 6.8 and stored at 2-8° C. for 1 month); and CompTech (plasma-derived Factor H standard).

Figure 17:
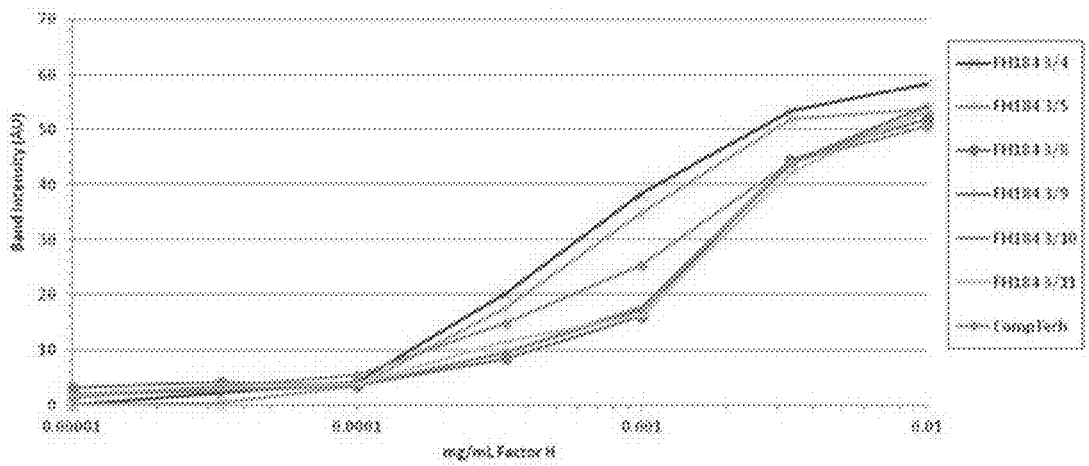
FIG. 17 illustrates the results of Factor I cofactor assays performed with recombinant Factor H (CompTech) and Factor H purified from Fraction II+III silicon dioxide filter cake according to Example 16. FH184 3/4 (final container formulated at pH 5.3); FH184 3/8 (final container formulated at pH 5.3, lyophilized and dissolved in WFI directly before testing); FH184 3/10 (final container formulated at pH 5.3 and stored at 2-8° C. for 1 month); FH184 3/5 (final container formulated at pH 6.8); FH184 3/9 (final container formulated at pH 6.8, lyophilized and dissolved in WFI directly before testing); FH184 3/11 (final container formulated at pH 6.8 and stored at 2-8° C. for 1 month); and CompTech (recombinant Factor H standard).

The Factor I co-factor activity was then assessed for each of the plasma-derived samples tested in the decay acceleration assay described above. The Factor I co-factor activity was determined by measuring the band intensity (AU) of a band at 43 kDa (cleavage of C3b into C3b fragments applying factor I and factor H). As shown in FIG. 17, Factor H samples freshly prepared as described in Example 17 (FH184 3/4 and FH184 3/5) have higher Factor I cofactor activity than does the plasma-derived Factor H control (CompTech). Factor H lyophilized and stored at 2-8° C. for 1 month show comparable activity as the plasma-derived Factor H control. Samples were labeled in FIG. 17 as for FIG. 16.

Briefly, the Factor I co-factor assay, first described by Alsenz et al. 1994, is performed by diluting a factor I standard 1:20 with PBS followed by the preparation of a dilution series of the FH standard as well as the sample starting with 100 μg/mL Factor H, 10 μg/mL, 3 μg/mL, 1 μg/mL and 0.1 μg/mL. The reaction is carried out on ice by mixing 10 μl PBS, 5 μl concentrated C3b, 5 μl diluted factor I and finally 10 μl of the FH standard or sample dilution. Each vial is incubated for 1 hour at 37° C. in a incubator. After this incubation, 30 μl Laemmli sample buffer (containing beta-mercaptoethanol in a ratio 1:20) is added to each vial. The vials are then incubated for 5 min at 95° C., centrifuged, and 40 μg per reaction batch are loaded on a 7.5% SDS gel. The molecular weight of a band can be determined by comparing it to the molecular weight size marker. The band at about 43 kDa is then quantified by densitometry using the ImageJ program for image processing and analysis. This size reflects the cleavage product of C3b into C3b inactive fragment by factor I and Factor H. The sample data obtained can be compared with the data from the commercially available Factor H standard.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for preparing an enriched Factor H composition from plasma, the method comprising the steps:
   (A) precipitating Factor H from a Cohn plasma pool or Fraction I supernatant with alcohol, thereby forming a Factor H-precipitate;
   (B) suspending the Factor H precipitate in a suspension buffer, thereby forming a Factor H suspension,
   (C) contacting the Factor H suspension with finely divided silicon dioxide ($SiO_2$);
   (D) separating the Factor H suspension into a soluble fraction and an insoluble fraction;
   (E) extracting Factor H from the insoluble fraction separated in step (D) with an extraction buffer comprising a conductivity of from 15 mS/cm to 24 mS/cm and a pH of from 4.6 to 5.4, thereby forming a Factor H extract; and
   (F) chromatographically enriching the Factor H extract, the enriching comprising:
      (1) forming a first Factor H enriched mixture by anion exchange chromatography, comprising:
         (i) binding Factor H from the Factor H extract to an anion exchange resin using solution conditions comprising, a conductivity of from about 2 mS/cm to about 5 mS/cm and a pH of about 6.1 to about 6.7; and
         (ii) eluting Factor H from the anion exchange resin using solution conditions comprising either:
            a) a conductivity of from about 20 mS/cm to about 30 mS/cm and a pH of from about 6.0 to about 7.5, or
            b) a conductivity of from about 10 mS/cm to about 20 mS/cm and a pH of from about 7.5 to about 8.5, thereby forming the first Factor H enriched mixture;
      (2) forming a second Factor H enriched mixture by heparin affinity chromatography, comprising:
         (i) binding Factor H from the first Factor H enriched mixture to a heparin affinity resin using solution conditions comprising a conductivity of from about 7 mS/cm to about 11 mS/cm and a pH of from about 6.9 to about 7.5; and
         (ii) eluting Factor H from the heparin affinity resin using solution conditions comprising a conductivity of from about 25 mS/cm to about 35 mS/cm and a pH of from about 7.7 to about 8.3, thereby forming the second Factor H enriched mixture; and
      (3) forming a third Factor H enriched mixture by mixed mode resin chromatography, comprising:
         (i) binding Factor H from the second Factor H enriched mixture to a mixed mode chromatography resin using solution conditions comprising a conductivity of from about 15 mS/cm to about 40 mS/cm and a pH of from about 6.7 to about 7.9; and
         (ii) eluting Factor H from the mixed mode chromatography resin using solution conditions comprising a conductivity of from about 4 mS/cm to about 11 mS/cm and a pH of from about 4.3 to about 5.0, thereby forming the third Factor H enriched mixture.

2. The method of claim 1, wherein Factor H is precipitated from a Cohn plasma pool in step (A).

3. The method of claim 1, wherein Factor H is precipitated from a Fraction I supernatant in step (A).

4. The method of claim 1, wherein precipitating (A) includes incubating the Cohn plasma pool or Fraction I supernatant after addition of alcohol to a final concentration of from 17% to 27% at a pH of from 5.5 to 7.0.

5. The method of claim 4, wherein the Cohn plasma pool or Fraction I supernatant is incubated after addition of alcohol to a final concentration of from 20% to 25% at a pH of from 6.5 to 7.0.

6. The method of claim 4, wherein the alcohol is ethanol.

7. The method of claim 6, wherein the ethanol is denatured ethanol.

8. The method of claim 1, wherein the Factor H precipitate is suspended in step (B) with a suspension buffer having a pH of from 4.0 to 6.0 and a conductivity of from 0.5 mS/cm to 2.0 mS/cm.

9. The method of claim 1, wherein the Factor H suspension is contacted in step (C) with from 5 g $SiO_2$/kg suspended Factor H precipitate to 200 g $SiO_2$/kg suspended Factor H precipitate.

10. The method of claim 1, wherein the insoluble fraction of the $SiO_2$ treated Factor H suspension is separated in step (D) by filtration.

11. The method of claim 10, wherein the filtration in step (D) is performed in a filter press and Factor H is extracted in step (E) by circulating an extraction buffer through the filter press containing the separated insoluble fraction.

12. The method of claim 1, wherein the extraction buffer has a conductivity of 19±2 mS/cm.

13. The method of claim 1, wherein the extraction buffer has a pH of 5.0±0.2.

14. The method of claim 1, further comprising a heat treatment step performed at a temperature of from 60° C. to 75° C. and a pH of from 4.5 to 7.0 for 1 to 3 hours in the presence of from 2.5% to 7.5% of a sugar, a sugar alcohol, or a combination thereof.

15. The method of claim 14, wherein the sugar, sugar alcohol, or combination thereof is sucrose, glucose, sorbitol, or a combination thereof.

16. The method of claim 14, wherein the sugar, sugar alcohol, or combination thereof is glucose.

17. The method of claim 1, wherein the mixed mode resin includes an aliphatic ligand.

18. The method of claim 1, wherein the mixed mode resin includes an aromatic ligand.

19. The method of claim 1, further comprising a wash step between the mixed mode binding step (3)(i) and the mixed mode eluting step (3)(ii), the wash step comprising:
   washing the bound mixed mode chromatography resin with a wash buffer having a conductivity of from 10 mS/cm to 50 mS/cm and a pH of from 6.2 to 7.3.

* * * * *